US012648924B2

(12) United States Patent
Koutnik et al.

(10) Patent No.: US 12,648,924 B2
(45) Date of Patent: Jun. 9, 2026

(54) PREVENTION AND TREATMENT OF EFFECTS OF AGING AND AGE-ASSOCIATED DISORDERS WITH KETONE SUPPLEMENTATION

(71) Applicant: UNIVERSITY OF SOUTH FLORIDA, Tampa, FL (US)

(72) Inventors: Andrew Paul Koutnik, Tampa, FL (US); Dominic Paul D'Agostino, Tampa, FL (US)

(73) Assignee: University of South Florida, Tampa, FL (US)

( * ) Notice: Subject to any disclaimer, the term of this patent is extended or adjusted under 35 U.S.C. 154(b) by 794 days.

(21) Appl. No.: 17/794,756

(22) PCT Filed: Jan. 22, 2021

(86) PCT No.: PCT/US2021/014673
    § 371 (c)(1),
    (2) Date: Jul. 22, 2022

(87) PCT Pub. No.: WO2021/150928
    PCT Pub. Date: Jul. 29, 2021

(65) Prior Publication Data
    US 2023/0172891 A1     Jun. 8, 2023

Related U.S. Application Data

(60) Provisional application No. 62/964,952, filed on Jan. 23, 2020.

(51) Int. Cl.
    *A61K 31/22*      (2006.01)
    *A61K 9/00*       (2006.01)
    *A61K 45/06*      (2006.01)
    *A61P 43/00*      (2006.01)

(52) U.S. Cl.
    CPC ............ *A61K 31/22* (2013.01); *A61K 9/0053* (2013.01); *A61K 45/06* (2013.01); *A61P 43/00* (2018.01)

(58) Field of Classification Search
    CPC .................................................... A61K 31/22
    See application file for complete search history.

(56) References Cited

U.S. PATENT DOCUMENTS

| | | | |
|---|---|---|---|
| 4,559,157 A | 12/1985 | Smith et al. | |
| 4,608,392 A | 8/1986 | Jacquet et al. | |
| 4,820,508 A | 4/1989 | Wortzman | |
| 4,938,949 A | 7/1990 | Borch et al. | |
| 4,992,478 A | 2/1991 | Geria | |
| 5,167,649 A | 12/1992 | Zook | |
| 6,960,648 B2 | 11/2005 | Bonny | |
| 8,124,589 B2 * | 2/2012 | Henderson | A61P 25/28 |
| | | | 514/23 |
| 10,980,764 B1 * | 4/2021 | D'Agostino | A23L 33/12 |

| | | | |
|---|---|---|---|
| 2002/0035243 A1 | 3/2002 | Imfeld et al. | |
| 2002/0120100 A1 | 8/2002 | Bonny | |
| 2003/0032594 A1 | 2/2003 | Bonny | |
| 2017/0000754 A1 | 1/2017 | Weeber | |
| 2017/0266148 A1 * | 9/2017 | D'Agostino | A61K 31/19 |
| 2021/0189914 A1 * | 6/2021 | Barnes | F01L 1/026 |

OTHER PUBLICATIONS

International Search Report and Written Opinion in PCT/2021/014673. Mailed Apr. 9, 2021.
Fearon, K., et al., Definition and classification of cancer cachexia: an international consensus. Lancet Oncol, 2011. 12(5): p. 489-95.
Evans, W.J., et al., Cachexia: a new definition. Clin Nutr, 2008. 27(6): p. 793-9.
Argiles, J.M., et al., Cancer cachexia: understanding the molecular basis. Nat Rev Cancer, 2014. 14(11): p. 754-62.
Warren, S., The Immediate Causes of Death in Cancer. Am J Med Sci, 1932. 183(13): p. 610-613.
Von Haehling, S., M.S. Anker, and S.D. Anker, Prevalence and clinical impact of cachexia in chronic illness in Europe, USA, and Japan: facts and numbers update 2016. J Cachexia Sarcopenia Muscle, 2016. 7(5): p. 507-509.
Penna, F., S. Busquets, and J.M. Argiles, Experimental cancer cachexia: Evolving strategies for getting closer to the human scenario. Semin Cell Dev Biol, 2016. 54: p. 20-7.
Tomasin, R., A. Martin, and M.R. Cominetti, Metastasis and cachexia: alongside in clinics, but not so in animal models. J Cachexia Sarcopenia Muscle, 2019.
Bennani-Baiti, N. and D. Walsh, What is cancer anorexia-cachexia syndrome? A historical perspective. J R Coll Physicians Edinb, 2009. 39(3): p. 257-62.
Dewys, W.D., et al., Prognostic effect of weight loss prior to chemotherapy in cancer patients. Eastern Cooperative Oncology Group. Am J Med, 1980. 69(4): p. 491-7.
Muscaritoli, M., et al., Prevalence of malnutrition in patients at first medical oncology visit: the PreMiO study. Oncotarget, 2017. 8(45): p. 79884-79896.
Caillet, P., et al., Association between cachexia, chemotherapy and outcomes in older cancer patients: A systematic review. Clin Nutr, 2016.

(Continued)

*Primary Examiner* — Rei Tsang Shiao
(74) *Attorney, Agent, or Firm* — Meunier Carlin & Curfman LLC

(57) ABSTRACT

Methods and compositions for preventing, reducing, delaying, or reversing effects due to aging or preventing, treating, or reducing time to recovery from a disease associated with aging, as well as anemia, hypoalbuminemia, hypocholesterolemia, malnutrition/anorexia/starvation, and/or splenomegaly in a subject in need thereof are disclosed. The method can include administering a therapeutically effective amount of a ketogenic supplement to the subject, wherein the subject is fed ad libitum. The ketogenic supplement can include R,S 1,3-butanediol acetoacetate diester or derivatives thereof.

17 Claims, 30 Drawing Sheets
Specification includes a Sequence Listing.

(56)  References Cited

OTHER PUBLICATIONS

Wang, G., et al., Metastatic cancers promote cachexia through ZIP14 upregulation in skeletal muscle. Nat Med, 2018. 24(6): p. 770-781.

Huysentruyt, L.C., et al., Metastatic cancer cells with macrophage properties: evidence from a new murine tumor model. Int J Cancer, 2008. 123(1): p. 73-84.

Poff, A.M., et al., Non-Toxic Metabolic Management of Metastatic Cancer in VM Mice: Novel Combination of Ketogenic Diet, Ketone Supplementation, and Hyperbaric Oxygen Therapy. PLoS One, 2015. 10(6): p.e0127407.

Cahill, G.F., Jr., Starvation in man. N Engl J Med, 1970. 282(12): p. 668-75.

Sherwin, R.S., R.G. Hendler, and P. Felig, Effect of ketone infusions on amino acid and nitrogen metabolism in man. J Clin Invest, 1975. 55(6): p. 1382-90.

Thomsen, H.H., et al., Effects of 3-hydroxybutyrate and free fatty acids on muscle protein kinetics and signaling during LPS-induced inflammation in humans: anticatabolic impact of ketone bodies. Am J Clin Nutr, 2018. 108(4): p. 857-867.

Nair, K.S., et al., Effect of beta-hydroxybutyrate on whole-body leucine kinetics and fractional mixed skeletal muscle protein synthesis in humans. J Clin Invest, 1988. 82(1): p. 198-205.

Vandoorne, T., et al., Intake of a Ketone Ester Drink during Recovery from Exercise Promotes mTORC1 Signaling but Not Glycogen Resynthesis in Human Muscle. Front Physiol, 2017. 8: p. 310.

Shukla, S.K., et al., Metabolic reprogramming induced by ketone bodies diminishes pancreatic cancer cachexia. Cancer Metab, 2014. 2: p. 18.

Zou, X., et al., Acetoacetate Accelerates Muscle Regeneration and Ameliorates Muscular Dystrophy in Mice. J Biol Chem, 2016. 291(5): p. 2181-95.

Roberts, M.N., et al., A Ketogenic Diet Extends Longevity and Healthspan in Adult Mice. Cell Metab, 2018. 27(5): p. 1156.

Poff, A., et al., Targeting the Warburg effect for cancer treatment: Ketogenic diets for management of glioma. Semin Cancer Biol, 2017.

Newman, J.C. and E. Verdin, beta-Hydroxybutyrate: A Signaling Metabolite. Annu Rev Nutr, 2017. 37: p. 51-76.

Kovacs, Z., et al., Exogenous Ketone Supplementation Decreased the Lipopolysaccharide-Induced Increase in Absence Epileptic Activity in Wistar Albino Glaxo Rijswijk Rats. Front Mol Neurosci, 2019. 12: p. 45.

Youm, Y.H., et al., The ketone metabolite beta-hydroxybutyrate blocks NLRP3 inflammasome-mediated inflammatory disease. Nat Med, 2015. 21(3): p. 263-9.

Koutnik, A.P., D.P. D'Agostino, and B. Egan, Anticatabolic Effects of Ketone Bodies in Skeletal Muscle. Trends Endocrinol Metab, 2019. 30(4): p. 227-229.

Wagner, F., P. Radermacher, and W. Stahl, Anesthesia and the immune response: evidence for an "isoflurane paradox"? Shock, 2010. 34(4): p. 437-8.

Nader, G.A., T.J. McLoughlin, and K.A. Esser, mTOR function in skeletal muscle hypertrophy: increased ribosomal RNA via cell cycle regulators. Am J Physiol Cell Physiol, 2005. 289(6): p. C1457-65.

Haun, C.T., et al., Pre-training Skeletal Muscle Fiber Size and Predominant Fiber Type Best Predict Hypertrophic Responses to 6 Weeks of Resistance Training in Previously Trained Young Men. Front Physiol, 2019. 10: p. 297.

Motulsky, H.J. and R.E. Brown, Detecting outliers when fitting data with nonlinear regression—a new method based on robust nonlinear regression and the false discovery rate. BMC Bioinformatics, 2006. 7: p. 123.

Sangisetty, S.L. and T.J. Miner, Malignant ascites: A review of prognostic factors, pathophysiology and therapeutic measures. World J Gastrointest Surg, 2012. 4(4): p. 87-95.

Baracos, V.E. and L. Arribas, Sarcopenic obesity: hidden muscle wasting and its impact for survival and complications of cancer therapy. Ann Oncol, 2018. 29(suppl_2): p. ii1-ii9.

Maltoni, M., et al., High-dose progestins for the treatment of cancer anorexia-cachexia syndrome: a systematic review of randomised clinical trials. Ann Oncol, 2001. 12(3): p. 289-300.

Loprinzi, C.L., et al., Body-composition changes in patients who gain weight while receiving megestrol acetate. J Clin Oncol, 1993. 11(1): p. 152-4.

Murphy, K.T., et al., Importance of functional and metabolic impairments in the characterization of the C-26 murine model of cancer cachexia. Dis Model Mech, 2012. 5(4): p. 533-45.

Miokovic, T., et al., Heterogeneous atrophy occurs within individual lower limb muscles during 60 days of bed rest. J Appl Physiol (1985), 2012. 113(10): p. 1545-59.

Stephens, N.A., et al., Sexual dimorphism modulates the impact of cancer cachexia on lower limb muscle mass and function. Clin Nutr, 2012. 31(4): p. 499-505.

Cosper, P.F. and L.A. Leinwand, Cancer causes cardiac atrophy and autophagy in a sexually dimorphic manner. Cancer Res, 2011. 71(5): p. 1710-20.

Baracos, V.E., et al., Body composition in patients with non-small cell lung cancer: a contemporary view of cancer cachexia with the use of computed tomography image analysis. Am J Clin Nutr, 2010. 91(4): p. 1133S-1137S.

Enns, D.L. and P.M. Tiidus, The influence of estrogen on skeletal muscle: sex matters. Sports Med, 2010. 40(1): p. 41-58.

Mauvais-Jarvis, F., D.J. Clegg, and A.L. Hevener, The role of estrogens in control of energy balance and glucose homeostasis. Endocr Rev, 2013. 34(3): p. 309-38.

Tsoli, M. and G. Robertson, Cancer cachexia: malignant inflammation, tumorkines, and metabolic mayhem. Trends Endocrinol Metab, 2013. 24(4): p. 174-83.

Bronte, V. and M.J. Pittet, The spleen in local and systemic regulation of immunity. Immunity, 2013. 39(5): p. 806-18.

Platzbecker, U., et al., Spleen enlargement in healthy donors during G-CSF mobilization of PBPCs. Transfusion, 2001. 41(2): p. 184-9.

Fouladiun, M., et al., Daily physical-rest activities in relation to nutritional state, metabolism, and quality of life in cancer patients with progressive cachexia. Clin Cancer Res, 2007. 13(21): p. 6379-85.

Bennegard, K., et al., Metabolic balance across the leg in weight-losing cancer patients compared to depleted patients without cancer. Cancer Res, 1982. 42(10): p. 4293-9.

Eden, E., et al., Glucose flux in relation to energy expenditure in malnourished patients with and without cancer during periods of fasting and feeding. Cancer Res, 1984. 44(4): p. 1718-24.

Holroyde, C.P., et al., Lactate metabolism in patients with metastatic colorectal cancer. Cancer Res, 1979. 39(12): p. 4900-4.

Holroyde, C.P., et al., Altered glucose metabolism in metastatic carcinoma. Cancer Res, 1975. 35(12): p. 3710-4.

Tracey, K.J., et al., Cachectin/tumor necrosis factor induces cachexia, anemia, and inflammation. J Exp Med, 1988. 167(3): p. 1211-27.

Gupta, D. and C.G. Lis, Pretreatment serum albumin as a predictor of cancer survival: a systematic review of the epidemiological literature. Nutr J, 2010. 9: p. 69.

Utech, A.E., et al., Predicting survival in cancer patients: the role of cachexia and hormonal, nutritional and inflammatory markers. J Cachexia Sarcopenia Muscle, 2012. 3(4): p. 245-51.

Ettinger, W.H., Jr., et al., Interleukin-6 causes hypocholesterolemia in middle-aged and old rhesus monkeys. J Gerontol A Biol Sci Med Sci, 1995. 50(3): p. M137-40.

Gilbert, H.S., et al., Characterization of hypocholesterolemia in myeloproliferative disease. Relation to disease manifestations and activity. Am J Med, 1981. 71(4): p. 595-602.

Bonaldo, P. and M. Sandri, Cellular and molecular mechanisms of muscle atrophy. Dis Model Mech, 2013. 6(1): p. 25-39.

Sharples, A.P., et al., Longevity and skeletal muscle mass: the role of IGF signalling, the sirtuins, dietary restriction and protein intake. Aging Cell, 2015. 14(4): p. 511-23.

Lecker, S.H., A.L. Goldberg, and W.E. Mitch, Protein degradation by the ubiquitin-proteasome pathway in normal and disease states. J Am Soc Nephrol, 2006. 17(7): p. 1807-19.

(56)                    References Cited

OTHER PUBLICATIONS

Karin, M. and Y. Ben-Neriah, Phosphorylation meets ubiquitination: the control of NF-[kappa]B activity. Annu Rev Immunol, 2000. 18: p. 621-63.

Li, Y.P. and M.B. Reid, NF-kappaB mediates the protein loss induced by TNF-alpha in differentiated skeletal muscle myotubes. Am J Physiol Regul Integr Comp Physiol, 2000. 279(4): p. R1165-70.

Hoffmann, A., et al., The IkappaB-NF-kappaB signaling module: temporal control and selective gene activation. Science, 2002. 298(5596): p. 1241-5.

Guttridge, D.C., et al., NF-kappaB-induced loss of MyoD messenger RNA: possible role in muscle decay and cachexia. Science, 2000. 289(5488): p. 2363-6.

Digby, J.E., et al., Anti-inflammatory effects of nicotinic acid in human monocytes are mediated by GPR109A dependent mechanisms. Arterioscler Thromb Vasc Biol, 2012. 32(3): p. 669-76.

Feingold, K.R., et al., Inflammation stimulates niacin receptor (GPR109A/HCA2) expression in adipose tissue and macrophages. J Lipid Res, 2014. 55(12): p. 2501-8.

Dhingra, S., et al., IL-10 attenuates TNF-alpha-induced NF kappaB pathway activation and cardiomyocyte apoptosis. Cardiovasc Res, 2009. 82(1): p. 59-66.

Sandri, M., et al., Foxo transcription factors induce the atrophy-related ubiquitin ligase atrogin-1 and cause skeletal muscle atrophy. Cell, 2004. 117(3): p. 399-412.

Beharry, A.W., et al., HDAC1 activates FoxO and is both sufficient and required for skeletal muscle atrophy. J Cell Sci, 2014. 127(Pt 7): p. 1441-53.

Deemer, S.E., et al., Concentration-Dependent Effects of a Dietary Ketone Ester on Components of Energy Balance in Mice. Front. Nutr., 2019.

Davis, R.A.H., et al., Dietary R, S-1,3-butanediol diacetoacetate reduces body weight and adiposity in obese mice fed a high-fat diet. FASEB J, 2019. 33(2): p. 2409-2421.

Zentella, A., K. Manogue, and A. Cerami, Cachectin/TNF-mediated lactate production in cultured myocytes is linked to activation of a futile substrate cycle. Cytokine, 1993. 5(5): p. 436-47.

Vander Heiden, M.G., L.C. Cantley, and C.B. Thompson, Understanding the Warburg effect: the metabolic requirements of cell proliferation. Science, 2009. 324(5930): p. 1029-33.

De Wilde, J., et al., The embryonic genes Dkk3, Hoxd8, Hoxd9 and Tbx1 identify muscle types in a dietindependent and fiber-type unrelated way. BMC Genomics, 2010. 11: p. 176.

Sun, R., et al., Valproic acid attenuates skeletal muscle wasting by inhibiting C/EBPbeta-regulated atrogin1 expression in cancer cachexia. Am J Physiol Cell Physiol, 2016. 311(1): p. C101-15.

Montalvo, R.N., B.R. Counts, and J.A. Carson, Understanding sex differences in the regulation of cancerinduced muscle wasting. Curr Opin Support Palliat Care, 2018. 12(4): p. 394-403.

Fukawa, T., et al., Excessive fatty acid oxidation induces muscle atrophy in cancer cachexia. Nat Med, 2016. 22(6): p. 666-71.

Norman, K., et al., Effect of sexual dimorphism on muscle strength in cachexia. J Cachexia Sarcopenia Muscle, 2012. 3(2): p. 111-6.

D'Agostino, D.P., et al., Therapeutic ketosis with ketone ester delays central nervous system oxygen toxicity seizures in rats. Am J Physiol Regul Integr Comp Physiol, 2013. 304(10): p. R829-36.

Kesl, S.L., et al., Effects of exogenous ketone supplementation on blood ketone, glucose, triglyceride, and lipoprotein levels in Sprague-Dawley rats. Nutr Metab (Lond), 2016. 13: p. 9.

Dansinger, M.L., et al., Comparison of the Atkins, Ornish, Weight Watchers, and Zone diets for weight loss and heart disease risk reduction: a randomized trial. JAMA, 2005. 293(1): p. 43-53.

Weber, D.A.-G., S. Tulipan, J. Catalano, L. Feichtinger, RG. Kofler, B., Ketogenic diet in the treatment of cancer—Where do we stand? Molecular Metabolism, 2019.

Poff, A.M., et al., Ketone supplementation decreases tumor cell viability and prolongs survival of mice with metastatic cancer. Int J Cancer, 2014. 135(7): p. 1711-20.

Schakman, O., et al., Role of IGF-I and the TNFalpha/NF-kappaB pathway in the induction of muscle atrogenes by acute inflammation. Am J Physiol Endocrinol Metab, 2012. 303(6): p. E729-39.

Costelli, P., et al., IGF-1 is downregulated in experimental cancer cachexia. Am J Physiol Regul Integr Comp Physiol, 2006. 291(3): p. R674-83.

Walsh, M.E. and H. Van Remmen, Emerging roles for histone deacetylases in age-related muscle atrophy. Nutr Healthy Aging, 2016. 4(1): p. 17-30.

Penna, F. and P. Costelli, New developments in investigational HDAC inhibitors for the potential multimodal treatment of cachexia. Expert Opin Investig Drugs, 2019. 28(2): p. 179-189.

Pigna, E., et al., HDAC4 preserves skeletal muscle structure following long-term denervation by mediating distinct cellular responses. Skelet Muscle, 2018. 8(1): p. 6.

Pigna, E., et al., Histone deacetylase 4 protects from denervation and skeletal muscle atrophy in a murine model of amyotrophic lateral sclerosis. EBioMedicine, 2019. 40: p. 717-732.

Shimazu, T., et al., Suppression of oxidative stress by beta-hydroxybutyrate, an endogenous histone deacetylase inhibitor. Science, 2013. 339(6116): p. 211-4.

Hobler, S.C., et al., IGF-I stimulates protein synthesis but does not inhibit protein breakdown in muscle from septic rats. Am J Physiol, 1998. 274(2): p. R571-6.

Broussard, S.R., et al., IL-1beta impairs insulin-like growth factor i-induced differentiation and downstream activation signals of the insulin-like growth factor i receptor in myoblasts. J Immunol, 2004. 172(12): p. 7713-20.

Broussard, S.R., et al., Cytokine-hormone interactions: tumor necrosis factor alpha impairs biologic activity and downstream activation signals of the insulin-like growth factor I receptor in myoblasts. Endocrinology, 2003. 144(7): p. 2988-96.

Frost, R.A., C.H. Lang, and M.C. Gelato, Transient exposure of human myoblasts to tumor necrosis factoralpha inhibits serum and insulin-like growth factor-I stimulated protein synthesis. Endocrinology, 1997. 138(10): p. 4153-9.

Samani, A.A., et al., The role of the IGF system in cancer growth and metastasis: overview and recent insights. Endocr Rev, 2007. 28(1): p. 20-47.

Von Haehling, S., et al., Ethical guidelines for publishing in the journal of cachexia, sarcopenia and muscle: update 2017. J Cachexia Sarcopenia Muscle, 2017. 8(6): p. 1081-1083.

Chu, et al; Int J Clin Exp Med 2015; 8(5) 7684-7688; (R)-3-oxobutyl 3-Hydroxybutanoate (OBHB).†

Newport, et al; Alzheimer's Diment 2015; 11(1) 99-103; A new way to produce hyperketonemia: use of a ketone ester in a case of Alzheimer's disease.†

Almeida-Suhett et al; Nutritional Neuroscience, 25:6, 1287-1299 (2022; The ketone ester, 3-hydroxybutyl-3-hydroxybutyrate, attenuates neurobehavioral deficits and Improves neuropathy following controlled cortical impact in male rats.†

Merck Manual of Diagnosis and Therapy 18th Ed 2006 p. 1815.†

Rebello, et al; BBA Clinical 3 (2015) 123-125; Pilot feasibility and safety study examining the effects of medium chain triglyceride supplementation in subjects with cognitive impairment: a randomized controlled trial.†

Hashim, e al; J. Lipid Res. 2014, 55:1818-1826; Ketone Body Therapy: From the Ketogenic Diet to the Oral Administration of Ketone Ester.†

Ingle et al, Journal of Food Science, vol. 64, No. 6, 1999 pp. 960-963; Dietary Energy Value ol Medium Chain Triglycerides.†

De La Rubia Orti et al; Journal of Alzheimer's Disease 65 (2018) 577-587; Improvement of Main Cognitive Functions in Patient's with Alzheimer's Disease After Treatment of Coconut Enriched Mediterranean Diet: A Pilot Study.†

Gandotra et al; Int J Sch Cog Psychol 2014, 1:2 (10 pages); Efficacy of Adjunctive Extra Virgin Coconut Oil Use in Moderate to Severe Alzheimer's Disease.†

Merck Manual of Diagnosis and Therapy, 18th Edition 2006, p. 1815.†

Hashim et al; J. Lipid Res. 2014, 55:1818-1826; Ketone Body Therapy: From the Ketogenic Diet to the Oral Administration of Ketone Ester.†

(56)           References Cited

OTHER PUBLICATIONS

Newport, et al; Alzheimers Diment 2015; 11(1) 99-103; A new way to produce hyperketonemia: use of ketone ester in a case of Alzheimer's disease.†

Almeida-Suhett, et al; Nutritional Neuroscience, 26:6, 1287-1299 (2022); The ketone ester, 3-hydroxybutyl-3-hydroxybutyrate, attenuales neurobehavioral deficits and improves neuropathology following controlled cortical impact in male rats.†

Rebello, et al; BBA Clinical 3 (2015) 123-125; Pilot feasibility and safety study examining the effects of medium chain triglyceride supplementation in subjects with mild cognitive impairment: A randomized controlled trial.†

Ingle, et al; Journal of Food Science, vol. 64, No. 6, 1999 pp. 960-963; Dietary Energy Value of Medium Chain Triglycerides.†

De La Rubia Orti et al; Journal of Alzheimer's Disease 65 (2018) 577-587; Improvement of Main Cognitive Functions in Patient's With Alzheimer's Disease After Treatment of Coconut Oil Enriched Mediterranean Diet: A Pilot Study.†

Gandotra et al; Int J SCH COG Psychol 2014 1:2 (10 Pgs); Efficacy of Adjunctive Extra Virgin Coconut Oil Use in Moderate To Severe Alzheimer's Disease.†

* cited by examiner
† cited by third party

C

A

E
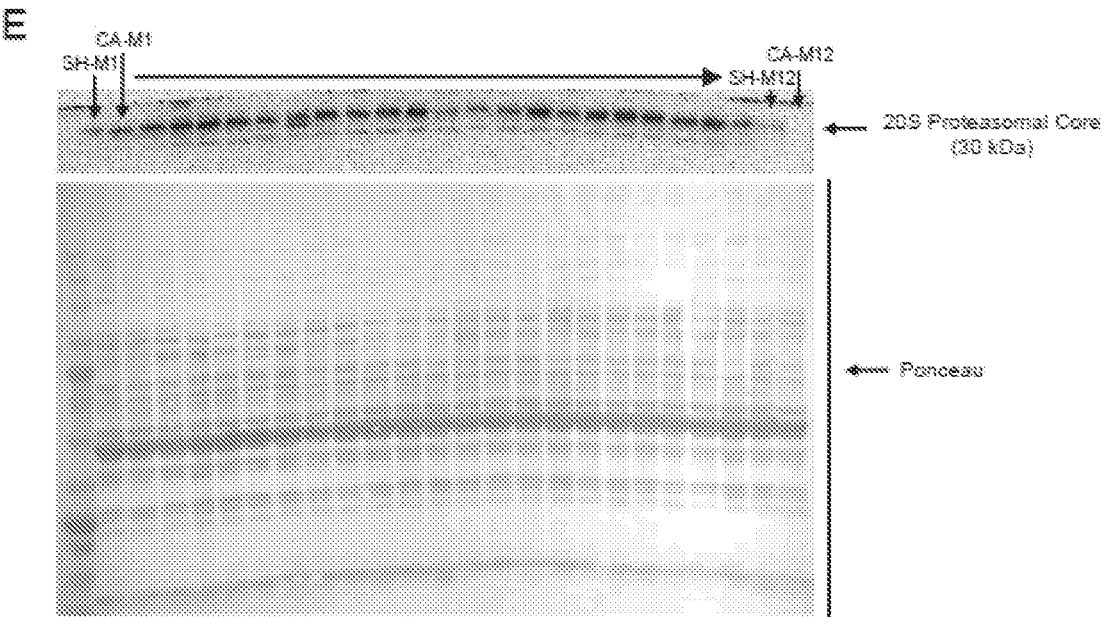
F
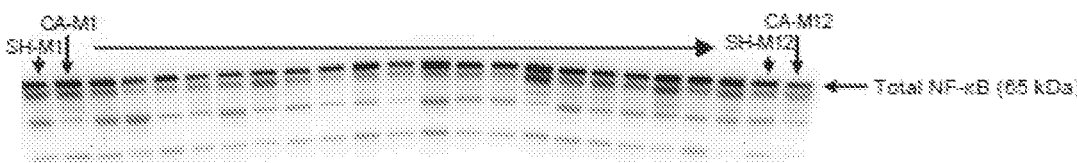
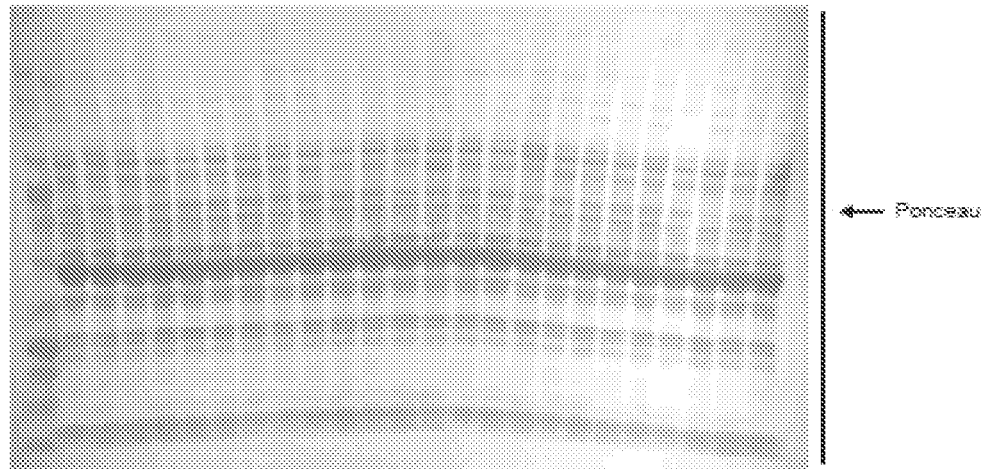
FIGS. 12E-12F

PREVENTION AND TREATMENT OF EFFECTS OF AGING AND AGE-ASSOCIATED DISORDERS WITH KETONE SUPPLEMENTATION

CROSS REFERENCE TO RELATED APPLICATIONS

This application is a national stage application filed under 35 U.S.C. § 371 of PCT/US2021/014673 filed Jan. 22, 2021, which claims the benefit of priority to U.S. Provisional Application No. 62/964,952, filed Jan. 23, 2020, the disclosure of which is incorporated by reference herein in its entirety.

STATEMENT REGARDING FEDERALLY SPONSORED RESEARCH

This invention was made with government support under N00014-18-1-2701 awarded by the Office of Naval Research. The government has certain rights in the invention.

FIELD

The disclosed subject matter relates, generally, to anti-aging agents and the use of such identified anti-aging agents in the prevention and/or treatment of effects and diseases associated with aging. More specifically, the disclosed subject matter relates to the use of exogenous ketone supplementation as anti-aging agents to prevent or treat various age-related effects and diseases.

BACKGROUND

Research on animal aging processes has become one of the most important efforts made by the scientific community in the last decade, one reason being that many elderly people have many diseases or illnesses, but many of them have no effective prevention or treatment method. Many literature exists that aids in understanding the aging process, but a complete understanding of this process is still a major scientific challenge. Among the various theories about aging processes and methods derived from theories that help treat aging diseases, nutrient signaling pathways, mitochondrial pathways, and telomere dysfunction theory are prominent. Age-related illnesses such as cancer, cardiovascular disease, and neurodegenerative disease are the leading causes of human death and are directly and/or indirectly linked to the aging process. However, drugs for the treatment of these age-related diseases are generally explored based on the current understanding of the specific disease. Given the increasing burden of health care and health care for the elderly around the world, there is a need to discover new anti-aging agents for the prevention and treatment of aging-related diseases based on the aging process. The compositions and methods disclosed herein address these and other needs.

SUMMARY

In accordance with the purposes of the disclosed materials and methods, as embodied and broadly described herein, the disclosed subject matter, in one aspect, relates effects of aging, diseases associated with aging, and compositions and methods for reducing, delaying, reversing, preventing, treating, or reducing time to recovery from these conditions. In certain aspects, disclosed are methods for preventing, reducing, delaying, or reversing effects due to aging in a subject in need thereof, the method comprising administering a therapeutically effective amount of a ketogenic supplement to the subject, in an amount of greater than 5% by weight of the subject's diet or greater than 10% of the subject's total daily caloric intake, wherein the subject is fed ad libitum. In the methods for preventing, reducing or delaying effects due to aging, the subject can be age thirty-five (35) or over, such as age sixty-five (65) or over. In the methods for reversing effects due to aging, the subject can be age sixty-five (65) or over.

In other aspects, disclosed are methods for preventing, treating, or reducing time to recovery from a disease in a subject in need thereof, the method comprising administering a therapeutically effective amount of a ketogenic supplement to the subject, in an amount of greater than 5% by weight of the subject's diet or greater than 10% of the subject's total daily caloric intake, wherein the subject is fed ad libitum. In some embodiments of the methods for preventing, treating, or reducing time to recovery from a disease, the disease can be associated with aging. For example, the subject can be age sixty-five (65) or over. The methods for preventing, treating, or reducing time to recovery from a disease as described herein, however, are not limited with respect to the age of the subject. The disease can include anemia, hypoalbuminemia, hypocholesterolemia, inflammation, malnutrition/anorexia/starvation, splenomegaly, related to elevated levels of insulin-like growth factor-1 (IGF-1), insulin, or a combination thereof; related to elevated levels of one or more cytokines (such as TNF-α; IL-6; or IL-1β); related to elevated levels of poly-ubiquitination or FOXO3a; or a combination thereof.

The subject in need thereof may exhibit elevated levels of insulin-like growth factor-1 (IGF-1), insulin, or a combination thereof, compared to an average level of IGF-1 or insulin in a population of subjects under age sixty-five (65). For example, the subject may exhibit a fasting insulin level of >4.9 µU/mL; an IGF-1 level of >150 ng/ml; a HOMA1-IR level of ≥2.5; a HOMA2-IR level of ≥1.4; a HbA1c level of >5.6% or 38 mmol/mol; a fasting blood glucose level of >99 mg/dL; an oral glucose tolerance level (1 hour test) of >140 mg/dL or 7.8 mmol/L; an oral glucose tolerance level (3 hour test) of >95 mg/dL or >5.2 mmol/L; or a combination thereof.

The subject in need thereof may exhibit elevated levels of one or more cytokines (such as TNF-α; IL-6; or IL-1β) compared to an average level of cytokine in a population of subjects under age sixty-five (65). For example, the subject may exhibit an IL-10 level of >227 pg/ml, a TNF-α level of >203 pg/mL, an IL-6 level of >149 pg/mL, or a combination thereof. In certain embodiments, the subject in need thereof may exhibit elevated levels of poly-ubiquitination or FOXO3a compared to an average level of poly-ubiquitination or FOXO3a in a population of subjects under age sixty-five (65).

As described herein, the method include administering a ketogenic supplement to the subject. The ketogenic supplement can include a ketone ester such as R,S-1,3-butanediol diacetoacetate or a derivative thereof. In certain embodiments, the ketogenic supplement can include one or more medium chain triglycerides, beta-hydroxybutyrate, a beta-hydroxybutyrate precursor, an acetoacetate, an acetoacetate precursor, a beta-hydroxybutyrate mineral salt, a beta-hydroxybutyrate amino acid, beta-hydroxybutyrate fatty acid, acetoacetate mineral salt, acetoacetate amino acid, acetoacetate fatty acid, a derivative thereof, or a combination thereof. The ketogenic supplement can be administered in an amount from 5% up to 100% by weight of the subject's diet, such as from 5% up to 85% by weight, from 10% up to 50% by weight, or from 5% up to 30% by weight, of the subject's diet. In some instances, the ketogenic supplement can be administered in an amount from 5% up to 100% of total daily caloric intake (kcal) based on the subject's diet, such as from 10% to 80%, from 5% to 70%, or from 10% to 60% of total daily caloric intake based on the subject's diet. The ketogenic supplement can be administered at about 0.001 g/kg/day to about 10 g/kg/day or about 0.001 g/kg/day to about 5 g/kg/day, based on the subject.

Preferably, administration of the ketogenic supplement to the subject is gradually. For example, the ketogenic supplement can be administered to the subject in an incremental dose elevation of at least 5% by weight of the subject's diet per day (preferably up to 100% by weight of the subject's diet) or at least 10% of the subject's total calorie intake (kcal) per day (preferably up to 100% of the subject's total caloric intake). The ketogenic supplement can be administered to the subject via any suitable means, preferably orally.

Administration of the ketogenic supplement can reduce the levels of insulin-like growth factor-1 (IGF-1), reduce the levels of insulin, elevate the levels of one or more ketone bodies, reduce the levels of blood glucose, or a combination thereof in the subject. Administration of ketogenic supplement can prevent the rise of IGF-1, insulin, and/or blood glucose levels in the subject. Administration of the ketogenic supplement can also reduce the levels of IGF-1 by at least 1.1 fold (such as at least 10, 15, 20, 25, or 30 fold); reduce the levels of insulin by at least 1.1 fold or (such as at least 2, 3, 4, 5, or 6 fold), or a combination thereof in the subject. Administration of the ketogenic supplement can also prevent the elevation of levels of IGF-1 by at least 1.1 fold (such as at least 10, 15, 20, 25, or 30 fold); prevent the elevation of levels of insulin by at least 1.1 fold or (such as at least 2, 3, 4, 5, or 6 fold), or a combination thereof in the subject. Administration of the ketogenic supplement can improve the time to recovery post-infection such as sepsis, septic shock, bacterial infection, inflammatory insult, cytokine storm, or a combination thereof, in the subject.

In addition to the ketogenic supplement, the methods disclosed herein can further comprise administering a second agent selected from the group consisting of an antioxidant, a different anti-aging agent, an anti-inflammatory, a metabolic regulatory agent, or a combination thereof.

Additional advantages will be set forth in part in the description that follows, and in part will be obvious from the description, or may be learned by practice of the aspects described below. The advantages described below will be realized and attained by means of the elements and combinations particularly pointed out in the appended claims. It is to be understood that both the foregoing general description and the following detailed description are exemplary and explanatory only and are not restrictive.

BRIEF DESCRIPTION OF THE FIGURES

For a fuller understanding of the invention, reference should be made to the following detailed description, taken in connection with the accompanying drawings, in which:

FIGS. 1A-B show weekly in vivo IVIS luciferin imaging for representative animal Cancer-Female #3 (CA-F3) in the prone and supine positions, respectively. Primary tumor is visible week 1, subsequent progressive metastases starting week 2 till end of life (EOL). Red line indicates region of interest (ROI). Color Scale/Radiance: 3.62e6-1.21e7 photons/sec/cm$^2$/sr. Data: Experiment 1a. FIG. 1C shows ex vivo anterior and posterior view of CA-F3's organ tissues (liver, spleen, adipose tissue, and primary tumor) via IVIS luciferin imaging indicates metastatic spread. Red line indicates region of interest (ROI). Color Scale/Radiance: 1.06e7-1.51e8 photons/sec/cm$^2$/sr. Data: EOL, Experiment 1a. FIG. 1D shows ex vivo ascites fluid IVIS luciferin imaging shows presence of VM-M3 cells. Red line indicates ROI. Color Scale/Radiance: 1.22e6-1.70e6 photons/sec/cm$^2$/sr. Data: EOL, Experiment 1a. FIG. 1E shows survival curve for Cancer Males (CA-M, n=20) and Females (CA-F, n=18) shows no significant differences. Data: Experiment 1a&b. FIG. 1F shows CA-M (n=12) and CA-F (n=12) data points represent the sum of both prone and supine in vivo bioluminescence for each individual animal. Tumor burden was progressive. Data: Experiment 1a. FIG. 1G shows primary tumor weight progressively increased in both CA-M (Week 1, n=4; Week 2, n=4; Week 3, n=5; EOL, n=11) and CA-F (Week 1, n=4; Week 2, n=5; Week 3, n=6; EOL, n=10) week 1 to EOL. Primary tumor weight at EOL was significantly larger than week 2 and 3 for both CA-M and CA-F. Data: Week 1-3, Experiment 2; EOL, Experiment 1a. FIG. 1H shows whole animal in vivo (n=12/group) and ex vivo IVIS luciferin imaging (Primary Tumor, CA-M n=11, CA-F n=9; Liver, Spleen, CA-M n=12, CA-F n=12; Intraperitoneal Adipose Tissue, CA-M n=12, CA-F n=10; Ascites Fluid, CA-M n=7, CA-F n=5) indicate similar tumor burden. Data: EOL, Whole Animal, Primary Tumor, Liver, Spleen, and Intraperitoneal Adipose Tissue, Experiment 1a; Ascites Fluid, Experiment 1b. Data information: Kaplan-Meier analysis and log-rank test (E). Within group differences across time were analyzed with One-Way ANOVA with Tukey's post-hoc (G). Differences across groups were analyzed with unpaired t-test (G-H). Colors (E-G): CA-M, Blue; CA-F, Red. Data are mean±SEM. $^{ns}$P>0.05, *P<0.05.

FIG. 2A shows Sham Males (SH-M, n=20), Cancer Males (CA-M, n=20), Sham Females (SH-F, n=17), and (D) Cancer Females (CA-F, n=18) bodyweight. Data: Experiment 1a&b. FIG. 2B shows change in bodyweight across groups (SH-M, n=20), (CA-M, n=20), (SH-F, n=17), and (CA-F, n=18). Data: Experiment 1a&b. FIG. 2C shows ascites fluid weight in CA-M (5.5 g, n=8) and CA-F (6.2 g, n=6). Data: EOL, Experiment 1b. FIG. 2D shows gastrocnemius & soleus weights as a ratio baseline bodyweight for SH-M, CA-M (M week 1, n=4; week 2, n=4; week 3, n=5; EOL, n=20), SH-F, CA-F (F week 1, n=5; week 2, n=5; week 3, n=6; EOL, n=17). Data: Week 1-3, Experiment 2; EOL, Experiment 1a&b. FIG. 2E shows quadricep weights as a ratio baseline bodyweight for SH-M, CA-M (M week 1, n=4; week 2, n=4; week 3, n=5; EOL, n=3), SH-F, CA-F (F week 1, n=5; week 2, n=5; week 3, n=6; EOL, n=4). Data: Week 1-3, Experiment 2; EOL, Experiment 1b. FIG. 2F shows intraperitoneal adipose tissue weights as a ratio baseline bodyweight tissue weights for SH-M, CA-M (M week 1, n=4; week 2, n=4; week 3, n=5; EOL, n=8), SH-F, CA-F (F week 1, n=5; week 2, n=5; week 3, n=6; EOL, n=6). Data: Week 1-3, Experiment 2; EOL, Experiment 1b. Data information: Within group differences across time were analyzed with One-Way ANOVA with Tukey's post-hoc (D-F). Differences across groups at each timepoint were analyzed with unpaired t-test (B-F). Colors (D-F): CA-M, Blue; CA-F, Red. Data are mean±SEM. $^{ns}$P>0.05, *P<0.05, P<0.01, *P<0.001, ****P<0.0001.

FIGS. 3A-3F show VM-M3 develop prolonged systemic inflammation. FIG. 3A shows spleen weights as a ratio baseline bodyweight for Sham Males (SH-M), Cancer Males (CA-M) (M week 1, n=4; week 2, n=4; week 3, n=5; end of life, EOL, n=20), Sham Females (SH-F), and Cancer Females (CA-F) (F week 1, n=5; week 2, n=5; week 3, n=6; EOL, n=17). Data: Week 1-3, Experiment 2; EOL, Experiment, 1a&b. FIG. 3B shows primary tumor (n=20), liver (n=24), and spleen (n=24) weight change to bioluminescence ratio via IVIS luciferin imaging. Data: EOL, Experiment 1a. FIG. 3C shows white blood cell count analysis via impedance analysis (SH-M, n=9; SH-F, n=10; CA-M, n=9; CA-F, n=10). Data: EOL, Experiment 1a&b. FIGS. 3D-F show cytokines quantification via Luminex fluorophore intensity analysis (n=9-12/group/timepoint). Data: Experiment 1a. Data information: Within and across group differences were analyzed with One-Way ANOVA with Tukey's post-hoc with >3 comparisons (A) and Fischer LSD post-hoc for <3 comparisons (B, D-F). Differences across groups (A,D-F) or within sexes (C) at each timepoint were analyzed with unpaired t-test. Prior to ANOVA cytokine analysis, robust regression and outlier removal (ROUT) with coefficient Q=1% was used as non-physiologic/error values were detected (D-F). Colors (A, D-F): CA-M, Blue; CA-F, Red. Data are mean±SEM. *P<0.05, P<0.01, *P<0.001, ****P<0.0001.

FIG. 4A shows food Intake was tracked with 4-day average analyzed at end of life (EOL) to baseline (n=12/group). Data: Experiment 1. FIG. 4B shows Hemoglobin (n=10/group), Hematocrit (males n=10/group; females n=9/group), and Red Blood Cell Count (n=10/group) were quantified with impedance analysis. Blood Urea Nitrogen (n=5/group), Total Protein (males n=9/group; females n=5-6/group), and Albumin (males n=5/group; females n=6/group) were analyzed via colorimetry analysis. Data: EOL, Experiment 1a&b. FIG. 4C shows blood glucose, ketones, and lactate were quantified via enzyme interaction (n=8-12/group). Data: Blood Glucose and Ketones, Experiment 1a; Blood Lactate, Experiment 3. Data information: Within group differences across time were analyzed with One-Way ANOVA with Tukey's post-hoc with >3 comparisons (C). Differences across groups (A,C) or within sexes (B) at each timepoint were analyzed with unpaired t-test. Abbreviations: SH-M, Sham Males; CA-M, Cancer Males; SH-F, Sham Females; CA-F, Cancer Females. Colors (C): CA-M, Blue; CA-F, Red. Data are mean±SEM. *P<0.05, P<0.01, *P<0.001, ****P<0.0001.

FIG. 5A shows immunoblotting and quantitative densitometry analysis indicated Poly-Ubiquitination was significantly increased in CA-M compared to SH-M (n=12). Data: Gastrocnemius, EOL, Experiment 1a. FIG. 5B shows immunoblotting and quantitative densitometry analysis indicated 20 S Proteasome Core was not changed in CA-M compared to SH-M (n=12/group). Fluorometric enzymatic assay indicated no change in 20S proteasome capacity (n=12/group). Data: Gastrocnemius, EOL, Experiment 1a. FIG. 5C shows immunoblotting Total and Nuclear Fraction NF-κB (65 kDa), and Ponceau Staining. Densitometry quantification did not indicate altered NF-κB activation between SH-M (n=11) and CA-M (n=12). Data: Gastrocnemius, EOL, Experiment 1a. FIG. 5D shows RT-qPCR analysis of mRNA MyoD in SH-M and CA-M revealed no differences (n=12/group). Data: Gastrocnemius, EOL, Experiment 1a.

FIG. 5E shows RT-qPCR analysis of mRNA MuRF-1, immunoblotting and quantitative densitometry analysis of MuRF-1 in SH-M and CA-M revealed no differences (n=12/group). Data: Gastrocnemius, EOL, Experiment 1a. FIG. 5F shows RT-qPCR analysis of mRNA Atrogin-1, immunoblotting and quantitative densitometry analysis of Atrogin-1 in SH-M and CA-M revealed non-significant elevations (n=12/group). Data: Gastrocnemius, EOL, Experiment 1a. FIG. 5G shows cytokines quantification via Luminex fluorophore intensity analysis (n=7-9/group) indicate elevations in IL-10. Data: Experiment 1a. FIG. 5H shows serum hormone levels quantified via Luminex xMAP fluorophore intensity analysis demonstrated 26-fold reduction in Insulin-like Growth Factor-1 (IGF-1) and 4.5-fold reduction in Insulin in CA-M compared to SH-M (n=11/group). Data: Week 3, Experiment 4c. FIG. 5I shows immunoblotting and quantitative densitometry analysis indicated Nuclear Fraction FOXO3a was significantly increased (2.4-fold) in CA-M (n=12) compared to SH-M (n=11). Data: Gastrocnemius, EOL, Experiment 1a. Data information: Within group differences across time were analyzed with One-Way ANOVA with Fischer LSD post-hoc for <3 comparisons (G). Differences across groups at each timepoint were analyzed with unpaired t-test (A-I). Prior to ANOVA cytokine analysis, robust regression and outlier removal (ROUT) with coefficient Q=1% was used as non-physiologic/error values were detected (G). Colors (G): CA-M, Blue. Data are mean±SEM. ⁿˢP>0.05, P<0.01, **P<0.0001.

FIG. 6A shows food intake was tracked daily and compared across groups. (n=3/group; group=cage; 3-4 animals/cage). Data: Experiment 4c. FIG. 6B shows Blood Ketones, Glucose, and Lactate were quantified for Ketone Diester+VM-M3 Cancer Anorexia Cachexia Syndrome (KDE+VM-M3, n=12), VM-M3 (n=12), and Sham (n=11) via enzyme interaction. KDE+VM-M3 demonstrated shifts in system metabolism. Data: Experiment 4c. FIG. 6C shows KDE+VM-M3 (n=12) and VM-M3 (n=12) data points represent the average of both prone and supine in vivo bioluminescence for each individual animal. KDE+VM-M3 has non-significant reductions in tumor burden. Data: Experiment 4c. FIG. 6D shows ascites fluid weight in KDE+VM-M3 (1.9 g, n=11), VM-M3 (3.0 g, n=11), and Sham (0 g, n=11). Data: Week 3, Experiment 4c. FIG. 6E shows daily bodyweight for KDE+VM-M3 (n=12), VM-M3 (n=12), and Sham (n=11). VM-M3 and Sham saw an increase in bodyweight compared to KDE-VM-M3, starting day 14. Data: Experiment 4c. FIG. 6F shows serum hormone levels quantified via Luminex fluorophore intensity analysis demonstrated significant reductions in Insulin-like Growth Factor-1 (IGF-1) and Insulin in KDE-VM-M3 (n=12) and VM-M3 (n=11) compared to SH-M (n=11). Data: Week 3, Experiment 4c. FIG. 6G shows cardiac tissue weight set to baseline bodyweight (n=10/group) with no significant difference across groups. Data: Week 3, Experiment 4c. FIG. 6H shows intraperitoneal adipose tissue weight set to baseline bodyweight with significant reductions in KDE+VM-M3 and VM-M3 compared Sham (n=10/group). Data: Week 3, Experiment 4c. FIG. 6I shows Gastrocnemius, Soleus, Quadricep, Tibialis Anterior, and Hind Limb (4 muscle pooled analysis) skeletal muscle weights set to baseline bodyweight showed KDE+VM-M3 attenuated skeletal muscle atrophy across several tissues compared to VM-M3 (n=10/group). Data: Week 3, Experiment 4c. Data information: Differences across groups at each timepoint were analyzed with One-Way ANOVA with Fischer LSD post-hoc for ≤3 comparisons (A, B, E-I) or unpaired t-test for individual comparisons (C, D). Colors (A-C, E): KDE+VM-M3, Green; VM-M3, Blue. Data are mean±SEM. KDE-VM-M3 vs VM-M3 *P<0.05, KDE-VM-M3 vs Sham § P<0.05, VM-M3 vs. ShamYP<0.05 (A, B, E). $^{ns}$P>0.05, *P<0.05, P<0.01, *P<0.001, ****P<0.0001 (C, D, F-I).

FIG. 7A shows blood ketones and glucose were quantified for Ketone Diester (KDE) at 2 mL/kg (n=3), 3 mL/kg (n=2), 4 mL/kg (n=3), 5 mL/kg (n=3) via enzyme interaction. KDE at 4 mL/kg demonstrated shifts in system metabolism. Data: Experiment 5a. FIG. 7B shows percentage bodyweight loss 1-day post administration of 10 mg/kg lipopolysaccharide with either 4 mL water (LPS, n=4) or 4 mL/kg KDE (KDE+LPS, n=5) gavage. Data: Experiment 5b. FIG. 7C shows percentage caloric restriction 1-day post LPS (n=4) or KDE+LPS (n=5). Data: Experiment 5b. FIG. 7D shows percentage bodyweight loss tracked for 13-days following LPS (n=4) or KDE+LPS (n=5). Data: Experiment 5b. FIG. 7E shows time to recovery as time taken to return to baseline bodyweight following LPS (n=4) or KDE+LPS (n=5). Data: Experiment 5b. FIG. 7F shows percentage bodyweight loss in pair-fed animals 1-day post LPS (n=4) or KDE+LPS (n=4). Data: Experiment 5c. Data information: Within group differences compared to timepoint "0" were analyzed with One-Way ANOVA with Fischer LSD post-hoc for ≤3 comparisons (A). Difference across groups were analyzed unpaired (B-D,F). Differences across timepoint were analyzed with paired t-test (E). Colors (D-E): KDE+LPS, Green; LPS, Blue. Data are mean±SEM. 4 mL/kg different from timepoint "0" § P<0.05, 5 mL/kg different from timepoint "0" ¥P<0.05 (A). $^{ns}$P>0.05, *P<0.05, P<0.01, *P<0.001 (B-F).

FIG. 8A shows Sham Males (SH-M), Cancer Males (CA-M), Sham Females (SH-F), Cancer Females (CA-F) bodyweight (SH-M, n=20; CA-M, n=20; SH-F, n=18; CA-F, n=18), age (SH-M, n=20; CA-M, n=20; SH-F, n=18; CA-F, n=18), and daily food intake (SH-M, n=12; CA-M, n=12; SH-F, n=11; CA-F, n=12) were matched at baseline. Data: Bodyweight and Age, Experiment 1a&b; Food Intake, Experiment 1a. FIG. 8B shows Sham Males (SH-M) week 1 (n=4), SH-M week 2 (n=4), SH-M week 3 (n=5), Cancer Males (CA-M) week 1 (n=4), CA-M week 2 (n=4), CA-M week 3 (n=5), SH-F week 1 (n=5), SH-F week 2 (n=5), and SH-F week 3 (n=6), Cancer Females (CA-F) week 1 (n=5), CA-F week 2 (n=5), CA-F week 3 (n=6) were similar in bodyweight and age, although females tended to smaller. No significant differences in food intake were observed between CA-F or SH-F except between SH-F week 3 and CA-F week 3. Differences were observed across male groups and CA-F week 2 & 3. Data: Experiment 2. FIG. 8C shows Mean Survival for CA-M (n=20, 31.3 days) and CA-F (n=18, 32.3 days). Data: EOL, Experiment 1a&b. Data information: Differences across groups at each timepoint were analyzed with One-Way ANOVA with Tukey's post-hoc (A,B). Differences across groups were analyzed with unpaired t-test (C). Data are mean±SEM. $^{ns}$P>0.05, *P<0.05, P<0.01, **P<0.0001.

FIG. 9A shows liver weights as a ratio baseline bodyweight for Sham Males (SH-M), Cancer Males (CA-M) (M week 1, n=4; week 2, n=4; week 3, n=5; end of life, EOL, n=20), Sham Females (SH-F), and Cancer Females (CA-F) (F week 1, n=5; week 2, n=5; week 3, n=6; EOL, n=17). Data: Week 1-3, Experiment 2; EOL, Experiment 1a&b. FIG. 9B shows cytokines quantification via Luminex fluorophore intensity analysis (n=8-12/group/time-point). Data: Week 1-3, Experiment 2; EOL, Experiment 1a. Data information: Within group differences across time were analyzed with One-Way ANOVA with Tukey's post-hoc with >3 comparisons (A) and Fischer LSD post-hoc for ≤3 comparisons (B). Differences across groups at each time-point were analyzed with unpaired t-test. (A,B) Prior to ANOVA cytokine analysis, robust regression and outlier removal (ROUT) with coefficient Q=1% was used as non-physiologic/error values were detected (B). Abbreviations: IP-10, IFN-γ-Inducible Protein 10; KC, Keratinocyte-Derived Cytokine; MIG, Monokine Induced by IFN-γ. Colors (A-B): CA-M, Blue; CA-F, Red. Data are mean±SEM. *P<0.05, P<0.01, *P<0.001, ****P<0.0001.

FIGS. 12A-12I show serum and skeletal muscle molecular dynamics. FIG. 12A shows RT-qPCR analysis of mRNA GPR109a in Sham Males (SH-M) and Cancer Males (CA-M) revealed no differences (n=12/group). Data: Gastrocnemius, EOL, Experiment 1a. FIG. 12B shows total RNA was quantified via UV Spectroscopy and was significantly reduced in CA-M compared to SH-M (n=12). Data: Gastrocnemius, EOL, Experiment 1a. FIG. 12C shows BCA colorimetric assay indicated Nuclear Fraction Total Protein was significantly reduced in CA-M (n=10) compared to SH-M (n=12). Data: Gastrocnemius, EOL, Experiment 1a. FIG. 12D shows Immunoblotting Ubiquitination and Ponceau Staining. Data: Gastrocnemius, EOL, Experiment 1a. FIG. 12E shows Immunoblotting 20S Proteasome Core (30 kDa) and Ponceau Staining. Data: Gastrocnemius, EOL, Experiment 1a. FIG. 12F shows Immunoblotting Total NF-κB (65 kDa) and Ponceau Staining. Data: Gastrocnemius, EOL, Experiment 1a. FIG. 12G shows Immunoblotting Cytosolic and Nuclear OGG1 confirming nuclear fractionation. Immunoblotting Nuclear Fraction Total NF-κB (65 kDa) and FOXO3a (73 kDa), and Ponceau Staining. SH-M10 not analyzed due to tissue limitation. Data: Gastrocnemius, EOL, Experiment 1a. FIG. 12H shows Immunoblotting MuRF-1 (43 kDa) and Ponceau Staining. Data: Gastrocnemius, EOL, Experiment 1a. FIG. 12I shows Immunoblotting Atrogin-1 (40 kDa) and Ponceau Staining. Data: Gastrocnemius, EOL, Experiment 1a. Data information: Within group differences across time were analyzed with One-Way ANOVA with Fischer LSD post-hoc for ≤3 comparisons (A). Differences across groups at each timepoint were analyzed with unpaired t-test (A-D). Prior to ANOVA cytokine analysis, robust regression and outlier removal (ROUT) with coefficient Q=1% was used as non-physiologic/error values were detected (A). Abbreviations: OGG1, 8-Oxoguanine-DNA Glycosylase 1. Data are mean±SEM. $^{ns}$P>0.05, *P<0.05, ***P<0.001.

FIG. 13A shows baseline food intake, bodyweight, and age (n=12/group). Data: Experiment 4c. FIG. 13B shows bodyweight tracked daily with step-wise increase in KDE indicating tolerability of 30% KDE incorporated with highly palatable standard diet (HPSD) (n=4). Data: Experiment 4b. FIG. 13C shows Blood Glucose and Ketones were quantified via enzyme interaction for animals fed 20% (n=5), 25% (n=3), 30% (n=5) Ketone Diester (KDE) on top of standard diet. 30% KDE induced largest alterations in systemic metabolism. Data: Experiment 4a. Data information: Across group differences were analyzed with One-Way ANOVA with Fischer LSD post-hoc for ≤3 comparisons (A, C). Differences within groups (C) at each timepoint were analyzed with unpaired t-test. Differences compared to Day 0 were compared with One-Way ANOVA with Dunnett post hoc (B). Colors (C): Post-KDE, Green. Data are mean±SEM. *P<0.05, P<0.01, *P<0.001, ****P<0.0001.

FIG. 14A shows baseline bodyweight for animals prior to administration of 10 mg/kg lipopolysaccharide with either 4 mL water (LPS, n=4) or 4 mL/kg KDE (KDE+LPS, n=5) gavage. Data: Experiment 5b. FIG. 14B shows baseline bodyweight for animals prior to administration of 10 mg/kg lipopolysaccharide with LPS (n=4) or KDE+LPS (n=4) gavage and pair-feeding. Data: Experiment 5c. Data information: Difference across groups were analyzed with unpaired t-test for individual comparisons (A-B). Data are mean±SEM. $^{ns}$P>0.05.

DETAILED DESCRIPTION

Figures 1A, 1B, 1C, 1D:
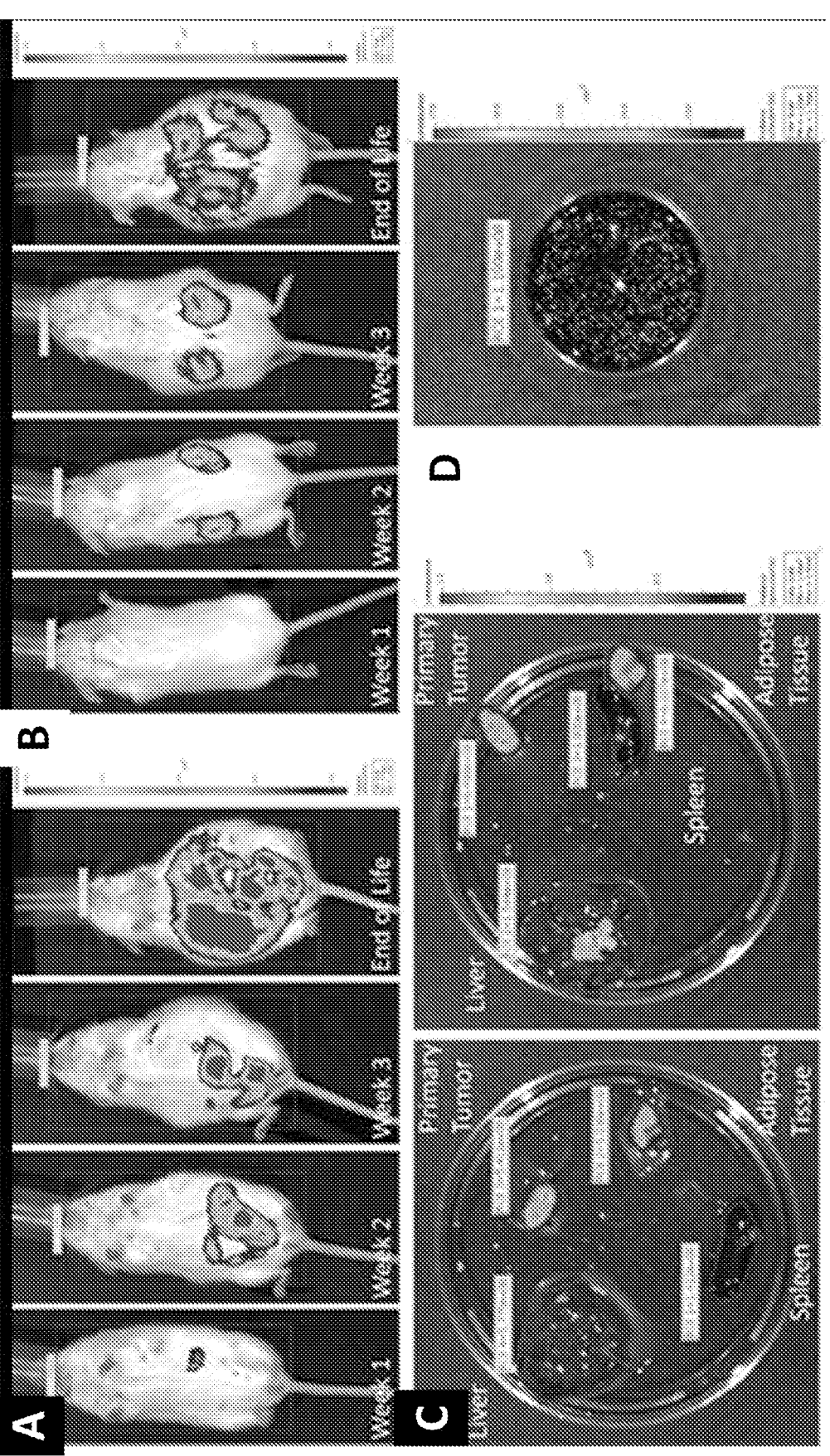
FIGS. 1A-1H show VM-M3 presents with progressive tumor growth and spontaneous systemic metastases.
Figures 1E, 1F, 1G, 1H:
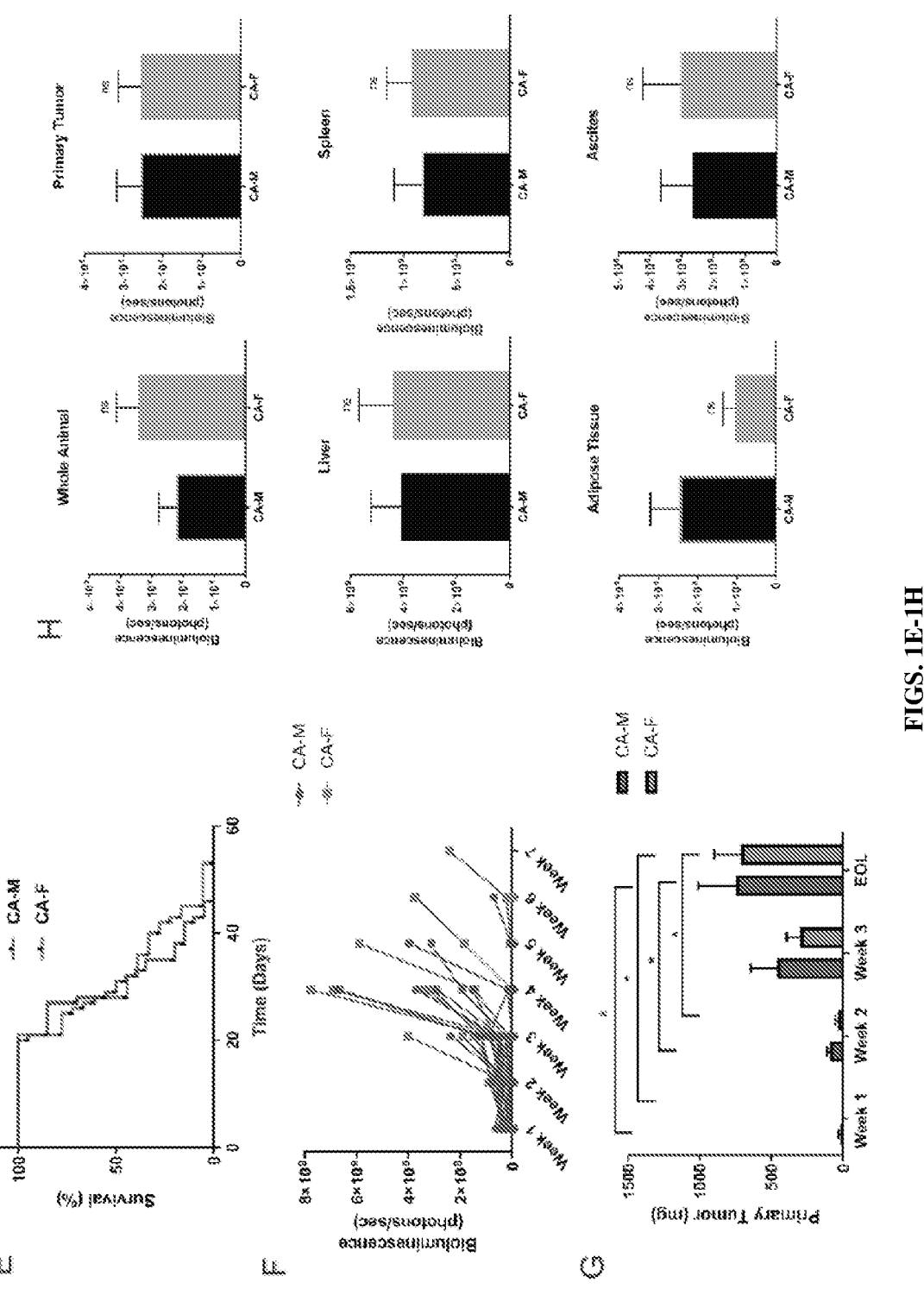

The materials, compounds, compositions, and methods described herein may be understood more readily by reference to the following detailed description of specific aspects of the disclosed subject matter, the Figures, and the Examples included therein.

Before the present materials, compounds, compositions, and methods are disclosed and described, it is to be understood that the aspects described below are not limited to specific synthetic methods or specific reagents, as such may, of course, vary. It is also to be understood that the terminology used herein is for the purpose of describing particular aspects only and is not intended to be limiting.

Also, throughout this specification, various publications are referenced. The disclosures of these publications in their entireties are hereby incorporated by reference into this application in order to more fully describe the state of the art to which the disclosed matter pertains. The references disclosed are also individually and specifically incorporated by reference herein for the material contained in them that is discussed in the sentence in which the reference is relied upon.

General Definitions

In this specification and in the claims that follow, reference will be made to a number of terms, which shall be defined to have the following meanings:

Throughout the specification and claims the word "comprise" and other forms of the word, such as "comprising"

and "comprises," means including but not limited to, and is not intended to exclude, for example, other additives, components, integers, or steps.

As used in the description and the appended claims, the singular forms "a," "an," and "the" include plural referents unless the context clearly dictates otherwise. Thus, for example, reference to "a composition" includes mixtures of two or more such compositions, reference to "an ingredient" includes mixtures of two or more such ingredients, reference to "the supplement" includes mixtures of two or more such supplements, and the like.

"Optional" or "optionally" means that the subsequently described event or circumstance can or cannot occur, and that the description includes instances where the event or circumstance occurs and instances where it does not.

Notwithstanding that the numerical ranges and parameters setting forth the broad scope of the disclosure are approximations, the numerical values set forth in the specific examples are reported as precisely as possible. Any numerical value, however, inherently contain certain errors necessarily resulting from the standard deviation found in their respective testing measurements. Furthermore, when numerical ranges of varying scope are set forth herein, it is contemplated that any combination of these values inclusive of the recited values may be used. Further, ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint. Unless stated otherwise, the term "about" means within 5% (e.g., within 2% or 1%) of the particular value modified by the term "about."

Concentrations, amounts, solubilities, and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "about 1 to about 5" should be interpreted to include not only the explicitly recited values of about 1 to about 5, but also include the individual values and sub-ranges within the indicated range. Thus, included in this numerical range are individual values such as 2, 3, and 4 and sub-ranges such as from 1-3, from 2-4 and from 3-5, etc. This same principle applies to ranges reciting only one numerical value. Furthermore, such an interpretation should apply regardless of the range or the characteristics being described.

By "reduce" or other forms of the word, such as "reducing" or "reduction," is meant lowering of an event or characteristic (e.g., time to recovery). It is understood that this is typically in relation to some standard or expected value, in other words it is relative, but that it is not always necessary for the standard or relative value to be referred to. For example, "reduce time to recover" means decreasing the amount of time to recover from an infection, for example, relative to a standard or a control.

By "prevent" or other forms of the word, such as "preventing" or "prevention," is meant to stop a particular event or characteristic, to stabilize or delay the development or progression of a particular event or characteristic, or to minimize the chances that a particular event or characteristic will occur. Prevent does not require comparison to a control as it is typically more absolute than, for example, reduce. As used herein, something could be reduced but not prevented, but something that is reduced could also be prevented. Likewise, something could be prevented but not reduced, but something that is prevented could also be reduced. It is understood that where reduce or prevent are used, unless specifically indicated otherwise, the use of the other word is also expressly disclosed.

As used herein, "treat", "treatment", "treating", and the like refer to acting upon a condition (e.g., a condition associated with elevated levels of insulin-like growth factor-1 or) with an agent (e.g., ketogenic supplementation) to affect the condition by improving or altering it. The improvement or alteration may include an improvement in symptoms or an alteration in the physiologic pathways associated with the condition. The aforementioned terms cover one or more treatments of a condition in a patient (e.g., a mammal, typically a human or non-human animal of veterinary interest), and includes: (a) reducing the risk of occurrence of the condition in a subject determined to be predisposed to the condition but not yet diagnosed, (b) impeding the development of the condition, and/or (c) relieving the condition, e.g., causing regression of the condition and/or relieving one or more condition symptoms (e.g., reduction in IGF-1 levels or increase in red blood cells).

The term "patient" preferably refers to a human in need of prevention or treatment of effects due to aging or associated disease. In some aspects, the patient can be a human subject age sixty-five or older. In certain aspects, the patient can be a human subject age thirty-five to sixty-four years of age. However, in some aspects of the methods described herein, such as methods for preventing, treating, or reducing time to recovery from a disease, the methods are not limited with respect to the age of the subject. The term "patient" can also refer to non-human animals, preferably mammals such as dogs, cats, horses, cows, pigs, sheep and non-human primates, among others, that are in need of prevention or treatment of effects due to aging or associated disease. The term "patient" is used interchangeably with the term "subject."

As used herein, the term "composition" is intended to encompass a product comprising the specified ingredients in the specified amounts, as well as any product which results, directly or indirectly, from combination of the specified ingredients in the specified amounts.

As used herein "beta-hydroxybutyrate," also known as PHB or BHB, is a carboxylic acid having the general formula $CH_3CHOHCH_2COOH$ which may be utilized by a patient's body as a fuel source during instances of low glucose levels in the patient and is considered a ketone body. In the present disclosure, salt, amino acid, and fatty acid variants of beta-hydroxybutyrate are disclosed.

"Ketosis" as used herein refers to a subject having blood ketone levels within the range of about 0.5 mmol/L and about 16 mmol/L. Ketone levels sustained above 0.5 mmol/L and ideally 1 mmol/L or greater, 1.5 mmol/L or greater, 2 mmol/L or greater, 2.5 mmol/L or greater, in the range of 1.0 to 8.0 mmol/L, from 1.5 to 6.0 mmol/L, or from 1.0 to 3.0 mmol/L appear to offer the most therapeutic effects in humans. Ketosis may improve mitochondrial function, elevate Krebs cycle intermediates (e.g., succinate, fumarate), decrease ROS production, reduce or prevent muscle wasting or atrophy, reduce inflammation, elevate adenosine, increase the activity of neurotrophic factors associated, upregulate the ubiquitin proteasome degradation pathway in association with reduced IGF-1/insulin and increased FOXO3a activation, shift systemic metabolism, and attenuate tumor burden indices, adipose tissue wasting, systemic inflammation, anorexia, anemia, hypoalbuminemia, elevated protein breakdown, or metabolic derangement.

As used herein, the terms "up-regulation" and "down-regulation" generally refer to the expression of one or more genes and the proteins encoded by those genes in response to several signals or conditions Refers to an increase or decrease, respectively. With particular reference to aging biomarkers, upregulation and downregulation refer to such an increase or decrease, respectively, as a function of age.

As used herein, "aging" refers to the accumulation of changes that occur over time in a living organism. Such changes can range from changes that affect genetic and cellular functions to changes that affect the function of an organ, organ system or whole organism. Aging in particular refers to changes that occur after an organism has reached biological maturity and can progress to the final death of the organism. The term "associated with aging" or "aging effects" refer herein specifically to age-related changes in genetic function, such as changes in transcription of individual genes and changes in transcription profiles of genes. "Aging biomarker" refers to genes or groups of genes and their transcripts whose expression is found consistently with age-related changes. Such genes and gene groups can be referred to as "genetic biomarkers", while transcripts can be referred to as "transcription biomarkers."

The term "administration" or "administering" is used to describe the process in which individual ketone supplements such as ketone esters, including R,S-1, 3-butanediol acetoacetate diester and butanediol, R,S-1,3-butanediol, beta-hydroxybutyrate, beta-hydroxybutyrate precursors, beta-hydroxybutyrate mineral salts, beta-hydroxybutyrate amino acid, beta- hydroxybutyrate fatty acid, one or more medium chain triglycerides, acetoacetate, acetoacetate precursors, acetoacetate mineral salts, acetoacetate amino acids, acetoacetate fatty acids, or derivatives thereof, in any combination are delivered to a subject. The composition can be administered in various ways as further described herein, including oral, intragastric, and parenteral (referring to intravenous and intra-arterial and other appropriate parenteral routes), topical, in the form of a foodstuff, among others. Each of these conditions can be readily treated using other administration routes of ketone supplements to treat or prevent a disease or condition.

Administration will often depend upon the amount of compound administered, the number of doses, and duration of treatment. In an embodiment, multiple doses of the agent are administered. The frequency of administration of the agent can vary depending on any of a variety of factors, such as timing of treatment from previous treatments, objectives of the treatment, i.e., reduction and/or prevention of effects of aging or associated disease, and the like. The duration of administration of the agent, e.g., the period of time over which the agent is administered, can vary, depending on any of a variety of factors, including patient response, desired effect of treatment, etc.

The term "therapeutically effective amount" as used herein describes concentrations or amounts of components such as agents which are effective for producing an intended result, including reduction or prevention of effects of aging or associated disease. Compositions as disclosed herein can be used to effect a favorable change in the patient's biochemical parameters, whether that change is an improvement, relieving to some extent one or more of the symptoms of the condition being treated, and/or that amount that will prevent, to some extent, one or more of the symptoms of the condition that the host being treated has or is at risk of developing, or a complete cure of the disease or condition treated. A therapeutically effective amount can be administered in one or more doses.

Therapeutically effective amounts of a compound or composition described herein for treating a mammalian subject can include about 0.1 to about 10000 mg/Kg of body weight of the subject/day, such as from about 1 to about 10000 mg/Kg/day, especially from about 10 to about 10000 mg/Kg/day, or from about 10 to about 5000 mg/Kg/day. The doses can be acute or chronic. A broad range of disclosed composition dosages are believed to be both safe and effective. The amount of the agent contacted (e.g., administered) can vary according to factors such as the degree of susceptibility of the individual, the age, sex, and weight of the individual, idiosyncratic responses of the individual, the dosimetry, and the like. Detectably effective amounts of the agent of the present disclosure can also vary according to instrument and film-related factors. Optimization of such factors is well within the level of skill in the art, unless otherwise noted.

A "pharmaceutically acceptable excipient," "pharmaceutically acceptable diluent," "pharmaceutically acceptable carrier," or "pharmaceutically acceptable adjuvant" means an excipient, diluent, carrier, and/or adjuvant that are useful in preparing a pharmaceutical composition that are generally safe, non-toxic and neither biologically nor otherwise undesirable, and include an excipient, diluent, carrier, and adjuvant that are acceptable for veterinary use and/or human pharmaceutical use. "A pharmaceutically acceptable excipient, diluent, carrier and/or adjuvant" as used in the specification and claims includes one or more such excipients, diluents, carriers, and adjuvants.

Throughout this disclosure reference to a compound with stereocenters that does not specify a specific stereochemistry is meant to include specific reference to each enantiomer, diastereomer, mesocompound, and racemic and scalemic mixtures thereof.

Reference will now be made in detail to specific aspects of the disclosed materials, compounds, compositions, articles, and methods, examples of which are illustrated in the accompanying Examples and Figures.

Preventing, reducing, delaying, or reversing effects due to aging or preventing, treating, or reducing time to recovery from a disease associated with aging is critical for one's health, quality of life, and survival. As evidenced by the following studies, ketone supplementation was determined herein to be a potent defensive agent against diseases including anemia, hypoalbumnemia, hypocholesterolemia, inflammation, malnutrition/anorexia/starvation, spenomegaly, elevated cytokines, Foxo3a or polyubiquitination, or combinations thereof, as well as attenuate effects of aging and associated diseases.

Compositions

Compositions for treating or preventing effects of aging and associated diseases are provided herein. The compositions can comprise a ketogenic supplement in a pharmaceutically acceptable carrier. The amount of ketogenic supplement in the disclosed compositions can be from 1% to 99% by weight of the disclosed compositions, e.g., the ketogenic supplement can be from 1, 5, 10, 15, 20, 25, 30, 35, 40, 45, 50, 55, 60, 65, 70, 75, 80, 85, 90, 95, or 99% of the composition by weight, where any of the stated values can form an upper or lower endpoint of a range. Likewise the pharmaceutically acceptable carrier can be from 1% to 99% by weight of the disclosed compositions, e.g., the pharmaceutically acceptable carrier can be from 1, 5, 10, 15, 20, 25, 30, 35, 40, 45, 50, 55, 60, 65, 70, 75, 80, 85, 90, 95, or 99% of the composition by weight, where any of the stated values can form an upper or lower endpoint of a range.

In other examples, the ketogenic supplement can be one or more compounds chosen from acetoacetate, acetoacetate precursor, 1,3-butanediol, 1,3-butanediol acetoacetate monoester, 1,3-butanediol acetoacetate diester, one or more medium chain triglycerides, beta-hydroxybutyrate, beta-hydroxybutyrate precursor, beta-hydroxybutyrate mineral salt, beta-hydroxybutyrate amino acid, beta-hydroxybutyrate fatty acid, acetoacetate mineral salt, acetoacetate amino acid, acetoacetate fatty acid, derivatives thereof, or combinations thereof. In a specific example, the ketogenic supplement is a ketone ester such as R,S-1,3-butanediol diacetoacetate or a derivative thereof. In specific examples, the ketogenic supplement is R,S-1,3-butandiol, R,S-1,3-butanediol acetoacetate diester, or a combination of the two. The amount of these ketogenic supplements in the disclosed compositions can be at least 0.001 g, e.g., from 0.001 g to 300 g, e.g., 0.001 g or greater, 0.005 g or greater, 0.01 g or greater, 0.05 g or greater, 0.1 g or greater, 0.5 g or greater, 1 g or greater, 10 g or greater, 20 g or greater, 30 g or greater, 40 g or greater, 50 g or greater, 60 g or greater, 70 g or greater, 80 g or greater, 90 g or greater, 100 g or greater, 200 g or greater, or 300 g where any of the stated values can form an upper or lower endpoint of a range. Further, the amount of ketogenic supplement in the disclosed compositions can be an amount sufficient to provide from 0.5 g to 300 g, from 1 g to 40 g, from 5 g to 30 g, or from 10 g to 20 g of ketogenic supplement to a patient. In other examples, the ketogenic supplement can be present in the composition at 0.5 g or less, 1 g or less, 2 g or less, 4 g or less, 5 g or less, 6 g or less, 7 g or less, 8 g or less, 9 g or less, 10 g or less, 11 g or less, 12 g or less, 13 g or less, 14 g or less, 15 g or less, 17 g or less, 19 g or less, 20 g or less, 22 g or less, 24 g or less, 26 g or less, 28 g or less, 30 g or less, 32 g or less, 34 g or less, 36 g or less, 38 g or less, 40 g or less, 42 g or less, 44 g or less, 46 g or less, 48 g or less, 50 g or less, 52 g or less, 54 g or less, 56 g or less, 58 g or less, 60 g or less, 62 g or less, 64 g or less, 66 g or less, 68 g or less, 70 g or less, 72 g or less, 74 g or less, 76 g or less, 78 g or less, 80 g or less, 82 g or less, 84 g or less, 86 g or less, 88 g or less, 90 g or less, 92 g or less, 94 g or less, 96 g or less, 98 g or less, 100 g or less, 200 g or less, or 300 g or less. Alternatively, the ketogenic supplement can be present in the composition in an amount sufficient to provide from 0.001 g to 20 g per kg of patient, from 0.001 g to 10 g per kg of patient, from 0.001 g to 5 g per kg of patient, from 0.01 g to 10 g per kg of patient, from 0.01 g to 5 g per kg of patient, from 0.1 g to 10 g per kg of patient, from 0.1 g to 5 g per kg of patient, or from 5 g to 10 g per kg of patient.

In some examples, the ketogenic supplement includes a medium chain triglyceride (MCTs), monoglycerides, diglycerides, alkyl esters, or free acids thereof. Non-limiting examples and sources of the medium chain triglycerides include coconut oil, coconut milk powder, fractionated coconut oil, palm oil, palm kernel oil, triglycerides of caproic acid, triglycerides of caprylic acid, triglycerides of capric acid, and any combination thereof. The amount of these MCTs in the disclosed compositions can be from 0.001 g to 100 g, e.g., 0.001 g or greater, 0.005 g or greater, 0.01 g or greater, 0.05 g or greater, 0.1 g or greater, 0.5 g or greater, 1 g or greater, 10 g or greater, 20 g or greater, 30 g or greater, 40 g or greater, 50 g or greater, 60 g or greater, 70 g or greater, 80 g or greater, 90 g or greater, 100 g or greater, 200 g or greater, or 300 g, where any of the stated values can form an upper or lower endpoint of a range. Further, the amount of MCTs in the disclosed compositions can be an amount sufficient to provide from 0.001 g to 300 g, from 1 g to 40 g, from 5 g to 30 g, or from 10 g to 20 g of ketogenic supplement to a patient. In other examples, the MCTs can be present in the composition at 0.001, 0.005. 0.01. 0.05, 0.1, 0.5 g or less, 1 g or less, 2 g or less, 4 g or less, 5 g or less, 6 g or less, 7 g or less, 8 g or less, 9 g or less, 10 g or less, 11 g or less, 12 g or less, 13 g or less, 14 g or less, 15 g or less, 17 g or less, 19 g or less, 20 g or less, 22 g or less, 24 g or less, 26 g or less, 28 g or less, 30 g or less, 32 g or less, 34 g or less, 36 g or less, 38 g or less, 40 g or less, 42 g or less, 44 g or less, 46 g or less, 48 g or less, 50 g or less, 52 g or less, 54 g or less, 56 g or less, 58 g or less, 60 g or less, 62 g or less, 64 g or less, 66 g or less, 68 g or less, 70 g or less, 72 g or less, 74 g or less, 76 g or less, 78 g or less, 80 g or less, 82 g or less, 84 g or less, 86 g or less, 88 g or less, 90 g or less, 92 g or less, 94 g or less, 96 g or less, 98 g or less, 100 g or less, 200 g or less, or 300 g or less. Alternatively, the MCTs can be present in the composition in an amount sufficient to provide from 0.001 g to 20 g per kg of patient, from 0.001 g to 10 g per kg of patient, from 0.001 g to 5 g per kg of patient, from 0.01 g to 10 g per kg of patient, from 0.01 g to 5 g per kg of patient, from 0.1 g to 10 g per kg of patient, from 0.1 g to 5 g per kg of patient, or from 5 g to 10 g per kg of patient.

In some examples, the ketone supplement does not contain a beta-hydroxybutyrate, abeta-hydroxybutyrate precursors such as monoester of beta-hydroxybutyrate, beta-hydroxybutyrate mineral salts, beta-hydroxybutyrate amino acid, beta- hydroxybutyrate fatty acid, one or more medium chain triglycerides, acetoacetate, acetoacetate precursors, acetoacetate mineral salts, acetoacetate amino acids, acetoacetate fatty acids, or glycerol.

The ketogenic supplements disclosed herein can be formulated according to known methods for preparing pharmaceutically acceptable compositions. Formulations are described in detail in a number of sources which are well known and readily available to those skilled in the art. For example, Remington's Pharmaceutical Science by E.W. Martin (1995) describes formulations that can be used in connection with the disclosed methods. In general, the compounds disclosed herein can be formulated such that an effective amount of the ketogenic supplement is combined with a pharmaceutically acceptable carrier in order to facilitate effective administration of the compound. The resulting compositions used can also be in a variety of forms. These include, for example, solid, semi-solid, and liquid dosage forms, such as tablets, pills, powders, liquid solutions or suspension, suppositories, injectable and infusible solutions, and sprays. The preferred form depends on the intended mode of administration and therapeutic application. The compositions also include conventional pharmaceutically-acceptable carriers, which are known to those skilled in the art. Examples of carriers for use with the disclosed compositions compounds include water, milk, juice, ethanol, dimethyl sulfoxide, glycerol, alumina, starch, saline, and equivalent carriers.

In a specific example, the disclosed compositions comprise a ketogenic supplement (e.g., R,S 1,3-butanediol acetoacetate diester, MCTs, or combinations thereof) and a liquid pharmaceutical carrier, such as water, fruit juice, or milk.

The compositions disclosed herein can further comprises an antioxidant, a different anti-aging agent, an anti-inflammatory, a metabolic regulatory agent, vitamins (e.g., Vitamin A, Vitamin B6, Vitamin B12, Vitamin C, Vitamin D, Vitamin E) and/or minerals (e.g., potassium, calcium, magnesium, chromium, selenium), proteins, essential amino acids, branch chain amino acids, amino acids, or derivatives, which can be co-administered with ketone supplementation.

In further examples, disclosed herein are foodstuffs that comprise a ketogenic supplement. For example, disclosed are snack foods, nutritional bars, protein bars, beverages that comprise a ketogenic supplement (e.g., R,S 1,3-butanediol acetoacetate diester, MCTs, or combinations thereof). Ketone diester can be composed with protein, amino acids, or derivative of these combinations.

Methods

Aging is a common and gradually decreasing process of the function of various organs in the body. Many physiological factors play an important role in aging, and several genes and gene products that act as biomarkers for aging or associated diseases can be identified. The expression of specific genes and groups of genes is sometimes found to change dramatically depending on the age of the organism. Certain biomarkers of aging can depend on the organism. That is, the identity of genes that exhibit age-related effects can vary from species to species. Furthermore, the identity of biomarkers and the degree of age-related effects on the expression of each biomarker can vary between biological tissue types. For example, a gene or group of genes, gene products, epigenetic, or related changes can be a consistent biomarker of aging in muscle tissue, but not so much age-related effects in brain tissue and no age-related effects in other tissues.

The effect of aging on gene expression depends in part on the gene itself, in particular the function associated with the gene. Thus, in some genes, expression is upregulated with age, while in other expressions, down-regulation is found with age. In addition, the degree of up- or down-regulation observed can vary from gene or gene product to gene or gene product, some showing dramatic changes, while others show less but still significant changes. By example, insulin like growth factor (IGF) is a kind of natural growth hormone, which plays an important role in growth and development of the body and is important in aging. Secretion of growth hormone (GH), and consequently that of insulin-like growth factor 1 (IGF-1), declines over time until only low levels can be detected in individuals aged≥60 years. By contrast, several mutations that decrease the tone of the GH/IGF-1 axis are associated with extended longevity. Pharmaceutically inhibiting IGF-1 has been associated with delaying ageing and age-related disease or disorders. Moreover, subjects with reduced activity of IGF-1 are protected from age-related diseases such as cancer and diabetes mellitus, two major ageing-related morbidities.

Disclosed herein are methods for preventing, reducing, delaying, or reversing effects due to aging in a subject in need thereof. Further disclosed are methods for preventing, treating, or reducing time to recovery from a disease in a subject. In some embodiments of the methods for preventing, treating, or reducing time to recovery from a disease, the disease can be associated with aging. The ageing process is not uniform across population due to differences in genetics, lifestyle, and overall health. For the purposes described herein, in the methods for preventing, treating, or reducing time to recovery from a disease associated with aging, the subject may be age sixty-five (65) or over. In the methods for reversing effects due to aging, the subject can be age sixty-five (65) or over. In the methods for preventing, reducing or delaying effects due to aging, the subject can be age thirty-five (35) or over, such as age 35-64, but preferably age sixty-five (65) or over. In certain embodiments, the subject can be a female age fifty-five (55) or older or a male age sixty-five (65) or over. As discussed herein, however, in some aspects of the methods, the methods are not limited with respect to the age of the subject.

As described herein, several genes and gene products that act as biomarkers for aging or associated diseases can be identified. Methods for determining aging biomarkers in an organism are known, such as a comprehensive gene expression profile can be obtained by monitoring mRNA for synonymous genes using a high-density oligonucleotide array. This approach can be used to identify genetic bio-markers and to quantify age-related effects. In certain embodiments, the subject in need thereof may exhibit elevated levels of insulin-like growth factor-1 (IGF-1), insulin, or a combination thereof, compared to an average level of IGF-1 or insulin in a population of subjects under age sixty-five (65). For example, the subject may exhibit a fasting insulin level of >4.9 μU/mL; IGF-1 level of >150 ng/ml; HOMA1-IR level of ≥2.5; HOMA2-IR level of >1.4; HbA1c level of >5.6% or 38 mmol/mol; fasting blood glucose level of >99 mg/dL; oral glucose tolerance level (1 hour test) of >140 mg/dL or 7.8 mmol/L; oral glucose tolerance level (3 hour test) of >95 mg/dL or >5.2 mmol/L; or a combination thereof.

In certain embodiments, the subject in need thereof may exhibit elevated levels of one or more cytokines (such as TNF-α; IL-6; or IL-1β) compared to an average level of cytokine in a population of subjects under age sixty-five (65). For example, the subject may exhibit an IL-10 level of >227 pg/ml, a TNF-α level of >203 pg/mL, an IL-6 level of >149 pg/mL, or a combination thereof. In certain embodiments, the subject in need thereof may exhibit elevated levels of poly-ubiquitination or FOXO3a compared to an average level of poly-ubiquitination or FOXO3a in a population of subjects under age sixty-five (65).

As described herein, methods for preventing, treating, or reducing time to recovery from a disease are provided. In some embodiments, the subject in need thereof has a disease such as anemia, hypoalbuminemia, hypocholesterolemia, inflammation, malnutrition/anorexia/starvation, splenomegaly, or a combination thereof. The subject may have a disease associated with elevated levels of insulin-like growth factor-1 (IGF-1), insulin, or a combination thereof; elevated levels of one or more cytokines (such as TNF-α; IL-6; or IL-1β); elevated levels of poly-ubiquitination or FOXO3a; or a combination thereof.

The inventors have found that the compositions disclosed herein are effective in preventing, reducing, delaying, or reversing effects due to aging or preventing, treating, or reducing time to recovery from a disease associated with aging, or preventing, treating, or reducing anemia, hypoal-bumnemia, hypocholesterolemia, inflammation, malnutrition/anorexia/starvation, splenomegaly, elevated cytokines, elevated foxo3a, and elevated poly-ubiquitination. In certain embodiments, in genes or gene products that exhibit age-related upregulation, the compositions may prevent, reduce or reverse the upregulation. In another embodiment, the compositions may prevent, reduce or reverse age-related downregulation in genes or gene products that exhibit such downregulation. In certain embodiments, an oral composition can include a ketogenic supplement selected to prevent, reduce, delay, reverse effects due to aging or prevent, treat, or reduce time to recovery from a disease, in a number of different tissues. In another embodiment, the methods of preventing, reducing, delaying, or reversing effects due to aging or preventing, treating, or reducing time to recovery from a disease in a subject comprise administering a therapeutically effective amount of a ketogenic supplement to the subject.

An effective amount of the composition can be administered to the subject. In some embodiments, the ketogenic supplement is administered in an amount up to 100% by weight of the subject's diet, such as from 5% up to 100% by weight, from 10% up to 100% by weight, from 15% up to 100% by weight, from 20% up to 100% by weight, from 5% up to 80% by weight, from 10% up to 80% by weight, from 15% up to 80% by weight, from 20% up to 80% by weight, from 5% up to 50% by weight, from 10% up to 50% by weight, from 15% up to 50% by weight, from 20% up to 50% by weight, from 5% up to 30% by weight, from 10% up to 30% by weight, or from 15% up to 30% by weight, of the subject's diet. In some embodiments, the ketogenic supplement is administered in an amount up to 100% total daily caloric intake based on the subject's diet, such as from 5% up to 100% of total daily caloric intake (kcal), from 10% up to 100% of total daily caloric intake, from 15% up to 100% of total daily caloric intake, from 20% up to 100% of total daily caloric intake, from 30% up to 100% of total daily caloric intake, from 5% up to 80% of total daily caloric intake, from 10% up to 80% of total daily caloric intake, from 15% up to 80% of total daily caloric intake, from 20% up to 80% of total daily caloric intake, from 30% up to 80% of total daily caloric intake, from 5% up to 60% of total daily caloric intake, from 10% up to 60% of total daily caloric intake, from 15% up to 60% of total daily caloric intake, from 20% up to 60% of total daily caloric intake, from 30% up to 60% of total daily caloric intake, from 5% up to 50% of total daily caloric intake, from 10% up to 50% of total daily caloric intake, from 15% up to 50% of total daily caloric intake, from 20% up to 50% of total daily caloric intake, or from 30% up to 50% of total daily caloric intake, based on the subject's diet.

The ketogenic supplement can be administered at about 0.001 g/kg/day to about 10 g/kg/day, such as about 0.01 g/kg/day to about 10 g/kg/day, about 0.1 g/kg/day to about 10 g/kg/day, about 0.001 g/kg/day to about 8 g/kg/day, about 0.01 g/kg/day to about 8 g/kg/day, about 0.1 g/kg/day to about 8 g/kg/day, about 0.5 g/kg/day to about 8 g/kg/day, about 1 g/kg/day to about 8 g/kg/day, about 0.001 g/kg/day to about 5 g/kg/day, about 0.01 g/kg/day to about 5 g/kg/day, about 0.1 g/kg/day to about 5 g/kg/day, about 0.5 g/kg/day to about 5 g/kg/day, about 1 g/kg/day to about 5 g/kg/day, about 0.001 g/kg/day to about 3 g/kg/day, about 0.01 g/kg/day to about 3 g/kg/day, about 0.1 g/kg/day to about 3 g/kg/day, about 0.5 g/kg/day to about 3 g/kg/day, or about 1 g/kg/day to about 3 g/kg/day, based on the subject.

Preferably, administration of the ketogenic supplement to the subject is gradually. For example, the ketogenic supplement can be administered to the subject in an incremental dose elevation of at least 5 by weight of the subject's diet per day (preferably up to 100% by weight, up to about 80% by weight, up to about 60% by weight, up to about 50% by weight, or up to about 30% by weight, of the subject's diet). The ketogenic supplement can be administered to the subject in an incremental dose elevation of at least 10% total calorie intake per day of the subject's diet (preferably up to 100% of total caloric intake, up to 80% of total caloric intake, up to 60% of total caloric intake, up to 50% of total caloric intake, or up to 40% of total caloric intake).

In vivo application of the ketogenic supplement and compositions containing them, can be accomplished by any suitable method and technique presently or prospectively known to those skilled in the art. For example, the ketogenic supplement can be formulated in a physiologically- or pharmaceutically-acceptable form and administered by any suitable route known in the art including, for example, oral, nasal, rectal, topical, and parenteral routes of administration. As used herein, the term parenteral includes subcutaneous, intradermal, intravenous, intramuscular, intraperitoneal, and intrasternal administration, such as by injection. Administration of the disclosed compounds or compositions can be a single administration, or at continuous or distinct intervals as can be readily determined by a person skilled in the art.

The compounds disclosed herein, and compositions comprising them, can also be administered utilizing liposome technology, slow release capsules, implantable pumps, and biodegradable containers. These delivery methods can, advantageously, provide a uniform dosage over an extended period of time. The compounds can also be administered in their salt derivative forms or crystalline forms.

The compounds disclosed herein can be formulated according to known methods for preparing pharmaceutically acceptable compositions. Formulations are described in detail in a number of sources which are well known and readily available to those skilled in the art. For example, *Remington's Pharmaceutical Science* by E.W. Martin (1995) describes formulations that can be used in connection with the disclosed methods. In general, the compounds disclosed herein can be formulated such that an effective amount of the compound is combined with a suitable carrier in order to facilitate effective administration of the compound. The compositions used can also be in a variety of forms. These include, for example, solid, semi-solid, and liquid dosage forms, such as tablets, pills, powders, liquid solutions or suspension, suppositories, injectable and infusible solutions, and sprays. The preferred form depends on the intended mode of administration and therapeutic application. The compositions also preferably include conventional pharmaceutically-acceptable carriers and diluents which are known to those skilled in the art. Examples of carriers or diluents for use with the compounds include ethanol, dimethyl sulfoxide, glycerol, alumina, starch, saline, and equivalent carriers and diluents. To provide for the administration of such dosages for the desired therapeutic treatment, compositions disclosed herein can advantageously comprise between about 0.1% and 99%, and especially, 1 and 15% by weight of the total of one or more of the subject compounds based on the weight of the total composition including carrier or diluent.

Formulations suitable for administration include, for example, aqueous sterile injection solutions, which can contain antioxidants, buffers, bacteriostats, and solutes that render the formulation isotonic with the blood of the intended recipient; and aqueous and nonaqueous sterile suspensions, which can include suspending agents and thickening agents. The formulations can be presented in unit-dose or multi-dose containers, for example sealed ampoules and vials, and can be stored in a freeze dried (lyophilized) condition requiring only the condition of the sterile liquid carrier, for example, water for injections, prior to use. Extemporaneous injection solutions and suspensions can be prepared from sterile powder, granules, tablets, etc. It should be understood that in addition to the ingredients particularly mentioned above, the compositions disclosed herein can include other agents conventional in the art having regard to the type of formulation in question.

Compounds disclosed herein, and compositions comprising them, can be delivered to a cell either through direct contact with the cell or via a carrier means. Carrier means for delivering compounds and compositions to cells are known in the art and include, for example, encapsulating the composition in a liposome moiety. Another means for delivery of compounds and compositions disclosed herein to a cell comprises attaching the compounds to a protein or nucleic acid that is targeted for delivery to the target cell. U.S. Pat. No. 6,960,648 and U.S. Application Publication Nos. 20030032594 and 20020120100 disclose amino acid sequences that can be coupled to another composition and that allows the composition to be translocated across biological membranes. U.S. Application Publication No. 20020035243 also describes compositions for transporting biological moieties across cell membranes for intracellular delivery. Compounds can also be incorporated into polymers, examples of which include poly (D-L lactide-co-glycolide) polymer for intracranial tumors; poly[bis(p-carboxyphenoxy) propane:sebacic acid]in a 20:80 molar ratio (as used in GLIADEL); chondroitin; chitin; and chitosan.

Therapeutic application of compounds and/or compositions containing them can be accomplished by any suitable therapeutic method and technique presently or prospectively known to those skilled in the art. Further, compounds and compositions disclosed herein have use as starting materials or intermediates for the preparation of other useful compounds and compositions.

Compounds and compositions disclosed herein can be locally administered at one or more anatomical sites, optionally in combination with a pharmaceutically acceptable carrier such as an inert diluent. Compounds and compositions disclosed herein can be systemically administered, such as intravenously or orally, optionally in combination with a pharmaceutically acceptable carrier such as an inert diluent, or an assimilable edible carrier for oral delivery. They can be enclosed in hard or soft shell gelatin capsules, can be compressed into tablets, or can be incorporated directly with the food of the patient's diet. For oral therapeutic administration, the active compound can be combined with one or more excipients and used in the form of ingestible tablets, buccal tablets, troches, capsules, elixirs, suspensions, syrups, wafers, aerosol sprays, and the like.

The tablets, troches, pills, capsules, and the like can also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring can be added. When the unit dosage form is a capsule, it can contain, in addition to materials of the above type, a liquid carrier, such as a vegetable oil or a polyethylene glycol. Various other materials can be present as coatings or to otherwise modify the physical form of the solid unit dosage form. For instance, tablets, pills, or capsules can be coated with gelatin, wax, shellac, or sugar and the like. A syrup or elixir can contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound can be incorporated into sustained-release preparations and devices.

Compounds and compositions disclosed herein, including pharmaceutically acceptable salts, hydrates, or analogs thereof, can be administered intravenously, intramuscularly, or intraperitoneally by infusion or injection. Solutions of the active agent or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations can contain a preservative to prevent the growth of microorganisms.

The pharmaceutical dosage forms suitable for injection or infusion can include sterile aqueous solutions or dispersions or sterile powders comprising the active ingredient, which are adapted for the extemporaneous preparation of sterile injectable or infusible solutions or dispersions, optionally encapsulated in liposomes. The ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. Optionally, the prevention of the action of microorganisms can be brought about by various other antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the inclusion of agents that delay absorption, for example, aluminum monostearate and gelatin.

Sterile injectable solutions are prepared by incorporating a compound and/or agent disclosed herein in the required amount in the appropriate solvent with various other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, compounds and agents disclosed herein can be applied in as a liquid or solid. However, it will generally be desirable to administer them topically to the skin as compositions, in combination with a dermatologically acceptable carrier, which can be a solid or a liquid. Compounds and agents and compositions disclosed herein can be applied topically to a subject's skin to reduce the size (and can include complete removal) of malignant or benign growths, or to treat an infection site. Compounds and agents disclosed herein can be applied directly to the growth or infection site. Preferably, the compounds and agents are applied to the growth or infection site in a formulation such as an ointment, cream, lotion, solution, tincture, or the like. Drug delivery systems for delivery of pharmacological substances to dermal lesions can also be used, such as that described in U.S. Pat. No. 5,167,649.

Useful solid carriers include finely divided solids such as talc, clay, microcrystalline cellulose, silica, alumina and the like. Useful liquid carriers include water, alcohols or glycols or water-alcohol/glycol blends, in which the compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers, for example.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user. Examples of useful dermatological compositions which can be used to deliver a compound to the skin are disclosed in U.S. Pat. Nos. 4,608,392; 4,992,478; 4,559,157; and 4,820,508.

Useful dosages of the compounds and agents and pharmaceutical compositions disclosed herein can be determined by comparing their in vitro activity, and in vivo activity in animal models. Methods for the extrapolation of effective dosages in mice, and other animals, to humans are known to the art; for example, see U.S. Pat. No. 4,938,949.

Pharmaceutical compositions that comprise a ketogenic supplement in combination with a pharmaceutically acceptable carrier are disclosed herein. Pharmaceutical compositions adapted for oral, topical or parenteral administration, comprising an amount of a compound constitute a preferred aspect. The dose administered to a patient, particularly a human, should be sufficient to achieve a therapeutic response in the patient over a reasonable time frame, without lethal toxicity, and preferably causing no more than an acceptable level of side effects or morbidity. One skilled in the art will recognize that dosage will depend upon a variety of factors including the condition (health) of the subject, the body weight of the subject, kind of concurrent treatment, if any, frequency of treatment, therapeutic ratio, as well as the severity and stage of the pathological condition.

In further embodiments, the ketone compounds described herein may be formulated in the form of a foodstuff, for example a snack food, nutritional bar, protein bar, or beverage that comprises a therapeutically effective amount of a ketone compounds described herein (for example, R,S-1,3-butanediol acetoacetate).

In the disclosed methods, the ketogenic supplement can be administered on a regimen of 1 to 6 times per day, such as once or twice per day, or continuously. This dosing regimen can be adjusted to provide the optimal therapeutic response. Ketogenic supplement can be administered prior, during or post to disease or disorder initiation, or independent of disease or disorder state. Ketone supplements can be administered topically. It can be co-administered with glucose, fructose, sucralose, galactose or derivative thereof, or protein, essential amino acids, branch chain amino acids, amino acids, derivatives thereof.

In any of the disclosed methods herein the ketogenic supplement can be administered with a standard diet, e.g., without restrictions as to glucose intake. For example, the ketogenic supplement can be administered while the subject is fed ad libitum.

Administration of the ketogenic supplement can reduce the levels of insulin-like growth factor-1 (IGF-1), reduce the levels of insulin, elevate the levels of one or more ketone bodies, reduce the levels of blood glucose, or a combination thereof in the subject. Administration of the ketogenic supplement can also reduce the levels of IGF-1 by at least 1.1 fold (such as by at least 10, at least 15, at least 20, at least 25, or at least 30 fold); reduce the levels of insulin by at least 1.1 fold or (such as at least 2, at least 3, at least 4, at least 5, or at least 6 fold), or a combination thereof in the subject.

Administration of ketogenic supplement can prevent the rise of IGF-1, insulin and/or glucose. Administration of the ketogenic supplement can also prevent the elevation of levels of IGF-1 by at least 1.1 fold (such as at least 10, 15, 20, 25, or 30 fold); prevent the elevation of levels of insulin by at least 1.1 fold or (such as at least 2, 3, 4, 5, or 6 fold), or a combination thereof in the subject. Administration of the ketogenic supplement can improve the time to recovery post-infection such as sepsis, septic shock, bacterial infection, inflammatory insult, cytokine storm, or a combination thereof, in the subject. Administration of ketogenic supplement can preventing, treating, or reducing anemia, hypoalbumnemia, hypocholesterolemia, inflammation, malnutrition/anorexia/starvation, splenomegaly, elevated cytokines, elevated foxo3a, and elevated poly-ubiquitination.

In addition to the ketogenic supplement, the methods disclosed herein can further comprise administering a second agent selected from the group consisting of an antioxidant, a different anti-aging agent, an anti-inflammatory, a metabolic regulatory agent, or a combination thereof.

The subject is preferably a human subject.

Kits

Also disclosed are kits that comprise a compound disclosed herein in one or more containers. The disclosed kits can optionally include pharmaceutically acceptable carriers and/or diluents. In one embodiment, a kit includes one or more other components, adjuncts, or adjuvants as described herein. In another embodiment, a kit includes one or more ketogenic supplements. In one embodiment, a kit includes instructions or packaging materials that describe how to administer a compound or composition of the kit. Containers of the kit can be of any suitable material, e.g., glass, plastic, metal, etc., and of any suitable size, shape, or configuration. In one embodiment, a compound and/or agent disclosed herein is provided in the kit as a solid, such as a tablet, pill, or powder form. In another embodiment, a compound and/or agent disclosed herein is provided in the kit as a liquid or solution. In one embodiment, the kit comprises an ampoule or syringe containing a compound and/or agent disclosed herein in liquid or solution form.

Also disclosed herein are kits comprising one or more of the disclosed compounds, and one or more of: a) at least one anti-aging compound, b) instructions for preventing, reducing, delaying, or reversing effects due to aging, or c) instructions for preventing, treating, or reducing time to recovery from a disease.

In some examples, the kit further comprises at least one agent, wherein the compound and the agent are co-formulated.

In some examples, the ketogenic supplements are co-packaged.

The kits can also comprise compounds and/or products co-packaged, co-formulated, and/or co-delivered with other components. For example, a drug manufacturer, a drug reseller, a physician, a compounding shop, or a pharmacist can provide a kit comprising a disclosed compound and/or product and another component for delivery to a patient.

It is contemplated that the disclosed kits can be used in connection with the disclosed methods of making, the disclosed methods of using, and/or the disclosed compositions.

EXAMPLES

The following examples are set forth below to illustrate the methods and results according to the disclosed subject matter. These examples are not intended to be inclusive of all aspects of the subject matter disclosed herein, but rather to illustrate representative methods and results. These examples are not intended to exclude equivalents and variations of the present invention, which are apparent to one skilled in the art.

Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric. There are numerous variations and combinations of reaction conditions, e.g., component concentrations, temperatures, pressures, and other reaction ranges and conditions that can be used to optimize the product purity and yield obtained from the described process. Only reasonable and routine experimentation will be required to optimize such process conditions.

Example 1: Ketone Bodies Attenuate Various Disease Conditions

Methods: A model of systemic metastasis was evaluated for the comprehensive CACS (metastasis, skeletal muscle and adipose tissue wasting, inflammation, anorexia, anemia, elevated protein breakdown, hypoalbuminemia, and metabolic derangement) in both males and females. Ex vivo skeletal muscle analysis was utilized to determine ubiquitin proteasome degradation pathway activation. A ketone diester (R/S 1,3-butanediol acetoacetate diester) was assessed in multifaceted catabolic environments.

Results: In the present example, it was shown that the ubiquitin proteasome degradation pathway was significantly upregulated in association with reduced IGF-1/insulin and increased FOXO3a activation, but not TNF-α-induced NF-κB activation, driving skeletal muscle atrophy. Additionally, it was shown that R/S 1,3-butanediol acetoacetate diester administration shifted systemic metabolism, attenuated tumor burden indices, reduced atrophy/catabolism and mitigated comorbid symptoms in both CACS and cancer-independent atrophy environments.

Methods:

Cell Culture: VM-M3 cells were derived from a spontaneous tumor in a VM/Dk inbred mouse and adapted to cell culture. VM-M3 cells were transduced with a lentivirus vector containing the firefly luciferase gene under control of the cytomegalovirus promoter as previously described. VM-M3 cells were cultured in D-glucose, L-glutamine, and sodium pyruvate-free Dulbecco's Modified Eagle Medium (Gibco, Life Technologies) supplemented with 10% fetal bovine serum (Invitrogen), 25 mM D-glucose (Fisher Scientific), 2 mM L-glutamine (Gibco, Life Technologies), 1% penicillin-streptomycin (Invitrogen), and 10 mM HEPES buffer (Gibco, Life Technologies). Cells were maintained at 37° C. in 95% air, 5% $CO_2$ in a humidified incubator.

Figures 13A, 13B, 13C:
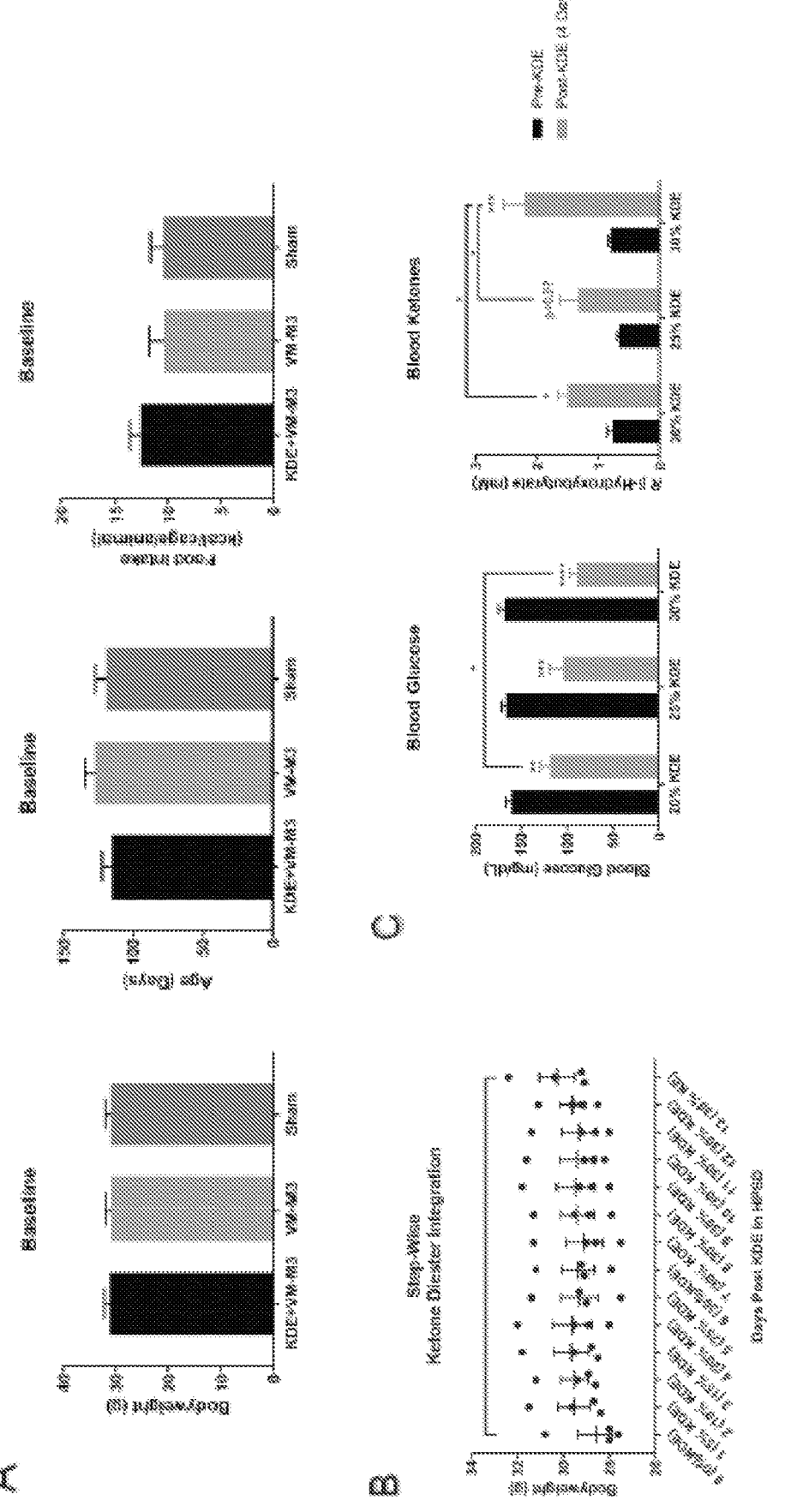
FIGS. 13A-13C show ketone diester food incorporation alters systemic metabolism and is well tolerated.
Figures 14A, 14B:
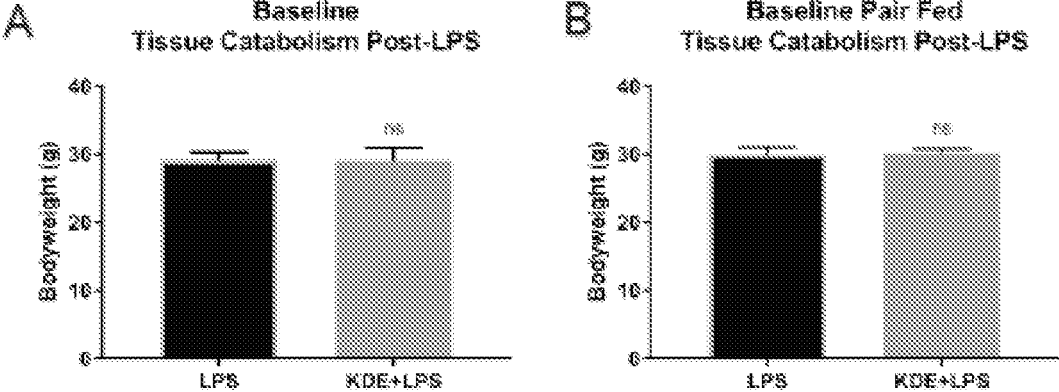
FIGS. 14A-14B show bodyweights were controlled prior to LPS experimentation.

Animals: Five breeding pairs of the VM/Dk strain of mice were used to establish and propagate a VM/Dk mouse colony in the University of South Florida (USF) Morsani College of Medicine Vivarium according to standard husbandry protocol. Male and female VM/Dk mice between 10-23 weeks of age were singly housed to accurately assess individual animal food intake. Bodyweight and food intake were tracked daily prior to and post-social isolation to ensure bodyweight and food intake normalized prior to cell inoculation (Table 1). Animals were distributed into one of four groups: Sham Male (SH-M), Sham Female (SH-F), Cancer Male (CA-M), and Cancer Female (CA-F). Each cancer animal was matched with a sham animal of equivalent sex, bodyweight, age, and food intake (FIGS. 8A-8B) to ensure appropriate cancer and sex-specific comparisons. To determine KDE-induced effects in CACS, VM/Dk animals were distributed into one of three groups: KDE+VM-M3, VM-M3, and Sham with equivalent sex, bodyweight, age and food intake at baseline (FIG. 13A). One premature death occurred in SH-F (Experiment 1a) and Sham (Experiment 4c) groups immediately post-inoculation. To determine KDE-induced effects post-LPS administration, VM/Dk animals were distributed into two groups (FIGS. 14A-14B): KDE+LPS and LPS of equivalent bodyweights. All procedures were approved by the USF Institutional Animal Care and Use Committee (USF IACUC; Protocol Number R1900 & R5829) and performed under strict adherence to the NIH Guide for the Care and Use of Laboratory Animals.

VM-M3 Cell and Lipopolysaccharide Implantation: For VM-M3 implantation in the model characterization experiments (FIG. 1-5; FIG. 8-12), ~1×10$^6$ VM-M3 cells (T. Seyfried, Boston College) in 300 μL sterile PBS (CA-M and CA-F) or 300 μL sterile PBS-only (SH-M and SH-F) were injected subcutaneously into the left abdominal flank resulting in primary tumor formation at the injection site, and subsequently systemically metastasizes to most major organs, namely the liver, kidneys, spleen, lungs, and brain. Additional model analysis revealed metastatic disease and CACS temporal progression could be replicated with intraperitoneal administration of VM-M3 cells. This method of implantation further minimized variability in markers of tumor progression, and therefore provides a useful optional method technique in the VM-M3 model for efficient analysis of potential therapeutic agents. To determine KDE-induced effects on CACS, 1×10$^6$ VM-M3 cells in 300 μL sterile PBS (KDE+VM-M3 and VM-M3) or 300 μL sterile PBS-only (Sham) were administered intraperitoneally (FIG. 6; FIG. 13). For LPS administration in the septic atrophy model, LPS (*Escherichia coli* 055:B5; L2880; Sigma-Aldrich, St. Louis, MO) was diluted in sterile PBS and administered intraperitoneally at 10 mg/kg as pilot work indicated a maximal, yet non-fatal, ~15% bodyweight reduction at 10 mg/kg dose.

Survival Analysis: Animal health and behavior were assessed daily. VM-M3 animals were humanely euthanized together with their sham-matched controls (sex, bodyweight, age, and food intake matched at baseline) by exsanguination under isoflurane (Henry Schein Animal Health, Dublin, OH) according to IACUC guidelines upon presentation of end of life (EOL) defined criteria associated with tumor burden and disease progression (decreased response to stimuli, failure to thrive, labored breathing and/or locomotion, and/or complete cessation of food intake). Survival time was recorded.

Tumor Growth and Metastasis: Tumor growth was monitored weekly as a measure of bioluminescence using the Xenogen IVIS Spectrum system (Caliper LS, Hopkinton, MA). Data acquisition and analysis was performed using the Living Image@ software (Caliper LS). Approximately 15 minutes prior to in vivo imaging, VM/Dk mice received an intraperitoneal injection of D-Luciferin (50 mg/kg; 88293, Thermo Fisher Scientific; Waltham, MA). Bioluminescent signal was obtained using the IVIS Lumina cooled CCD camera system in both prone and supine positions. As only the cancer cells were transfected with the luciferase gene, bioluminescent signal (photons/sec) of the whole animal was measured and tracked over time as an indicator of tumor burden and metastatic spread. At EOL, primary tumor, spleen, liver, and adipose tissue were gathered and saturated with D-Luciferin (10 μL D-Luciferin+PBS/g tissue at 5 mg D-Luciferin/mL PBS dilution) for 5 mins and imaged to determine tumor burden. Ascites fluid was imaged 15 minutes after resuspension with D-Luciferin (20 μL D-Luciferin+PBS/mL ascites fluid at 5 mg D-Luciferin/mL PBS dilution) to assess presence of circulating tumor cells.

Body Composition: Bodyweight was assessed daily at the same time (7:00-9:00 AM). At EOL, bodyweight and weights of ascites fluid, primary tumor, calf (combined gastrocnemius & soleus), anterior thigh (quadriceps), intraperitoneal fat pads, liver and spleen tissue were measured (Table 1; Experiment 1a&b). A follow-up time course experiment was conducted at weeks 1, 2, and 3 to assess weekly changes in bodyweight and aforementioned tissues for both cancer and sham-matched control animals (Experiment 2). For follow up evaluation of KDE in CACS, bodyweight was tracked daily with tissue weight determined at 21-days, prior to EOL (Experiment 4c). All tissue weights were gathered at harvest and normalized to baseline bodyweight (not influenced by cachexia progression) to allow for appropriate comparison between animals. For evaluation of KDE in LPS, bodyweight was tracked daily for evaluation pre- and post-LPS administration (Experiment 5b&c).

Food Intake and Ketone Diester Administration: Standard diet dry food (2018 Teklad Global 18% Protein Rodent Diet, Harlan) was mixed with deionized water (1 g dry food/mL deionized water) into a consistent paste and placed on a 100×15 mm dish. Food intake was tracked daily at the same time (7:00-9:00) and replaced every other day to ensure fresh food. Due to sinusoidal/oscillatory changes in food intake observed every other day (2-day pattern), a 4-day (2×2-day pattern) average was taken at EOL and baseline to calculate changes in anorexic symptoms. KDE was chemically synthesized with physical properties, preparation, and analysis described previously. For evaluation of KDE effect on anorexia, food intake was tracked daily at the same time (7:00-9:00). As pilot work indicated reductions in ad libitum food intake with 20-30% by weight KDE incorporation standard diet, 1%/weight saccharine (Sigma-Aldrich) and 5%/weight peanut butter (Natural Jif Creamy, J. M. Smucker Company, Orrville, OH) were added to paste to increase palatability of standard diet across groups (HPSD). Additional pilot work revealed that incremental incorporation of KDE from 0-30% KDE/weight at 5% KDE/weight/day was better tolerated and did not result in changes in bodyweight across time (FIG. 13B). Consequently, upon VM-M3 inoculation, KDE+VM-M3 received ad libitum 0% KDE/weight day 1, 5% KDE day 2, 10% KDE day 3, 15% KDE day 4, 20% KDE day 5, 25% KDE day 6, and 30% KDE day 7 through 21 on top of HPSD. VM-M3 and Sham received HPSD ad libitum. As pilot work indicated potential water evaporation in food paste in ventilated cages, dehydration standard curve was calculated across various volumes of plated food (5, 10, 25.0, 50.0, 100 g/food) with and without KDE over a two-day period. Standard curve equation [water evaporated=0.2472 (original grams of water)+1.364] was used to correct for amount of dehydration prior to calculating caloric intake. For LPS experiments, 1×4 mL/kg KDE gavage or 1×4 mL/kg water gavage were administered for KDE+LPS and LPS-only, respectively. Ab libitum food intake was tracked daily during initial analysis with caloric restriction reported as the percent reduction in 24-hour caloric intake from pre- to post-LPS administration. Pair-feeding was conducted during subsequent analysis. Pair-feeding was accomplished by measuring the 24-hour caloric intake of LPS-only group and presenting this amount of food to the KDE+LPS group.

Inflammation: Whole blood was gathered at baseline, week 2, and EOL prior to anesthetics exposure via submandibular puncture to prevent anesthetic influence on inflammatory biomarkers and to avoid potential ascites contamination from cardiac puncture. 60 µL of whole blood was placed into a K$_2$EDTA tube (BD Microtainer, Franklin, NJ), relabeled for blinded analysis, and analyzed via HemoTrue (Heska, Loveland, Colorado) to assess white blood cell counts. Remaining whole blood was placed into serum separator tubes (MiniCollect 0.8 mL, Kremsunster, Austria) and centrifuged (13,000 rpm, 4° C., 15 min) to isolate serum. 25 µL of serum was mixed with 25 µL of saline, relabeled for blinded analysis, and analyzed using Bio-Plex (Bio-Rad, Hercules, California) fluorescent bead technology to generate cytokine concentrations via a standard curve (EVE Technology Mouse Cytokine/Chemokine Array 31-Plex). To determine whether spleen or liver enlargement in VM-M3 animals was explained by tumor burden alone or other immunologic factors, tissue bioluminescence was divided by the difference in tissue weight between VM-M3 and sham-matched controls. This bioluminescence to tissue weight ratio for both the liver and spleen was compared to primary tumor to determine if the organ weight differences could be explained by tumor burden alone.

Primary Tumor: Tumor Burden/Organ (mg) =

$$\frac{\text{Primary Tumor Bioluminesence}}{\text{Primary Tumor Weight}}$$

Liver: Tumor Burden/ΔOrgan (mg) =

$$\frac{\text{Liver Bioluminescence}}{(\text{Cancer Burdened Liver Weight} - \text{Sham Liver Weight})}$$

Spleen: Tumor $\frac{\text{Burden}}{\Delta\text{Organ}}$ (mg) =

$$\frac{\text{Spleen Bioluminescence}}{(\text{Cancer Burdened Spleen Weight} - \text{Sham Spleen Weight})}$$

Metabolic Biomarkers: Blood glucose and R β-hydroxybutyrate were measured using Precision Xtra™ Blood Glucose & Ketone Monitoring System (Abbott Laboratories, Abbott Park, IL). Blood lactate concentration was measured using Lactate Plus Lactate Meter (Nova Biomedical). IGF-1 and Insulin were relabeled for blinded analysis and subsequently analyzed using Luminex 100 system (Luminex, Austin, TX) with R&D Systems Mouse 1-Plex Luminex Assay (R&D Systems, Minneapolis, MN) and Milliplex Mouse Multiplex Kit (Millipore, St. Charles, MO), respectively, using manufacturer's protocol.

Clinical Cachexia Biomarker: At EOL, blood was gathered as previously described and red blood cell count relabeled for blinded analysis via HemoTrue (Heska, Loveland, Colorado). Remaining whole blood was centrifuged (13,000 rpm, 4° C., 15 min) down in serum separator tubes, relabeled for blinded analysis (MiniCollect 0.8 mL, Kremsunster, Austria), and analyzed via DRI-CHEM 7000 (Heska) to determine clinical chemistry concentrations.

Muscle Tissue Collection and Processing: Gastrocnemius muscle tissue was immediately gathered, separated and flash frozen in liquid nitrogen and stored at −80° C. at harvest. Prior to tissue processing, all tissues were deidentified and relabeled for blinded analysis. For protein and RNA analyses tissues were removed from −80° C. and crushed using a liquid nitrogen-cooled mortar and pestle. For protein analysis, −30 mg of powdered tissue was placed in 1.7 mL microcentrifuge tubes containing 500µL of ice-cold cell lysis buffer [20 mM Tris-HCl (pH 7.5), 150 mM NaCl, 1 mM Na$_2$EDTA, 1 mM EGTA, 1% Triton (Cell Signaling, Danvers, MA)] pre-stocked with protease and Tyr/Ser/Thr phosphatase inhibitors (2.5 mM sodium pyrophosphate, 1 mM 0-glycerophosphate, 1 mM Na$_3$VO$_4$, 1 µg/mL leupeptin). Samples were then homogenized by hand using tight micropestles, insoluble proteins were removed with centrifugation at 500 g for 5 minutes and obtained sample lysates were stored at −80-C prior to Western blotting and other biochemical assays (described below). For total RNA analysis, ~15-30 mg of powdered tissue was weighed using an analytical scale with a sensitivity of 0.001 g (Mettler-Toledo; Columbus, OH). Tissue was then homogenized in 1.7 mL microcentrifuge tubes containing 500 µL of Ribozol (Ameresco; Solon, OH) via micropestle manipulation and RNA isolation was performed per manufacturer recommendations. Total RNA concentrations were then determined in duplicate using a NanoDrop Lite spectrophotometer (Thermo Fisher Scientific), and total RNA per unit muscle weight was used as a surrogate for ribosome density as in past publications.

Western Blot Analysis: Whole-tissue sample lysates obtained through cell lysis buffer processing (described above) were batch process-assayed for total protein content using a BCA Protein Assay Kit (Thermo Fisher Scientific). Lysates were then prepared for Western blotting using 4× Laemmli buffer at 1 µg/µL. Following sample preparation, 18 µL samples were loaded onto 4-15% SDS polyacrylamide gels (Bio-Rad; Hercules, CA) and subjected to electrophoresis (180V for 45-60 minutes) using premade 1×SDS-PAGE running buffer (Ameresco; Framingham, MA) in order of Sham, then Cancer, from animal number 1 to 12. Proteins were then transferred (200 mA for 2 hours) to polyvinylidene difluoride membranes (Bio-Rad), Ponceau stained and imaged to ensure equal protein loading between lanes. Membranes were then blocked for 1 hour at room temperature with 5% non-fat milk powder in Tris-buffered saline with 0.1% Tween-20 (TBST; Ameresco). Rabbit anti-mouse pan NF-κB/p65 (1:1000; Cell Signaling, catalog #: 8242), rabbit anti-mouse MuRF-1 (1:500; Abcam, Cambridge, MA; catalog #: ab172479), rabbit anti-mouse Atrogin-1 (1:500; Abcam, catalog #: ab74023), rabbit anti-mouse Forkhead-box protein O3a (FOXO3a; 1:500; Cell Signaling, catalog #: 2497), rabbit anti-mouse ubiquitin (1:1,000; catalog #: 3933; Cell Signaling) and rabbit anti-mouse 20S proteasome core (1:500; Millipore Sigma, Burlingame, MA; catalog #: ST1053) were incubated with membranes overnight at 4° C. in TBST with 5% bovine serum albumin (BSA). The following day, membranes were incubated with horseradish peroxidase-conjugated anti-rabbit IgG (1:2000; Cell Signaling; catalog #: 7074; Danvers, MA) in TBST with 5% BSA at room temperature for 1 hour (1:2000). Membrane development was performed using an enhanced chemiluminescent reagent (Luminata Forte HRP substrate; EMD Millipore, Billerica, MA), and band densitometry was performed using a gel documentation system and associated densitometry software (UVP, Upland, CA). Densitometry values for all targets were divided by whole-lane ponceau densities. Density/ponceau were divided by the Sham mean and expressed as relative fold-change relative to the Sham group.

PCR: Two µg of RNA was reverse transcribed into cDNA for RT-PCR analysis with cDNA synthesis reagents (Quanta Biosciences, Gaithersburg, MD) per the manufacturer's recommendations. RT-PCR was performed using gene-specific primers and SYBR green chemistry (Quanta Biosciences). Primer sequences used were as follows: beta-glucuronidase (housekeeping gene, HKG): forward primer 5'-TCAGCTCTGTGACCGATACG-3' [SEQ. ID. NO. 1], reverse primer 5'-GCCACAGACCACATCACAAC-3' [SEQ. ID. NO. 2]; MyoD: forward primer 5'-CCTGCCCTC-CACATCCTTTT-3' [SEQ. ID. NO. 3], reverse primer 5'-GAAGGGGGAGAGTGGGGTAT-3' [SEQ. ID. NO. 4]; Atrogin-1/MAFbx: forward primer 5'-CCATCCTCTTTCTTGCCCGT-3' [SEQ. ID. NO. 5], reverse primer 5'-ATCACTGTCCAACCTGGCTG-3' [SEQ. ID. NO. 6]; MuRF-1: forward primer 5'-TGGGACA-GATGAGGAGGAGG-3' [SEQ. ID. NO. 7], reverse primer 5'-TTTACCCTCTGTGGTCACGC-3' [SEQ. ID. NO. 8]; GPR109a: forward primer 5'-GATGAAAACATCGC-CAAGGT-3' [SEQ. ID. NO. 9], reverse primer 5'-CCTCCAGTCCCAGTTATGGA-3' [SEQ. ID. NO. 10]; IGF-1: forward primer 5'-ACCACCCTGTGACCTCAGTC-3' [SEQ. ID. NO. 11], reverse primer 5'-CTCCTG-GAAACCCAGAACAA-3' [SEQ. ID. NO. 12]. Melt curve analyses confirmed that only one RT-PCR product was obtained with each primer set. PCR calculations were performed as previously described. Briefly, $2^{\Delta Cq}$ values for each gene of interest at each time point were calculated whereby $\Delta Cq$=gene of interest Cq—geometric mean housekeeping gene Cq values. All values for a given mRNA target were then normalized to the Sham mean and expressed as relative fold-change relative to the Sham group.

20S Proteasome Capacity Assay: Skeletal muscle protein from whole-tissue sample lysates (40 µg) obtained through cell lysis buffer processing (described above) were batch processed for 20S proteasome activity using commercially available fluorometric kits (catalog #: APT280; Millipore Sigma; Burlington, MA, United States) as previously described. Assay readings are presented as relative fluorometric units normalized to input muscle protein as determined through the BCA assay described above. The average coefficient of variation for all duplicates was 10.7%.

Statistics: GraphPad Prism 7 software was used for all statistical analysis. Parametric tests were performed for all data sets as all groups were considered normally distributed. Unpaired or paired student's t tests were performed for the comparison of two groups. One-Way ANOVA with Tukey's multiple comparison post-hoc test was performed for more than three comparisons while Fischer LSD post-hoc was used for three comparisons or less. Results were considered significant when p<0.05. Robust regression and outlier removal (ROUT) with coefficient Q=1% was only used prior to cytokine analysis as non-physiologic/error values were independently indicated.

Figure 8A:
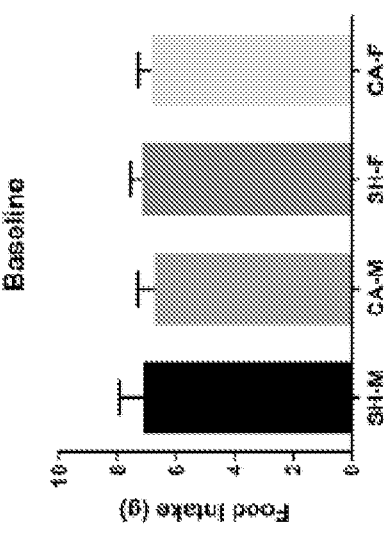
FIGS. 8A-8C show baseline sex, bodyweight, and age controlled with similar survival in males and females.
Figure 8A:
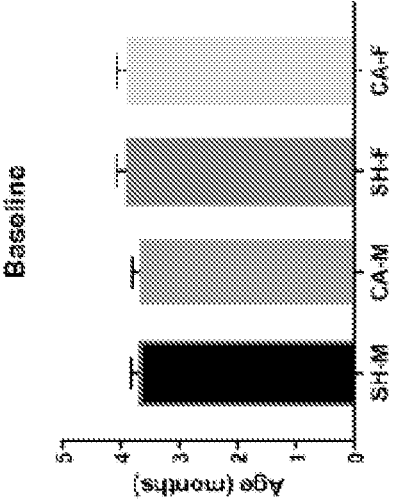
Figure 8A:
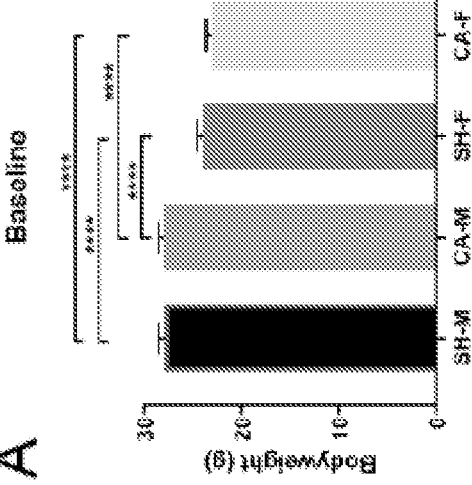
Figure 8B:
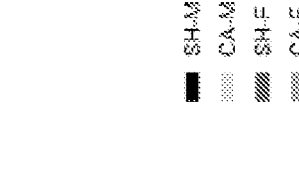
Figure 8B:
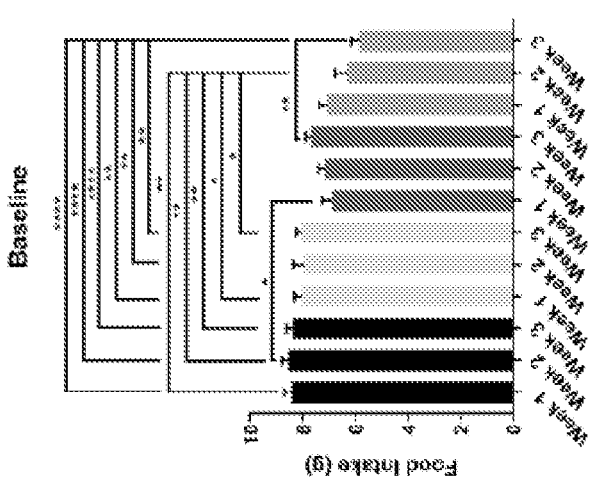
Figure 8B:
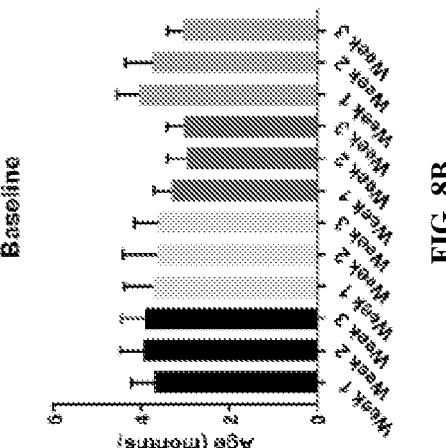
Figure 8B:
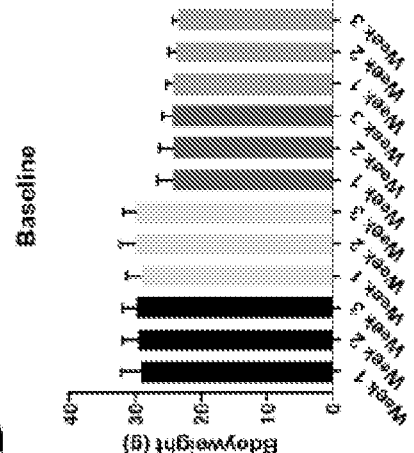
Figure 8C:
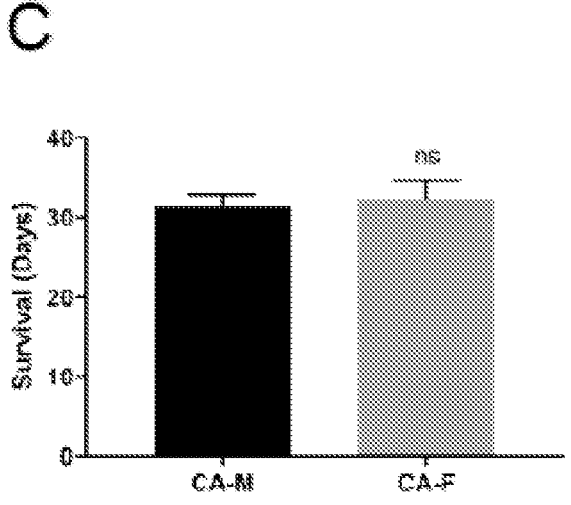
Figure 9A:
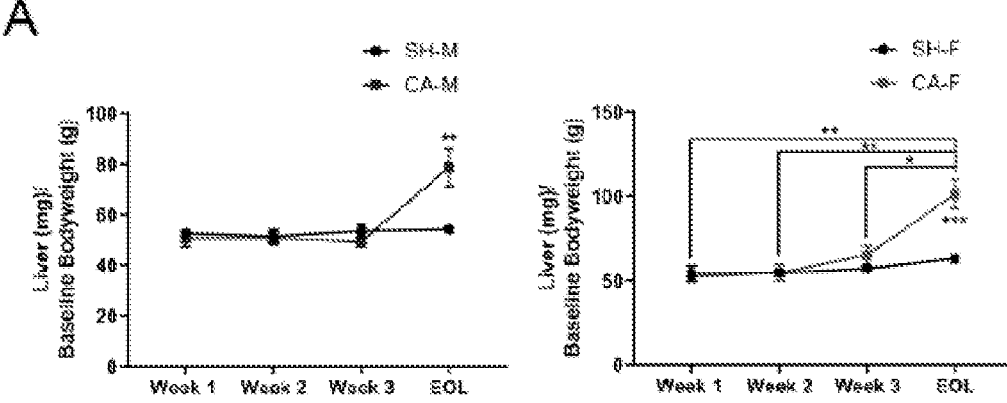
FIGS. 9A-9B show VM-M3 develop prolonged systemic inflammation.
Figure 9B:
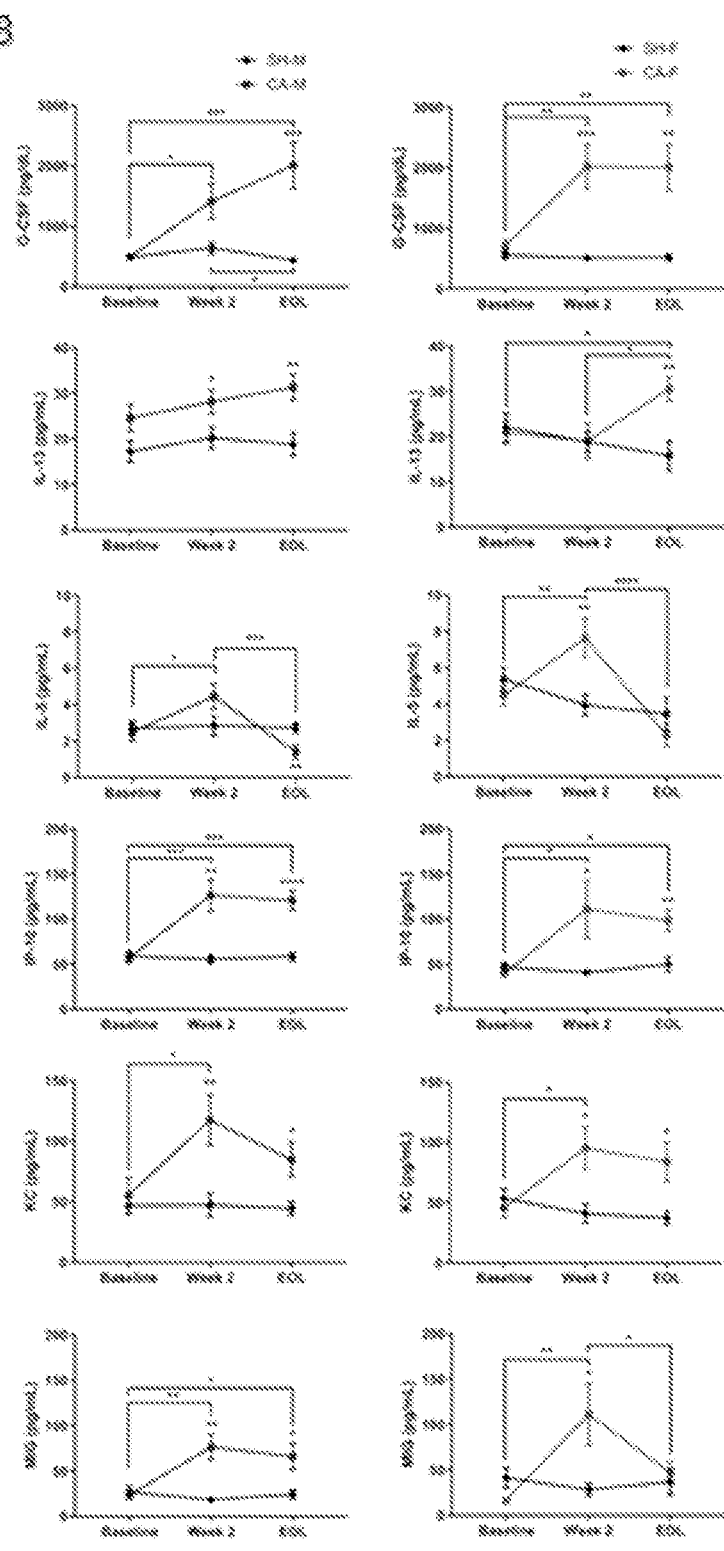

Results:

VM-M3 Presents with Progressive Tumor Growth and Spontaneous Systemic Metastases: Clinical reports consistently indicate that cachexia is most prevalent during metastatic disease. To determine tumor growth rate, metastatic progression and survival specific to cancer and sex in the VM-M3 model, CA-M and CA-F were matched to SH-M and SH-F of equivalent sex, bodyweight, and age (FIG. 8A-B). Following implantation of either $1 \times 10^6$ VM-M3 cells expressing a luciferase reporter or PBS vehicle-only into VM/Dk mice, tumor growth and metastatic spread were tracked weekly. CA-M and CA-F developed a primary tumor at the implantation site by week 1, followed by visible metastatic spread to various tissues from tumor origin (FIG. 1); this was confirmed by ex vivo organ and tissue bioluminescence imaging (FIG. 1C-D, F, H). Primary tumor weight increased progressively from week 1 to EOL (FIG. 1G), with similar metastatic invasion into the liver, spleen, adipose tissue, and ascites fluid (FIG. 1H) between CA-M and CA-F. This is consistent with the progressive nature of systemic metastatic disease, where cachexia and comorbidities are most commonly reported in clinical cancer cachexia. Additionally, survival did not differ between CA-M and CA-F (median: 30 and 28 days, respectively, FIG. 1E; mean: 31.3±1.6 and 32.3±2.4 days, respectively, FIG. 8C) illustrating similar tumor burden, metastatic spread, and survival between sexes.

VM-M3 Develops Skeletal Muscle and Adipose Tissue Wasting Not Represented in Bodyweight Measurements: Skeletal muscle and adipose tissue atrophy are common hallmarks of cancer cachexia. To determine whether the VM-M3 model had progressive tissue atrophy, bodyweight was tracked daily during initial analysis and weekly during subsequent analysis as a superficial marker of body composition (FIG. 2A; Table 1). CA-M and CA-F gained significantly more bodyweight than sham groups (FIG. 2B); however, a characteristic feature of the VM-M3 model upon presentation of widespread metastatic burden is the accumulation of ascites fluid in the intraperitoneal cavity, which contributes to the elevation in bodyweight. This characteristic is also seen in metastatic patients. To address this concern, ascites fluid was weighed at EOL to determine its contribution to bodyweight gain. Ascites fluid accounted for 5.5±1.0 g and 6.3±1.4 g in CA-M and CA-F bodyweights, respectively (FIG. 2C), explaining in part, along with tumor burden, the elevations in bodyweight seen in VM-M3 animals.

Figure 2A:
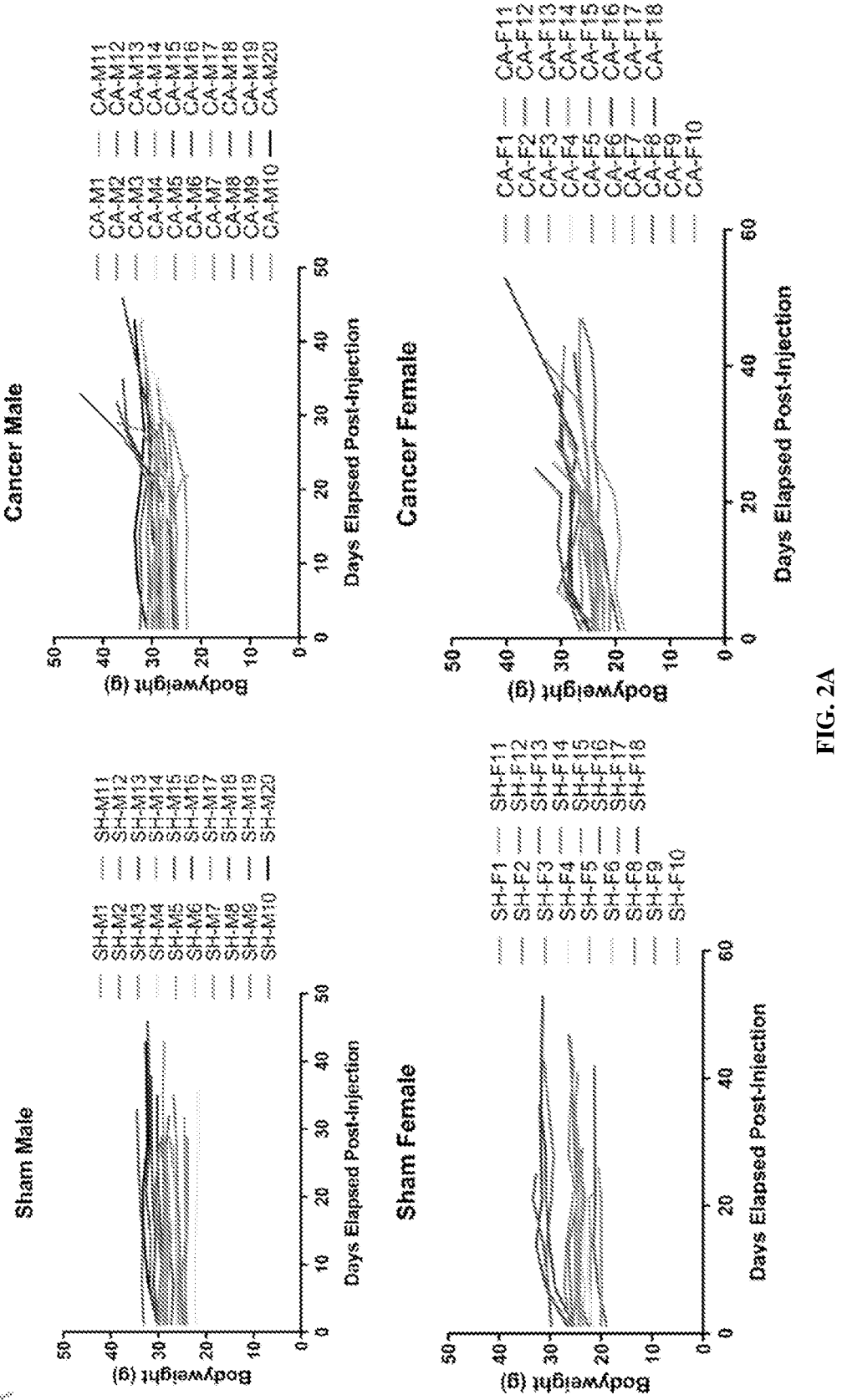
FIGS. 2A-2F show VM-M3 develop skeletal muscle and adipose tissue wasting not represented in bodyweight measurements.
Figures 2B, 2C, 2D, 2E, 2F:
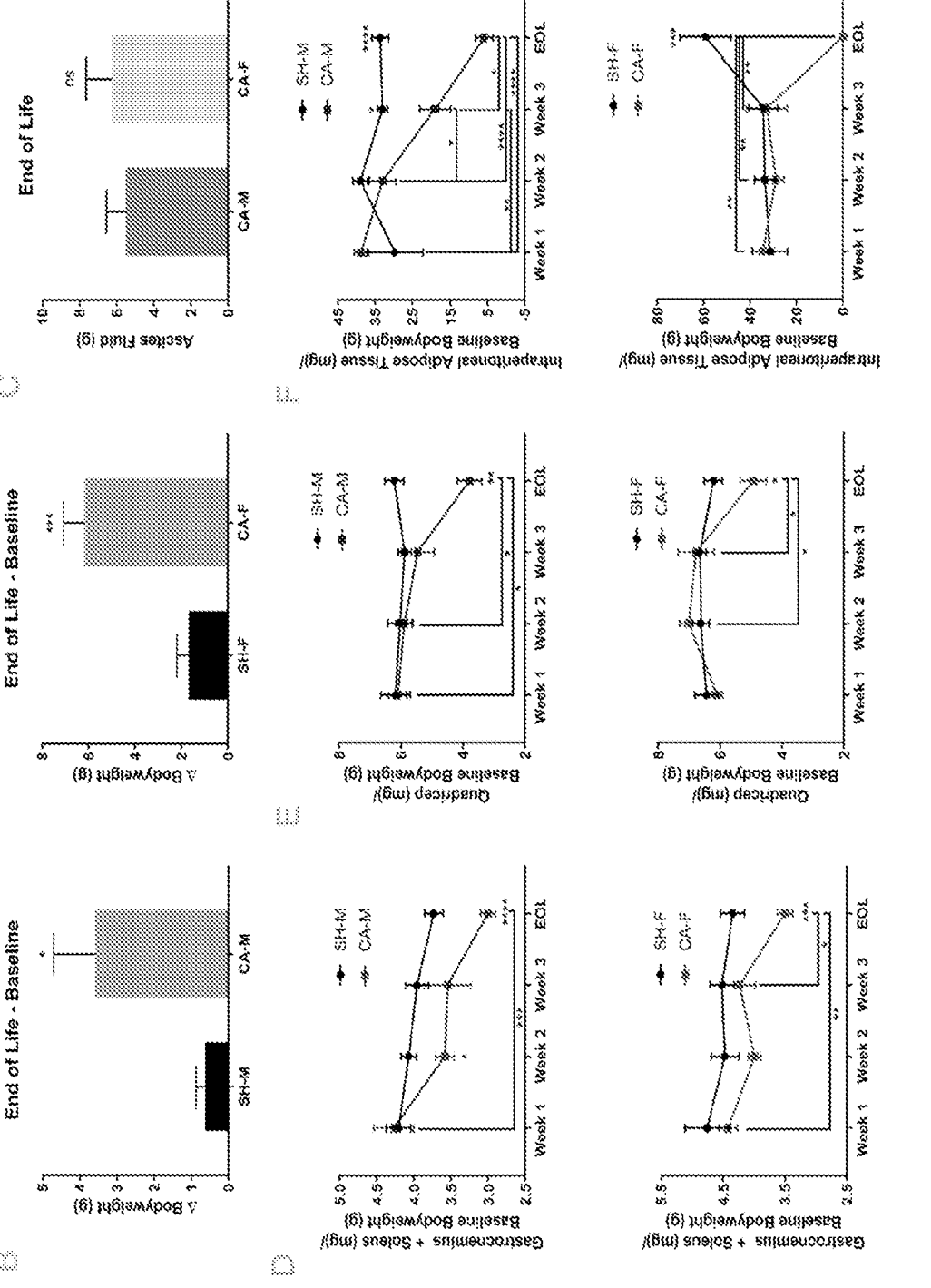

Clinically, attributing bodyweight changes to skeletal muscle and/or adipose tissue loss can inaccurately represent the nature of wasting and misguide treatment strategies and "successes". Thus, to directly assess cachexia tissue composition, skeletal muscle, adipose, and tissue weights were gathered at EOL. Upon confirmation of tissue wasting at EOL, follow up week-by-week cohort analyses were conducted to determine the temporal/progressive nature of atrophy across tissues and groups. All individual tissues were set to ratio with baseline bodyweight (so not to be influenced by cachexia progression) to allow for appropriate comparison across groups. CA-M experienced a significant decrease in gastrocnemius and soleus weights starting at week 2 (−12.0%) and extending to EOL (−19.5%), compared to SH-M (FIG. 2D), consistent with the progressive nature of cachectic wasting. Similar trends were observed in CA-F, with decreased gastrocnemius and soleus weights at week 2 (−10.7%; p=0.09), compared to SH-F (FIG. 2E), which were significantly decreased within and across groups at EOL (−20.8%). Quadriceps weight was retained in both CA-M and CA-F until EOL (FIG. 2F), indicating temporal and tissue-specific differences in skeletal muscle wasting which have been observed previously in cachexia models and other clinical atrophy conditions, but dissimilar to sex-specific quadricep atrophy in clinical cachexia. CA-M also presented with progressive decreases in intraperitoneal adipose tissue, with significant decreases at week 3 and EOL within and across groups (FIG. 2F). Discrepantly, CA-F retained adipose tissue mass up to week 3, followed by rapid and complete wasting of adipose tissue between these timepoints. This altered skeletal muscle and adipose tissue composition observed in CA-F is consistent with previous reports in other female cachexia preclinical models and patients, but not others, and might be explained by inherent hormonal differences influencing skeletal muscle and adipose tissue. The data here serves to confirm tissue atrophy and sex-specific cachectic discrepancies in the VM-M3 model.

Figures 3A, 3B, 3C:
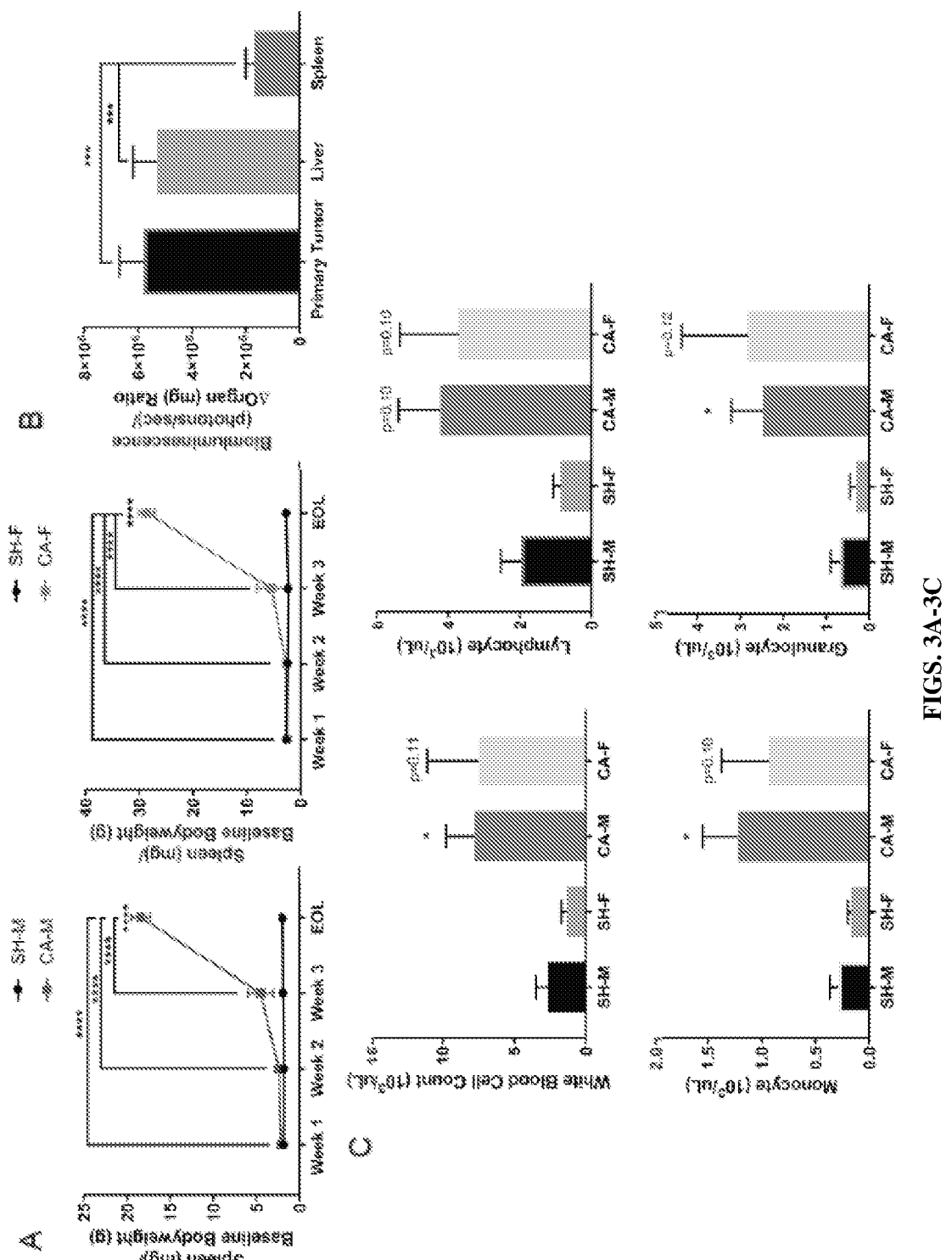
Figures 3E, 3F:
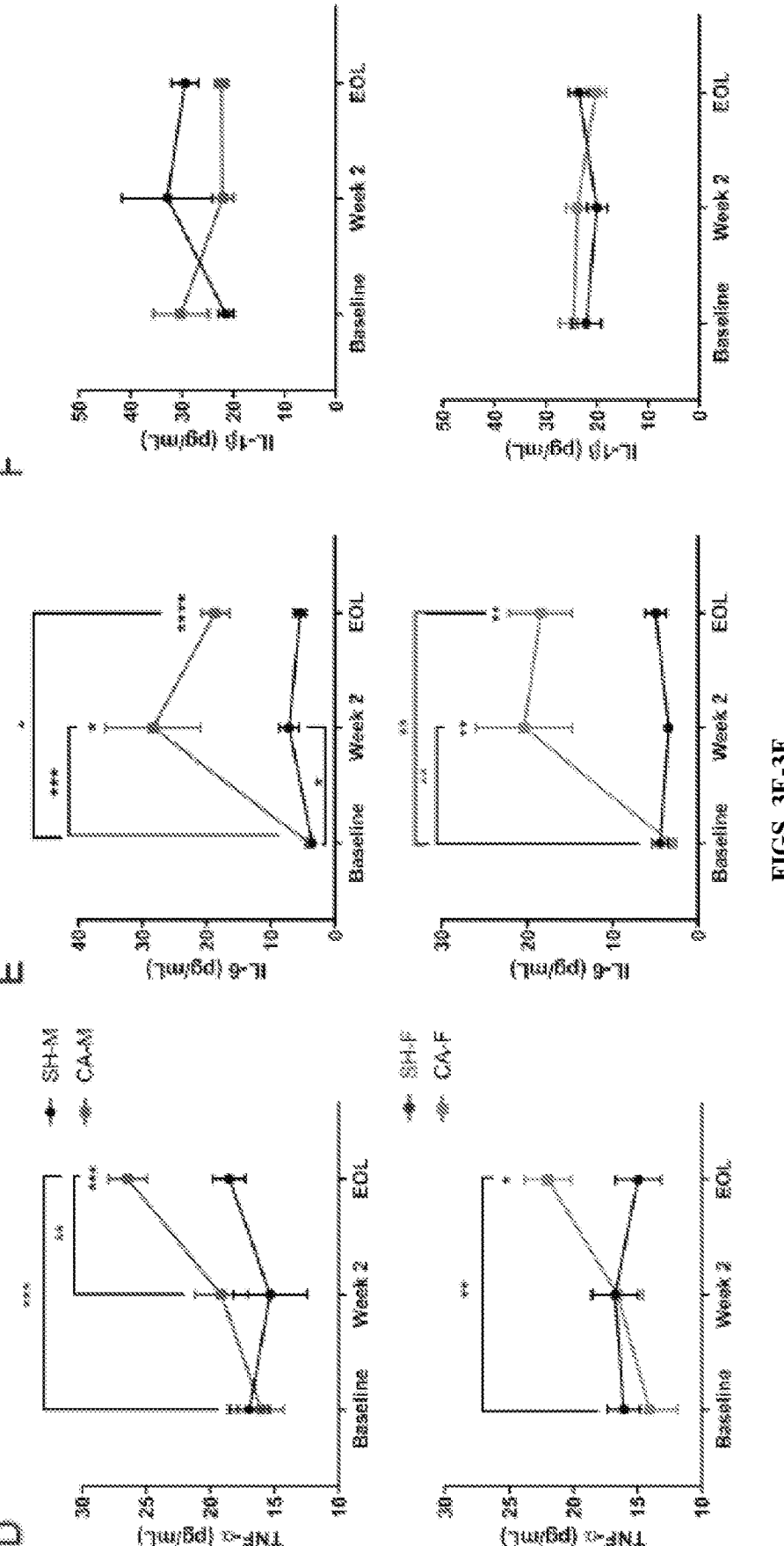

VM-M3 Develops Prolonged Systemic Inflammation: Inflammation has been reported to drive multiple facets of the cachexia phenotype, including tissue wasting, anorexia, metabolic abnormalities, and tumor progression, among others. To determine if VM-M3 animals developed systemic inflammation, spleen weight, white blood cell count, and cytokines were measured. Both CA-M and CA-F developed splenomegaly (FIG. 3A); however, increased spleen weight could also be attributed to tumor burden and/or other immunologic initiators. Thus, to determine whether enlarged spleen weight could be directly attributed to tumor burden alone, a ratio of tumor burden (bioluminescence in photon/ sec) to cancer-induced tissue weight changes (cancer to sham tissue weight differences) was calculated for the primary tumor, liver, and spleen, as the primary tumor bioluminescence would be directly proportional to increased tumor size and serve as a control ratio. The ratio of tumor burden to cancer-induced tissue weight differences (FIG. 3B) was similar between the primary tumor and liver, but dissimilar to spleen, indicating that the change in weight within the liver could be primarily and/or completely attributed to internal organ tumor burden. The spleen weight changes, along with G-CSF elevations (FIG. 9B) indicated spleen enlargement was not due to tumor burden but was indicative of a prominent immunologic response. Additionally, white blood cell counts, along with cellular subpopulations (monocytes and granulocytes), were significantly elevated in CA-M (FIG. 3C). In CA-F, however, white blood cell counts were not significantly elevated, although they did show similar trends to CA-M. Tumor necrosis factor-$\alpha$ (TNF-$\alpha$) and Interleukin-6 (IL-6), proinflammatory cytokines commonly reported in the cachexia phenotype, were elevated in CA-M and CA-F across and within groups (FIG. 3D,E). However, Interleukin-10 (IL-1$\beta$), another proinflammatory cytokine reportedly associated with some cachexia phenotypes, was not significantly altered within or across groups (FIG. 3F). These inflammatory biomarkers at the organ, cellular, and molecular levels within VM-M3 animals are indicative of a prolonged systemic inflammatory response and consistent with the cancer cachexia phenotype.

Figure 4A:
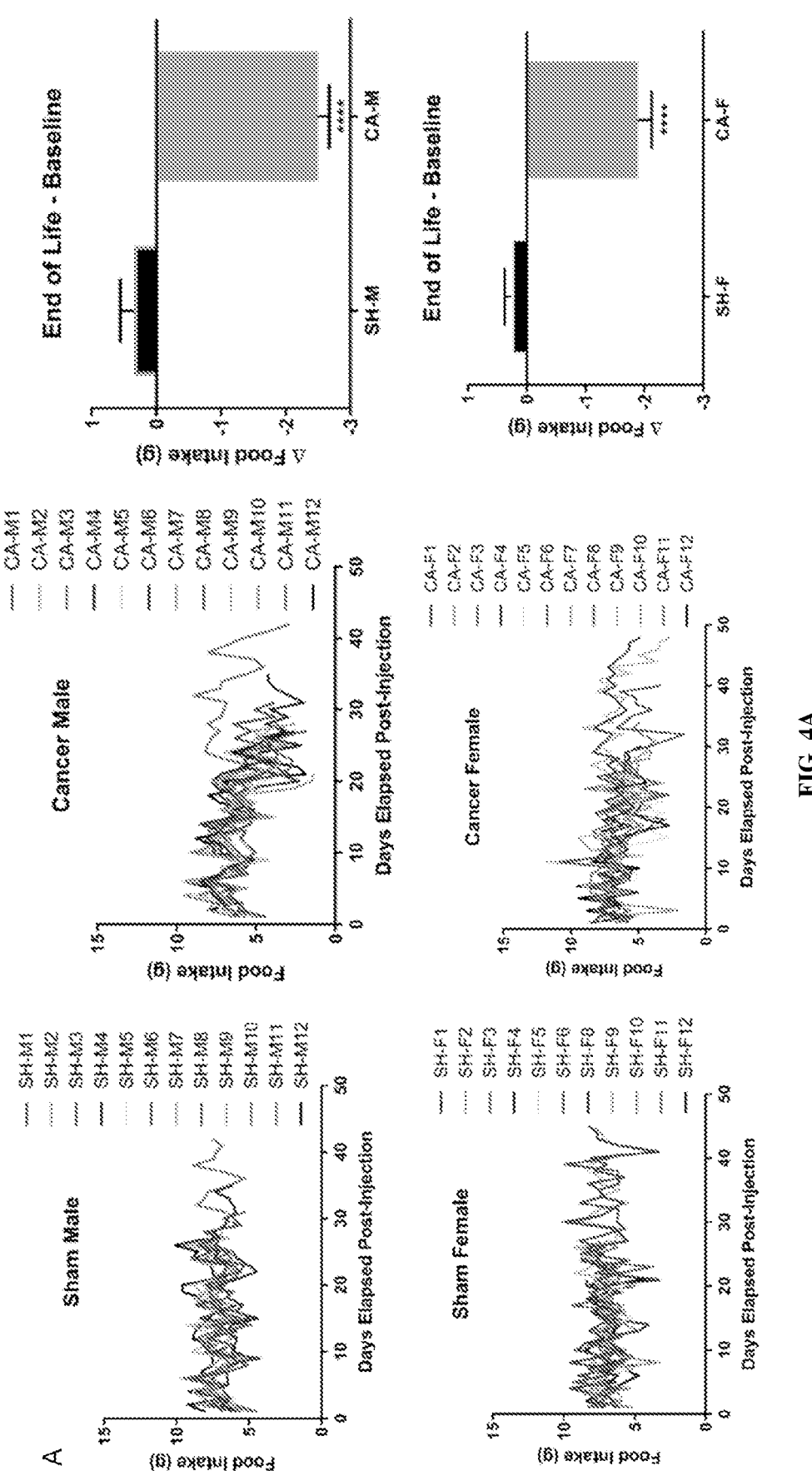
FIGS. 4A-4C show VM-M3 develop anorexia, anemia, protein breakdown, hypoalbuminemia, and metabolic derangement.
Figure 4B:
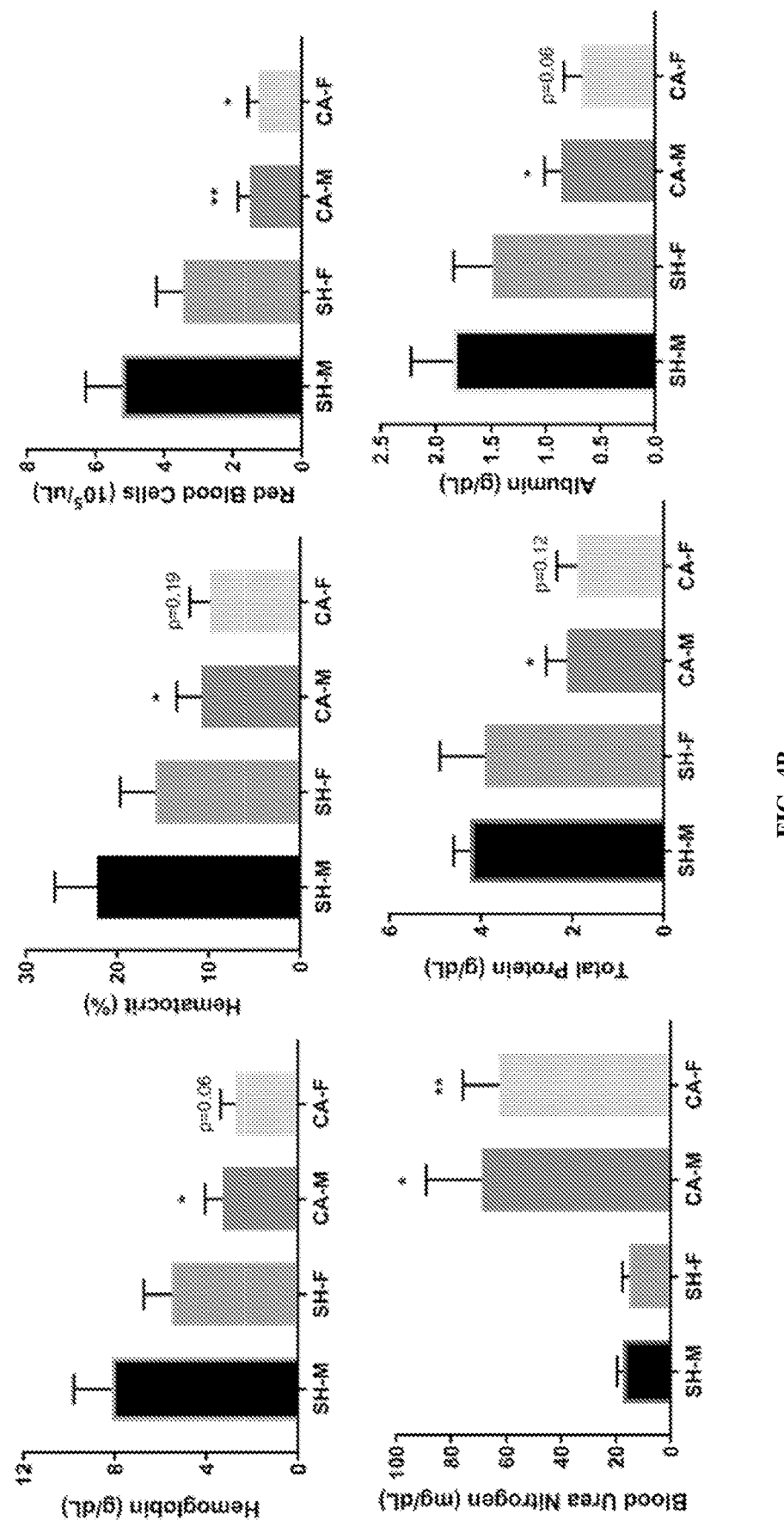
Figure 4C:
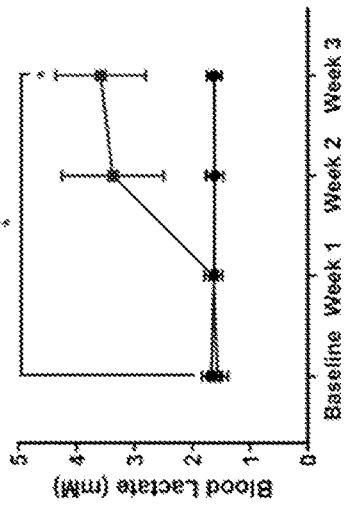
Figure 4C:
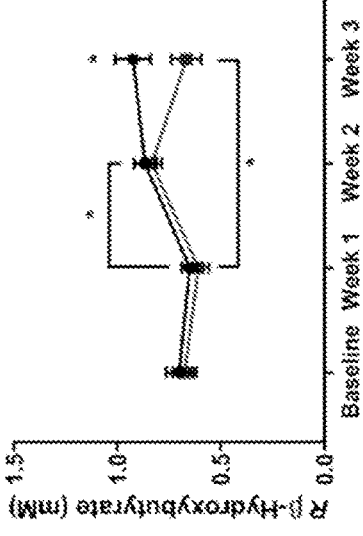
Figure 4C:
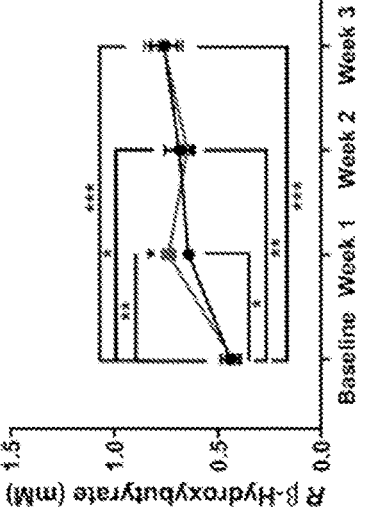
Figure 4C:
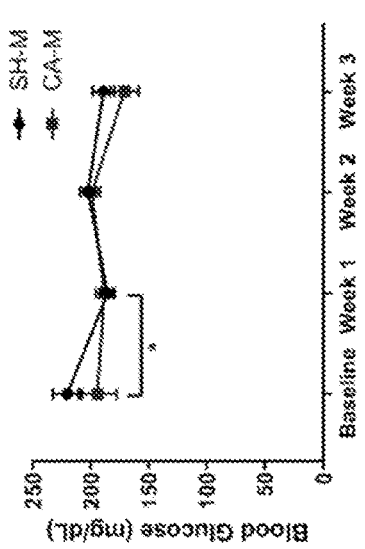
Figure 4C:
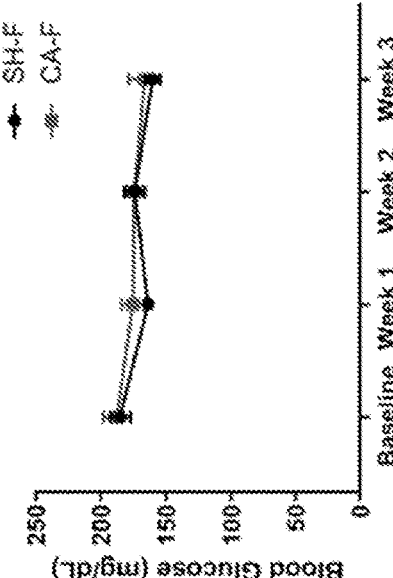
Figure 10:
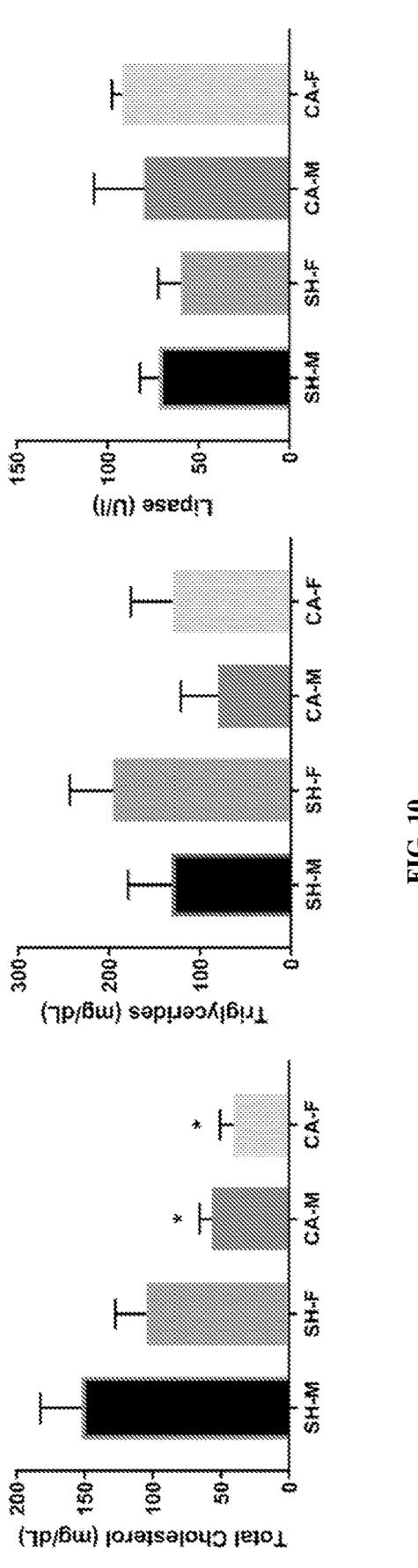
FIG. 10 shows VM-M3 circulating lipids. Total Cholesterol (n=5/group), Triglycerides (n=4/group) and Lipase (n=5/group) were analyzed via colorimetry analysis. Data: EOL, Experiment 1a. Data information: Across sex differences were analyzed with unpaired t-test. Abbreviations: SH-M, Sham Males; CA-M, Cancer Males; SH-F, Sham Females; CA-F, Cancer Females. Data are mean±SEM. *P<0.05.

VM-M3 Develops Anorexia, Anemia, Protein Breakdown, Hypoalbuminemia, and Metabolic Derangement: Anorexia, anemia, elevated markers of protein breakdown, hypoalbuminemia, and metabolic derangement remain prominent clinical comorbidities of the full CACS, but are often not evaluated in pre-clinical modeling to determine the potential clinical relevance of these model systems. To determine whether the VM-M3 model developed the full CACS as clinically presented, all aforementioned clinical comorbidities were evaluated. Food intake was monitored daily to determine the presence of anorexia, a common, contributory, and clinically impactful characteristic of CACS. Both CA-M and CA-F developed anorexia, compared to the elevation in food intake seen in both SH-M and SH-F (FIG. 4A). Anemia can be a result of inflammation and/or shifted metabolic demands away from red blood cell production, which can contribute to fatigue and might explain the noticeable lethargy/functional decline in cachexia patients and VM-M3 animals. CA-M developed anemia as indicated by significantly reduced hemoglobin, hematocrit, and red blood cell count (FIG. 4B). CA-F had significant reductions in red blood cell count and trends for decreases in hemoglobin. Blood urea nitrogen and total protein, clinical markers of whole-body protein kinetics, are commonly elevated and decreased, respectively, in CACS patients. CA-M and CA-F had significantly elevated blood urea nitrogen levels (FIG. 4B). CA-M and CA-F had significantly and non-significantly reduced total protein levels, respectively. Both biomarkers illustrated increased systemic protein breakdown. Albumin, another critical biomarker commonly reduced in CACS patients, was decreased in VM-M3 animals (FIG. 4B). This decrease is hypothesized to be a consequence of shunting of hepatic resources towards acute response proteins during the inflammatory response in CACS and/or nutritional status, and has been linked to higher mortality in cancer, cachexia, and other atrophy diseases. CA-M and CA-F also developed hypocholesterolemia, without changes in circulating triglycerides or lipase, potentially attributed to inflammation, disease progression, and splenomegaly (FIG. 10).

Figure 11:
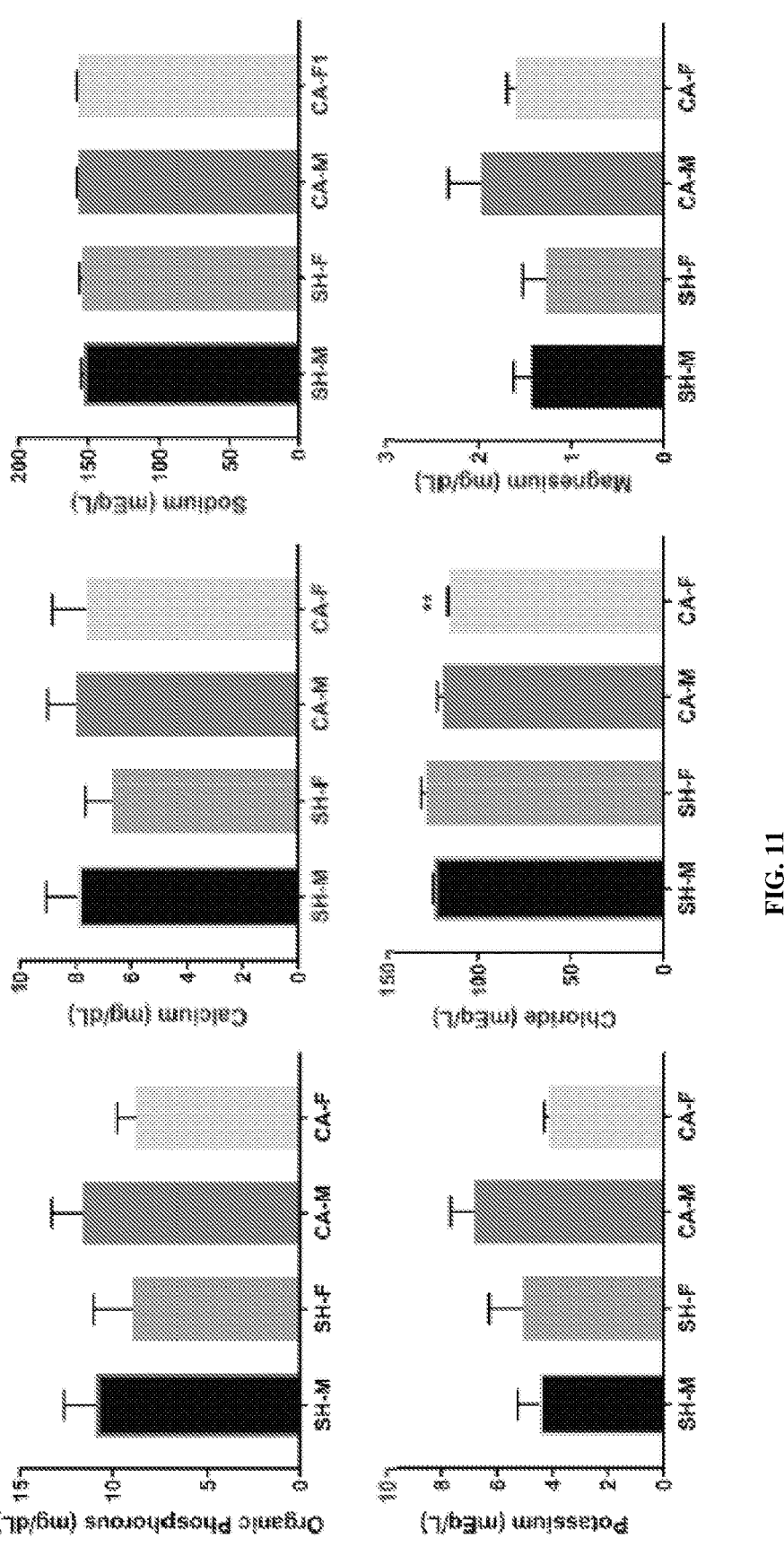
FIG. 11 shows alterations seen in VM-M3 cannot be explained by altered hydration status. Organic Phosphorous (males n=5/group; female n=4/group), Calcium (males n=5/group; female n=4/group), Sodium (n=3/group), Potassium (males n=3/group; female n=4/group), Chloride (males n=2-3/group; female n=4/group), Magnesium (males n=3/group; female n=4/group) were quantified via potentiometrics. Data: EOL, Experiment 1a. Data information: Across sex differences were analyzed with unpaired t-test. Abbreviations: SH-M, Sham Males; CA-M, Cancer Males; SH-F, Sham Females; CA-F, Cancer Females. Data are mean±SEM. **P<0.01.

Blood glucose, R $\beta$-hydroxybutyrate, and lactate were also measured weekly to further evaluate metabolic alterations associated with the model. Blood glucose did not change, except for a significant decrease from baseline to week 1 in CA-M (FIG. 4C); however this did not exclude the possibility that metabolic changes were occurring while the serum metabolites remained within the homeostatic range, as elevated glucose turnover has been reported in cachexia patients. Blood R $\beta$-hydroxybutyrate did not differ significantly between sham and cancer groups for male and female mice, except for week 3 for males and week 1 for females. Follow-up analysis indicated that blood lactate was significantly elevated in CA-M (FIG. 4C), indicating that metabolic alterations were present likely via the aerobic fermentation pathway (systemically and/or tumor-driven) that may have contributed to increased metabolic inefficiency. Collectively, these observations in circulating biomarkers were not explained by altered hydration status (FIG. 11). Taken together, VM-M3 animals demonstrated comorbid anorexia, anemia, elevated markers of protein breakdown, hypoalbuminemia, and metabolic derangement, modeling the comprehensive CACS as clinically described.

Figures 12A, 12B, 12C:
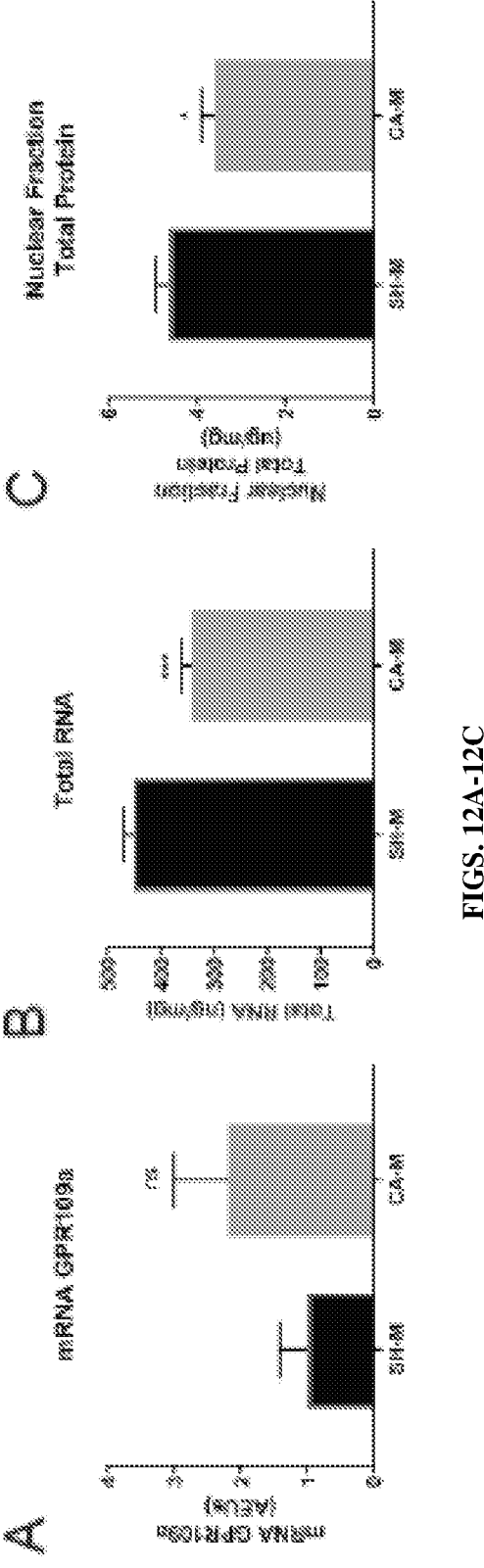
Figure 12D:
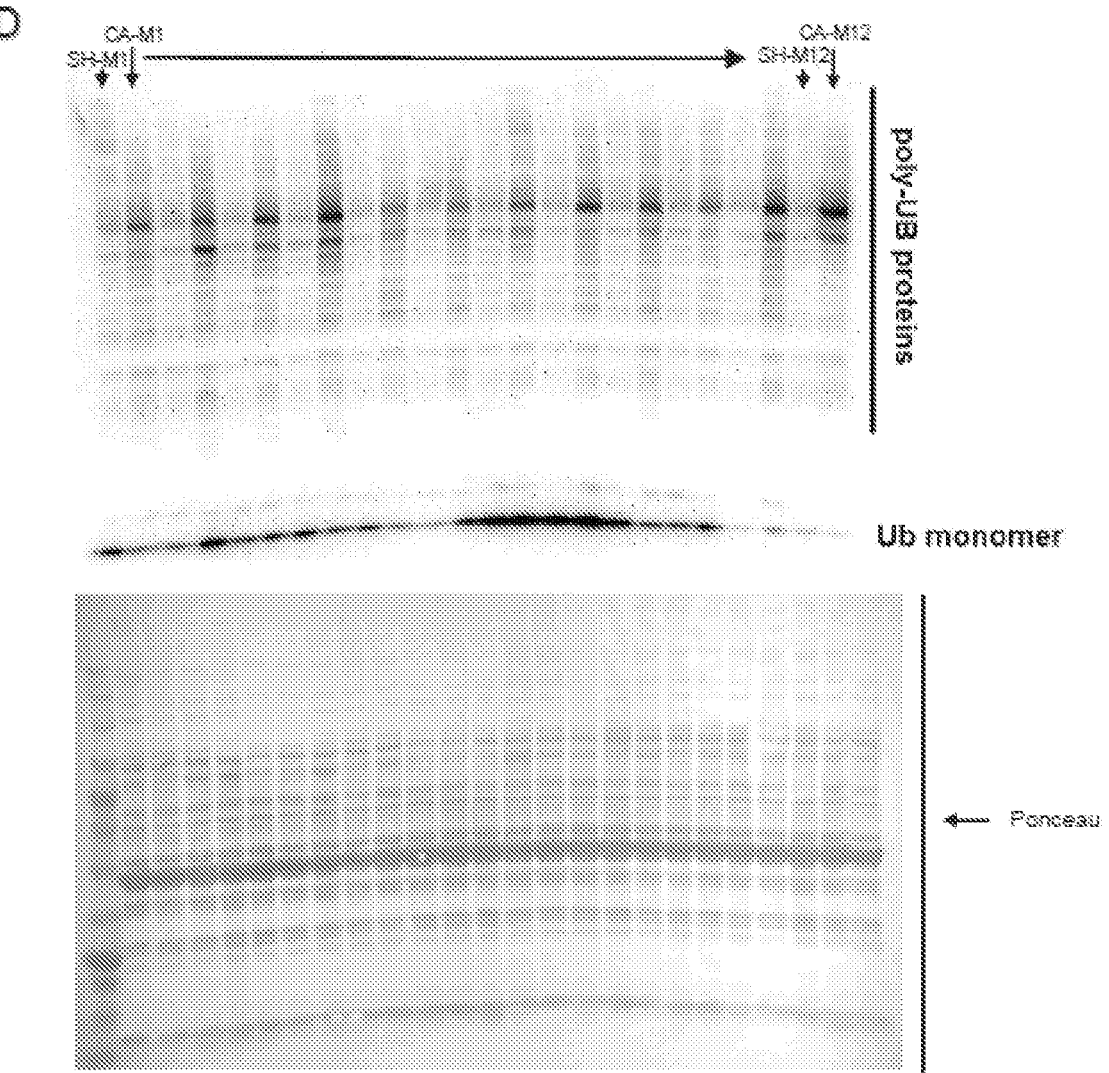

IGF-1/Insulin-FOXO3a-Ubiquitin Proteasome Pathway is Activated in VM-M3 Skeletal Muscle: Multiple cachexia atrophy mechanisms have been identified in rodent modeling and emergent evidence indicates that the ubiquitin proteasome degradation pathway is a prominent contributor to skeletal muscle atrophy. To determine the mechanism of skeletal muscle atrophy in the VM-M3 model of CACS, follow up analyses were conducted in CA-M and activation status of the ubiquitin proteasome pathway was examined. Results confirmed muscle protein poly-ubiquitination activation (FIG. 5A; FIG. 12D), a critical step in the irreversible process of protein degradation. Specifically, 26S proteasome quantity and capacity were quantified via 20S proteasome core western blotting and fluorescence LLVY peptide quantitation of muscle tissue lysates, respectively. Neither quantity (FIG. 5B; FIG. 12E) nor capacity (FIG. 5B) of the 26S proteasome were altered, indicating atrophy likely occurred via upregulation of muscle protein poly-ubiquitination.

Figures 5, 5A, 5B, 5C, 5D:
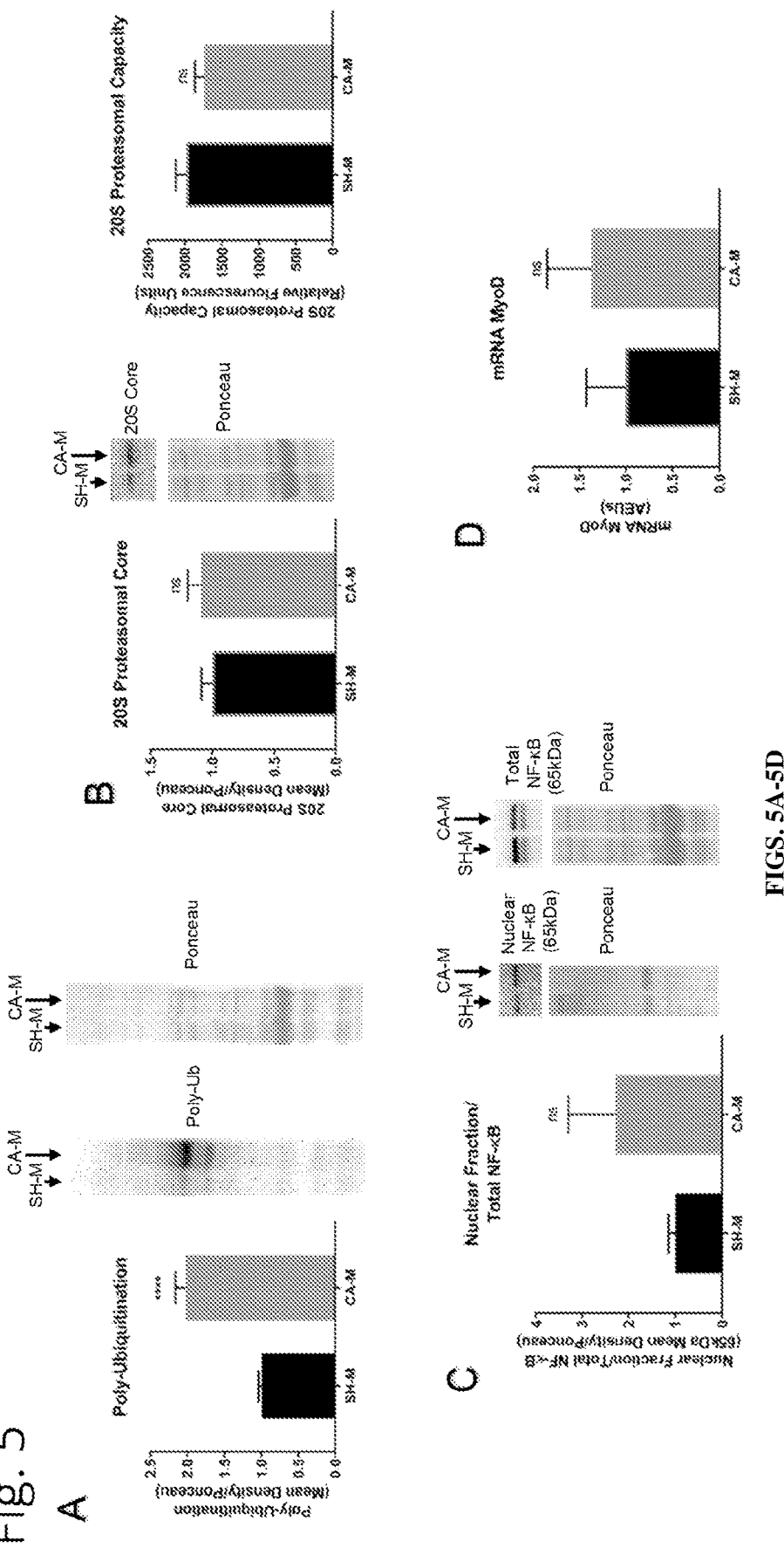
FIGS. 5A-5I show IGF-1/Insulin-FOXO3a-Ubiquitin Proteasome Pathway is activated in VM-M3 skeletal muscle.
Figure 12G:
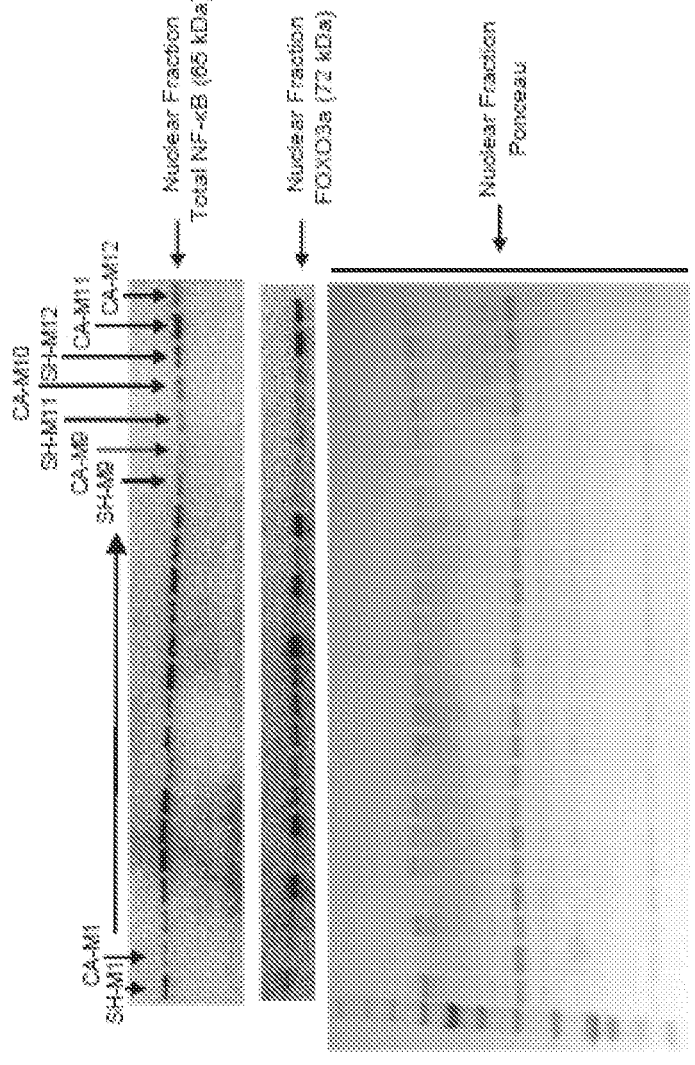
Figure 12G:
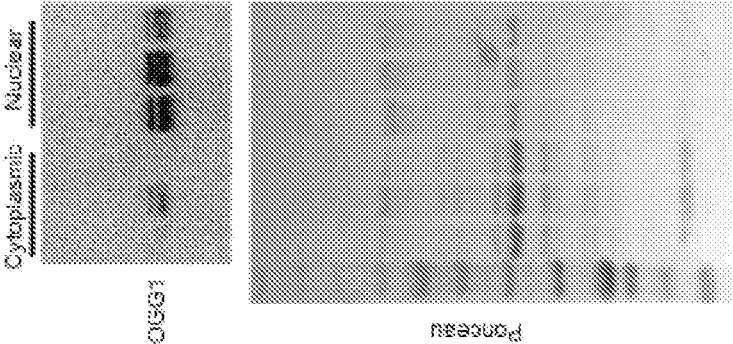
Figures 12H, 12I:
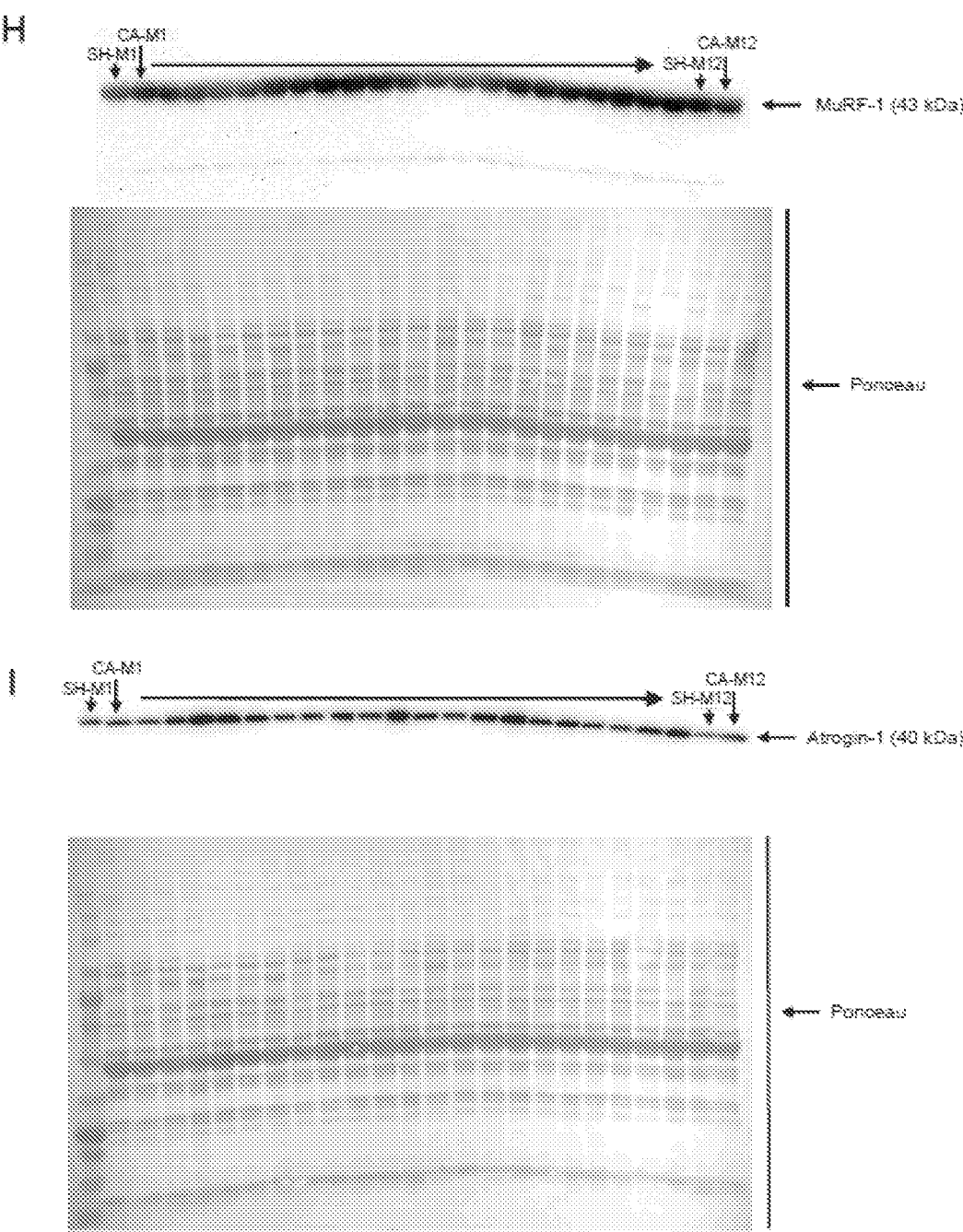

TNF-$\alpha$ has also been shown to play a direct role in skeletal muscle atrophy by upregulating Nuclear factor-kappa B (NF-$\kappa$B) and subsequently ubiquitin proteasome activity. Following prior confirmation of TNF-$\alpha$ elevation (FIG. 3D), NF-$\kappa$B activation was explored in VM-M3 skeletal muscle to determine which upstream pathway was associated with ubiquitination. Nuclear fraction versus total NF-$\kappa$B (65 kDa) protein analysis revealed no significant differences between CA-M and SH-M (FIG. 5C; FIG. 12F-G); however, NF-$\kappa$B is temporally regulated, and analysis may have missed the activation timepoint. Thus, mRNA expression of MyoD, MuRF-1, Atrogin-1, and GRP109a as well as protein levels of MuRF-1 and Atrogin-1 were analyzed as surrogates of NF-$\kappa$B activation. MyoD expression drives myogenesis in skeletal muscle, but activation of NF-$\kappa$B is known to directly induce the degradation of MyoD mRNA. Results indicated MyoD mRNA was unchanged in CA-M (FIG. 5D). Additionally, MuRF-1 and Atrogin-1 are skeletal muscle-specific E3 ligases which can be upregulated via NF-κB activation; however, both mRNA and protein levels were similar between conditions (FIG. 5E-F; FIG. 12H-I). mRNA levels for GPR109a, a receptor protein known to be upregulated by NF-κB activation and subsequently induce negative feedback upon NF-κB pathway activation, revealed no differences between conditions either (FIG. 12A). Interestingly, total RNA levels (a surrogate of ribosome density) and nuclear fraction protein levels were significantly reduced in the VM-M3 skeletal muscle (FIG. 12B-C) further suggesting these animals were in a catabolic state. TNF-α is known to chronically activate NF-κB. Given that all of the aforementioned markers indicated no differences between conditions regarding NF-κB pathway activity, serum levels of a reported counter-regulator of TNF-α-induced NF-κB activation in muscle, IL-10, was explored. Serum IL-10 was elevated, potentially explaining the NF-κB results (FIG. 5G) despite the increases in TNF-α (FIG. 3D) and poly-ubiquitinated protein levels (FIG. 5A).

Figures 5E, 5F, 5G, 5H, 5I:
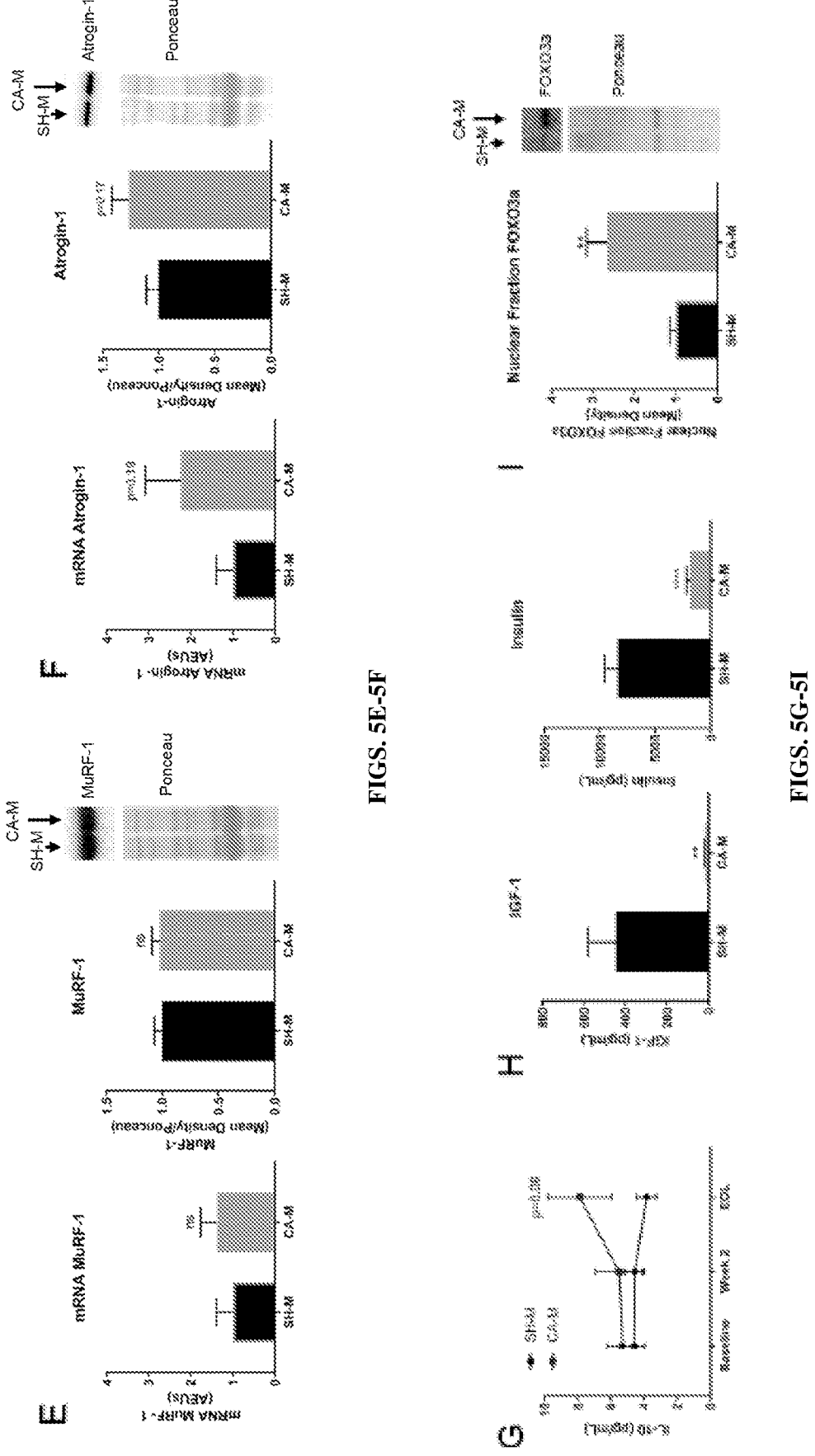

Another upstream activator of the ubiquitin proteasome pathway is via IGF-1/insulin, FOXO3a, and Atrogin-1 signaling. Serum IGF-1 and insulin levels were analyzed in VM-M3 animals to determine if this upstream mechanism was associated with muscle protein poly-ubiquitination. Quantification of serum IGF-1 and insulin revealed 26-fold and 4.6-fold downregulation of both anabolic hormones, respectively (FIG. 5H). Quantification of nuclear fraction FOXO3a revealed a 2.3-fold increase in VM-M3 animals (FIG. 5I). Collectively, these results suggest that VM-M3 skeletal muscle atrophy may occur through a reduction in serum IGF-1/insulin and a subsequent increase in FOXO3a activation resulting in an increase in muscle protein poly-ubiquitination; all of which was independent of TNF-α-induced NF-κB activation.

Ketone Diester Mitigates Comorbidities, Tumor Burden, and Skeletal Muscle Atrophy in Cancer Anorexia Cachexia Syndrome: IGF-1/insulin, FOXO3a, and the ubiquitin proteasome pathway are implicated in muscle homeostasis and numerous atrophy conditions, including nutrient deprivation. Interestingly, patients undergoing extreme nutrient deprivation (i.e. prolonged fasting/anorexia) upregulate endogenous ketone body production, which is hypothesized to allow for prolonged survival via a protective and progressive metabolic adaptation that attenuates muscle atrophy. Previously, dietary restrictions and/or infusion-induced elevations of ketone bodies limited the exploration and clinical translation of therapeutic ketosis; however, a novel, orally ingestible exogenous KDE may be a viable therapeutic strategy. This KDE was assessed to determine its effect on anorexia, systemic metabolism, tumor and metastatic burden, and skeletal muscle catabolism in multifactorial CACS modeling.

Figures 6A, 6B:
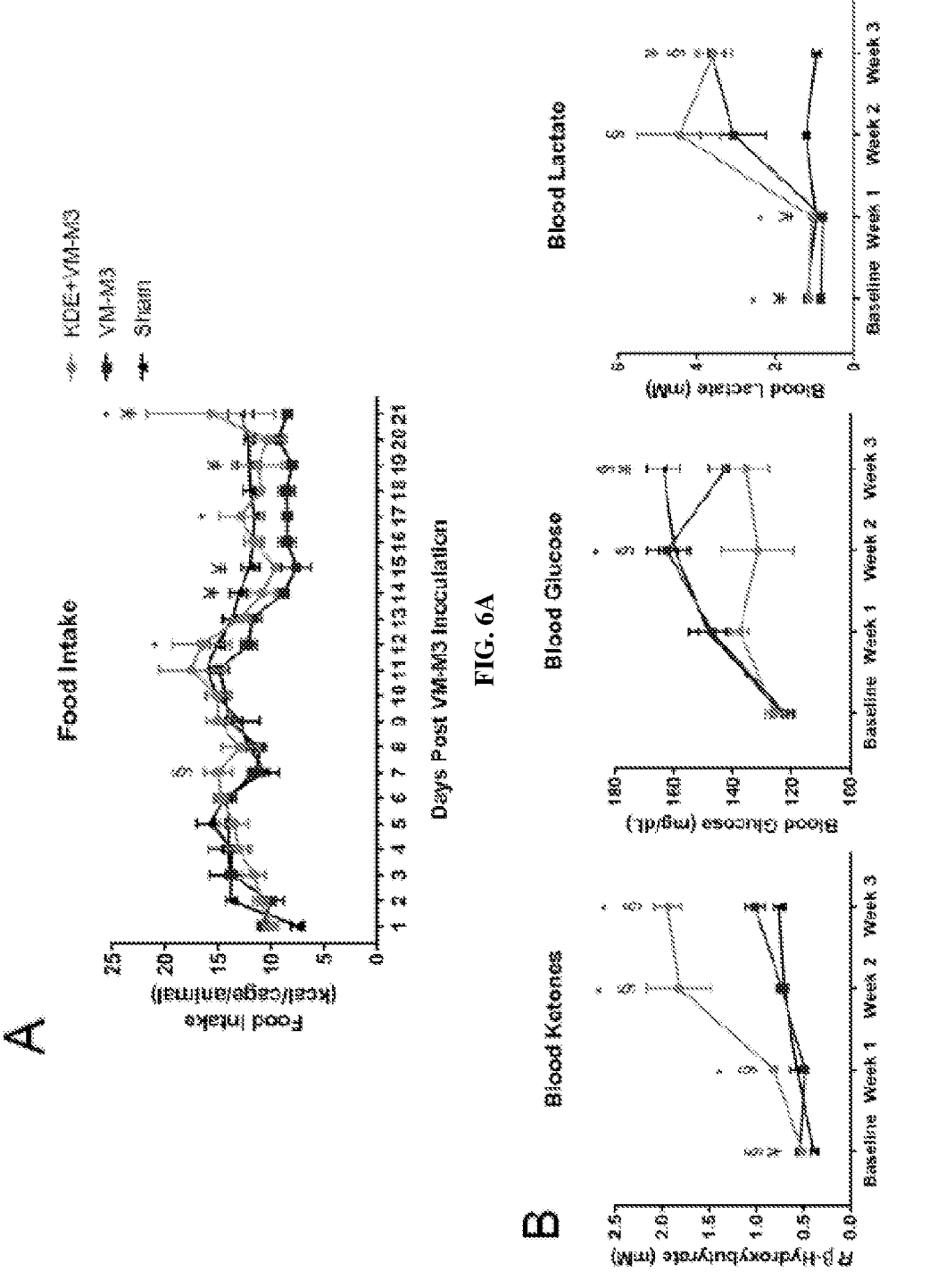
FIGS. 6A-6I show ketone diester mitigates comorbidities, tumor burden indices, and skeletal muscle atrophy in cancer anorexia cachexia syndrome.
Figures 6C, 6D:
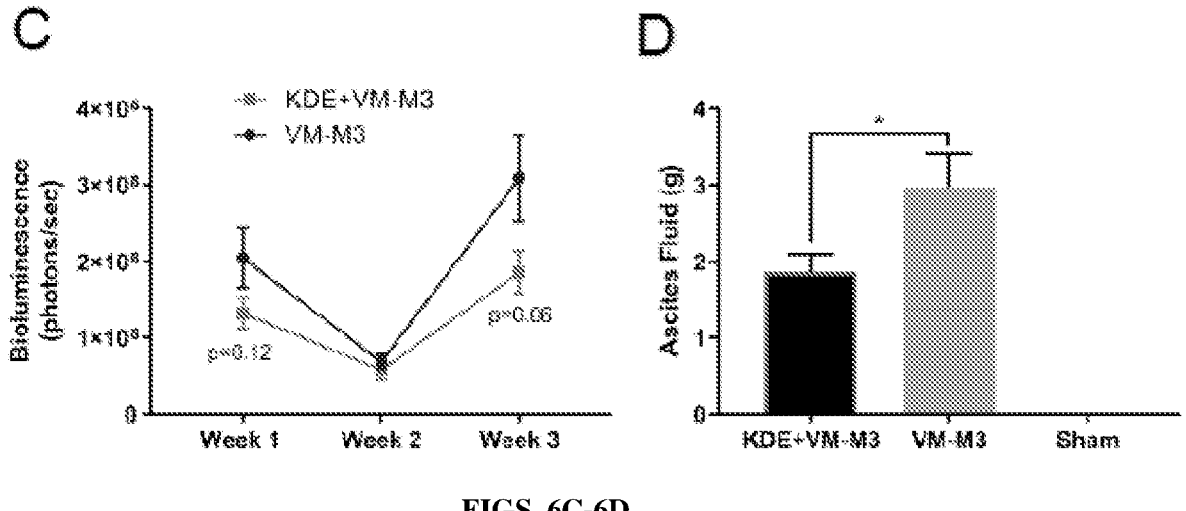
Figure 6E:
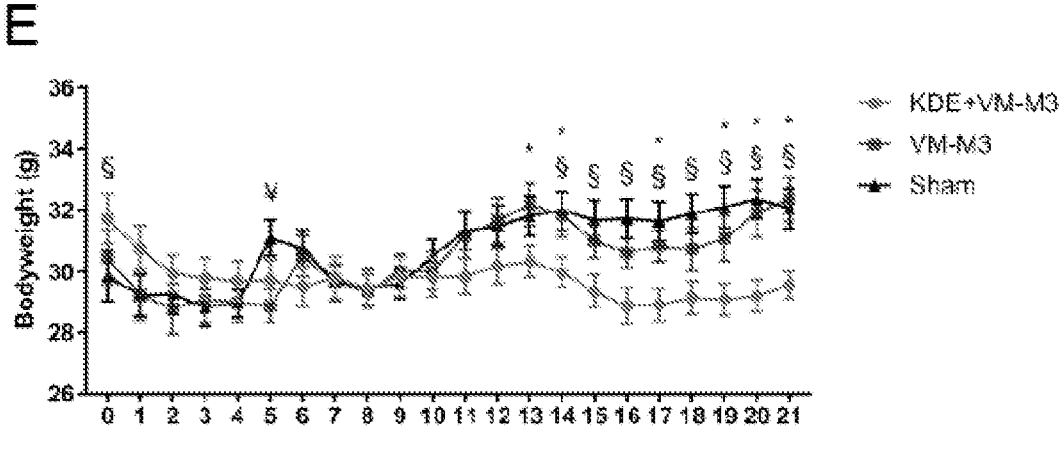

To determine whether KDE could alter systemic metabolism, blood metabolites were measured at baseline following a standard diet and after a 4-day transition to a standard diet supplemented with 20% KDE, 25% KDE, or 30% KDE. Results indicated 20% KDE and 30% KDE caused significant elevations in blood ketone levels, with 30% KDE inducing the highest ketone elevations (Fig S6C). All KDE groups exhibited significant reductions in blood glucose levels, with 30% KDE inducing the greatest reduction in glucose. A second study was initiated to expand upon these findings, as prior work revealed that exogenous administration of ketone bodies may reduce ad libitum food intake and confound evaluation of KDE effect on catabolism. To control for this effect, food palatability was increased by incrementally integrating the KDE into the diet (5%/day) over a 7-day period to achieve 30% KDE. The 30% KDE was well-tolerated as indicated by bodyweight maintenance (FIG. 13B), and since 30% KDE caused the greatest alteration in systemic metabolism, mirroring the metabolic alterations seen during extreme nutrient deprivation, 30% KDE was administered in VM-M3 CACS (KDE+VM-M3) utilizing intraperitoneal implantation to determine whether KDE would alter the course of CACS-induced atrophy compared to VM-M3 CACS-alone (VM-M3) and PBS-only (Sham). Food intake was tracked daily to determine if KDE administration altered the anorexic phenotype. VM-M3 experienced a reduction in food intake (FIG. 6A); however, animals in the KDE+VM-M3 demonstrated attenuation of the predicted anorexic phenotype in this CACS model (FIG. 6A). To determine whether KDE could alter metabolism in CACS, blood ketones, glucose, and lactate were measured weekly. KDE induced sustained elevations in circulating ketones and reductions in blood glucose in KDE+VM-M3 compared to both VM-M3 and Sham (FIG. 6B), illustrating KDE-induced alterations in CACS systemic metabolism. No difference was found between KDE+VM-M3 and VM-M3 for blood lactate (FIG. 6B), potentially indicating similar tumor or inflammation-induced aerobic fermentation. Thus, to determine if KDE altered tumor burden, in vivo bioluminescence imaging was analyzed weekly. Interestingly, KDE+VM-M3 demonstrated non-significant reductions in whole animal tumor burden (FIG. 6C). Additionally, ascites fluid, a surrogate marker of metastatic spread, was significantly reduced in KDE+VM-M3 compared to VM-M3 (FIG. 6D), indicating KDE-induced reductions in markers of tumor burden.

Figure 6F:
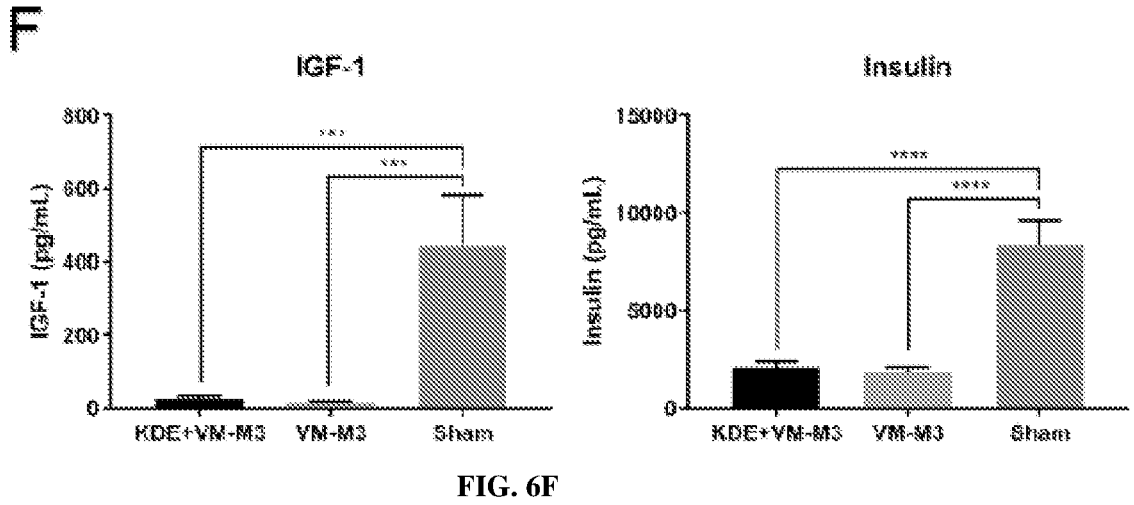
Figures 6G, 6H:
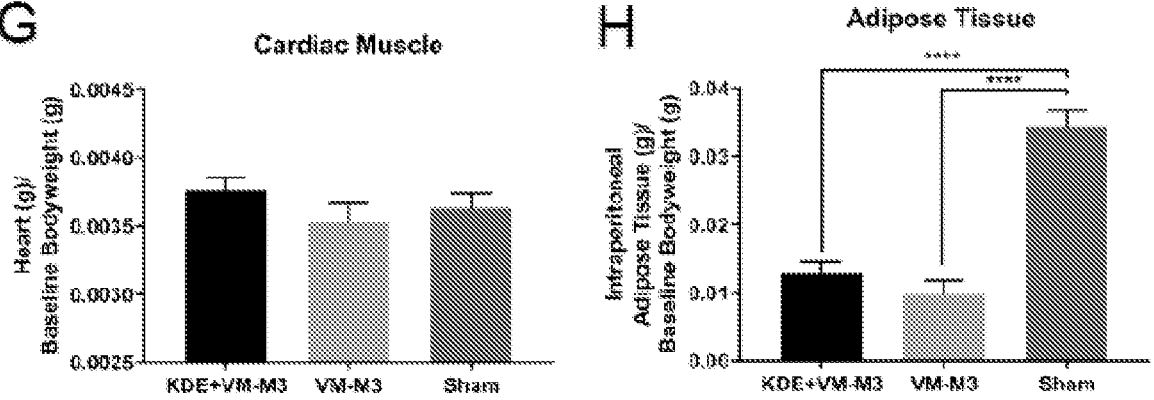
Figure 6I:
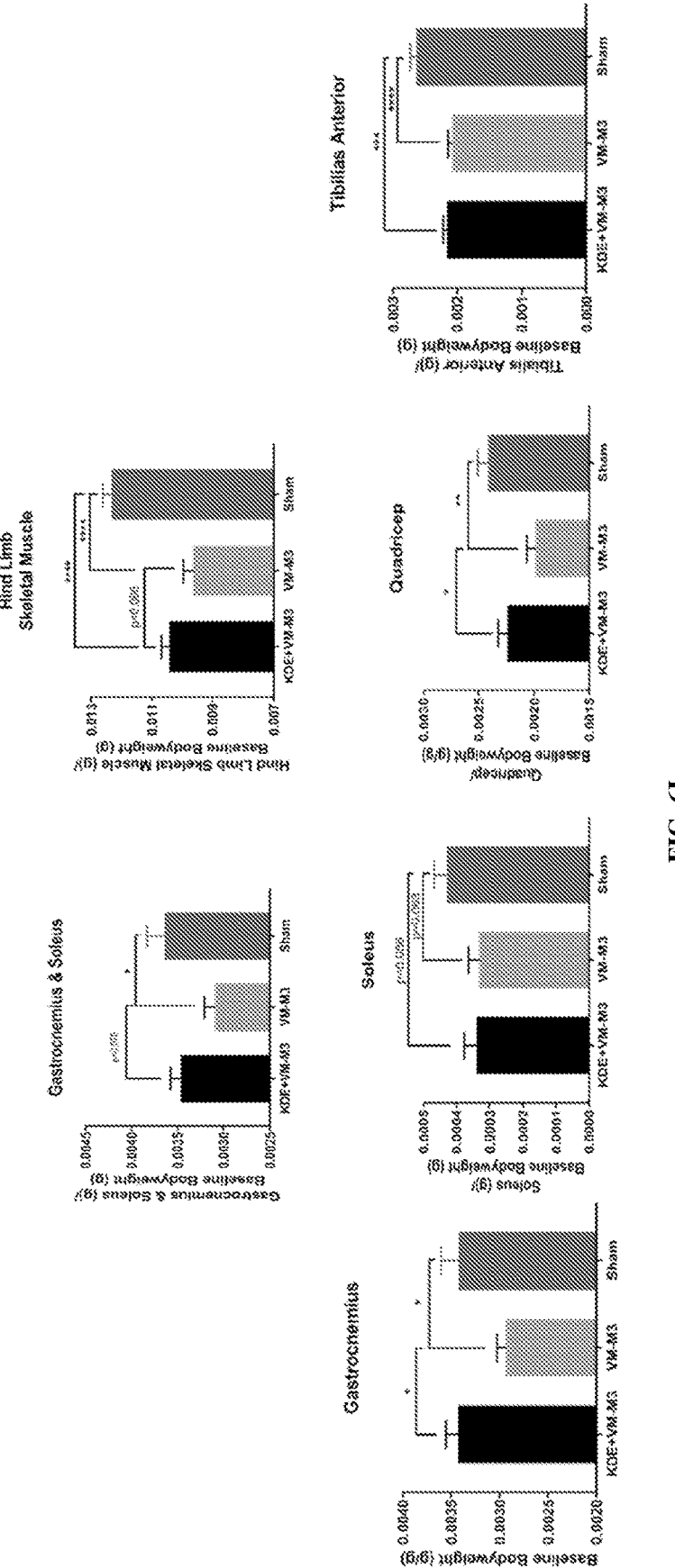

To determine if KDE altered body composition and whether this was through alteration in model-specific catabolic drivers, bodyweight was tracked daily, while serum IGF-1 and insulin as well as relative masses for cardiac tissue, adipose tissue, and skeletal muscle tissue were evaluated 3 weeks post-implantation, prior to EOL. KDE+VM-M3 had a lower bodyweight compared to VM-M3 and Sham (FIG. 6E); however, as both ascites fluid and tumor burden confound bodyweight in VM-M3 animals, bodyweight alone could not reliably indicate tissue atrophy in the VM-M3 model of CACS. KDE+VM-M3 and VM-M3 both demonstrated significantly reduced serum IGF-1 and insulin, demonstrating that KDE did not alter circulating anabolic hormone levels (FIG. 6F). Cardiac tissue was found to be unaltered by CACS or across group (FIG. 6G). Additionally, adipose tissue atrophied to equivalent levels in KDE+VM-M3 and VM-M3, indicating KDE was unable to alter adipose tissue catabolism. However, the KDE did attenuate muscle atrophy across numerous skeletal muscle tissues (FIG. 6I). Taken together, the KDE was well tolerated, attenuated anorexia, altered systemic metabolism, attenuated indices of tumor burden, and reduced skeletal muscle atrophy without changing circulating IGF-1 and insulin levels, illustrating a unique and multifaceted anti-CACS therapy.

Figure 7A:
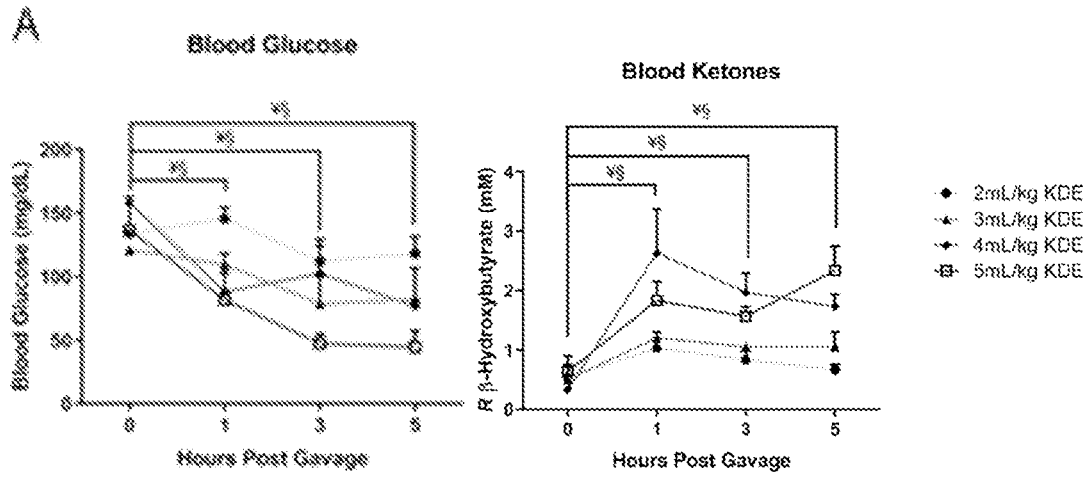
FIGS. 7A-7F show ketone diester mitigates bodyweight loss and comorbidities in inflammation-induced atrophy.
Figures 7B, 7C:
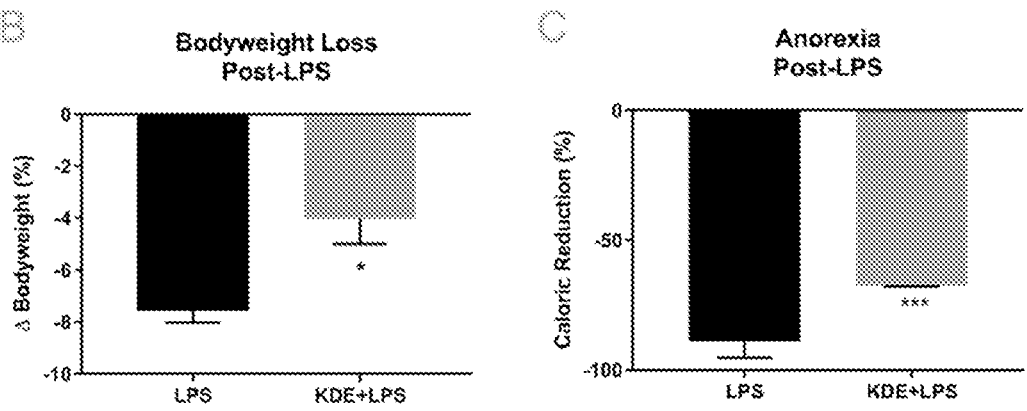

Ketone Diester Mitigates Bodyweight Loss and Comorbidities in Inflammation-Induced Atrophy: Reductions in anorexia, tumor burden, and skeletal muscle atrophy all present ideal outcomes in the clinical environment of CACS. It should be noted, however, that altered anorexia and tumor burden can confound interpretation of the direct effects of the KDE on skeletal muscle atrophy. To determine direct effects of KDE on catabolism when controlling for confounding variables of cancer and anorexia, KDE was evaluated in an inflammation-induced atrophy environment of LPS-induced sepsis, which has been shown to produce an overlapping multifactorial atrophy environment of low IGF-1/insulin, systemic inflammation, anorexia, anemia, hypoalbuminemia, metabolic derangement, and upregulated ubiquitin proteasome signaling. Due to the rapid nature of LPS-induced atrophy, various dosages of KDE were gavaged to determine their ability to rapidly shift systemic metabolism. Both 4 mL/kg and 5 mL/kg KDE dosages resulted in significant and rapid reductions in blood glucose and elevations in blood ketones (FIG. 7A). To determine KDE's effect on cancer-independent catabolism, a maximal non-fatal LPS dose (10 mg/kg) was administered, followed by a single 4 mL/kg water (LPS) or KDE (KDE+LPS) gavage. KDE attenuated bodyweight loss 47% within the first 24 hours post-LPS administration (FIG. 7B). Consistent with what was found in CACS, KDE also significantly reduced anorexic symptoms (FIG. 7C).

Figure 7D:
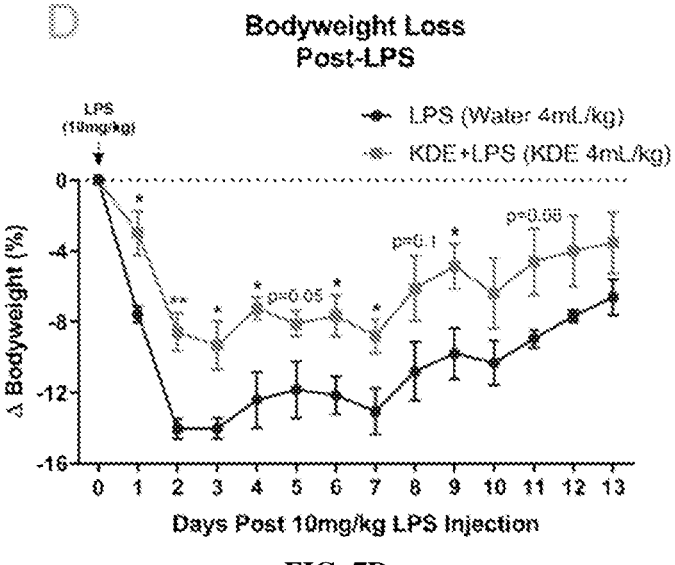
Figure 7E:
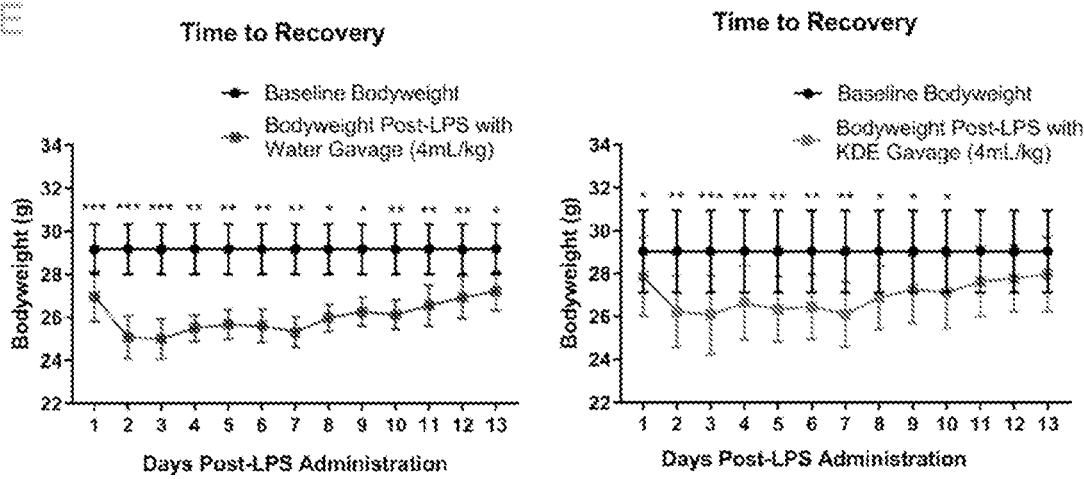
Figure 7F:
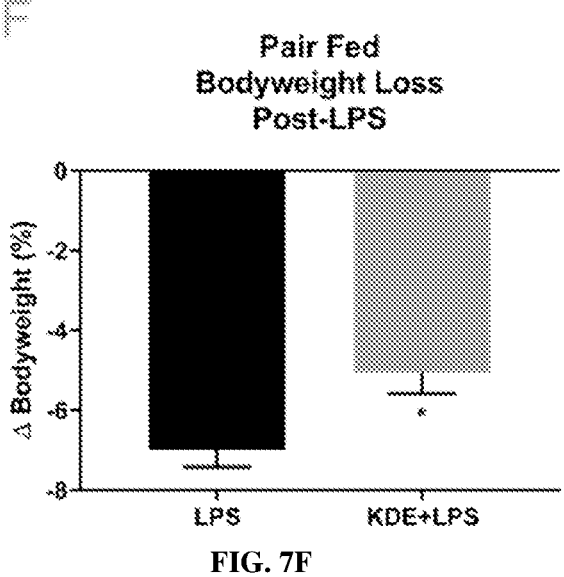

Animals were followed over a 13-day period to determine chronic effects of KDE. KDE significantly attenuated chronic LPS-induced bodyweight loss (FIG. 7D). To determine whether KDE would alter length of recovery time from a maximal non-fatal LPS dose, bodyweight was assessed over the 13-day time-period to determine length of time before animals returned to baseline bodyweight. KDE+LPS recovered within 10 days, while LPS did not recover within the 13-day time-period (FIG. 7E). While this illustrates that a single KDE administration could rapidly alter systemic metabolism and attenuate catabolism and comorbid symptoms, reducing anorexia can potentially confound catabolism. To determine if KDE attenuated catabolism in post-LPS administration when controlling for anorexia, animals were pair-fed and administered a single 4 mL/kg gavage. Pair-fed KDE+LPS significantly reduced bodyweight loss 28% compared to LPS group (FIG. 7F), indicating KDE attenuated catabolism independent of food intake. Taken together, the KDE attenuated anorexia and catabolism in a cancer-independent inflammatory-atrophy environment when comorbidities were controlled, suggesting a direct anti-catabolic effect of KDE in these multifactorial catabolic environments.

Discussion: An inability to model the clinically reported environment of progressive metastatic CACS and discover effective treatments that mitigate both muscle atrophy and comorbid symptoms has impeded clinical advancements in the most commonly affected patient population, advanced metastatic cancer patients. The results herein demonstrate that the VM-M3 model replicates the progressive and spontaneous nature of metastatic disease which facilitates the development of the full clinical CACS environment via progressive wasting of skeletal muscle with observed alterations in IGF-1/insulin, FOXO3a, and ubiquitin proteasome degradation pathway, along with adipose tissue wasting, systemic inflammation, anorexia, anemia, hypoalbuminemia, elevated protein breakdown, and metabolic derangement with sex-specific discrepancies. Additionally, this example demonstrates that the administration of a non-toxic KDE added to a standard diet was well tolerated, shifted systemic metabolism, mitigated comorbid symptoms, attenuated tumor burden indices, and reduced catabolism in both the progressive metastatic CACS and cancer-independent septic/inflammatory atrophy environments. These results illustrate that the KDE is a unique, novel and multifaceted anti-CACS therapeutic with direct anti-catabolic effects in atrophy environments.

The VM-M3 model presents a unique metastatic model in which subcutaneously implanted VM-M3 luciferase-expressing cells can develop a primary tumor, spontaneously leave the primary tumor site, enter the circulation, and produce distant metastases that can be monitored by bioluminescence imaging. Intraperitoneal implantation of VM-M3 cells also induced similar systemic metastases, progressive tumor burden, and CACS phenotype to subcutaneous implantation illustrating a consistent modeling system. This is distinct from other models which require intravenous implantation or the assistance of surgical resection of the primary tumor to induce metastases. The reliable, reproducible, and logistically feasible nature of this metastatic model may present numerous experimental advantages over emergent genetically engineered modeling systems which often require lengthy and costly experimental designs due to heterogeneous tumor onset and growth, metastatic progression, and cachexia occurrence. Additionally, metastases can directly disrupt cancer-burdened tissue and indirectly disrupt non-cancerous tissue through secretory factors or alterations in host-tissue response, further highlighting the need to model the complex metastatic CACS.

Among the hallmark characteristics of cachexia is the atrophy of skeletal muscle and often adipose tissue, with bodyweight being most commonly used clinically as a surrogate marker for both due to ease of assessment. It is important to note, however, that tissues can atrophy and/or hypertrophy in an asymmetric manner, highlighted in cancer patients with sarcopenia obesity and in cachexia trials using appetite stimulants, where it has been reported that adipose tissue can increase while skeletal muscle progressively atrophies. Similarly, the non-specificity of bodyweight as a determinant for cachexia status was demonstrated, while tissue specific assessment of wasting did reveal progressive skeletal muscle wasting, the hallmark characteristic of cachexia. Interestingly, while hind limb weights atrophied in a progressive manner, decreases in quadriceps was not observed in tissue until after week 3. This preferential retention in quadricep muscle mass over gastrocnemius and soleus has also been reported in the C26 cachexia rodent model and in patients with disuse atrophy. This may be explained by gene expression differences across muscle groups as epigenetic modulation of gene expression has been shown to regulate wasting in cachexia, disuse atrophy, and nutrient deprivation. While quadricep atrophy across sexes was observed, sex-specific quadricep wasting has been previously reported, highlighting a reported need for further sex-specific analysis in clinical cohorts. While skeletal muscle wasting is central to the disease, adipose tissue wasting has gained considerable attention, as recent reports have demonstrated that adipose tissue wasting may regulate skeletal muscle wasting in several cachexia models. It was demonstrated that VM-M3 males had progressive adipose tissue wasting, while VM-M3 females demonstrated sex-specific retention of adipose tissue until after week 3. Previous reports confirm differential degree and timing of tissue wasting and function between males and females, hypothesized or explained by hormonal differences.

While metastasis and tissue wasting are important components of CACS, accompanying systemic inflammation, anorexia, anemia, elevated protein breakdown, hypoalbuminemia, and metabolic derangement demonstrate the full multifactorial CACS. Inflammation has been commonly reported to play roles in multiple aspects of the CACS wasting scenario including tissue wasting, anorexia, metabolic abnormalities, tumor progression, among others. Progressive systemic inflammation was observed across metrics of spleen enlargement, white blood cell elevation, and augmented pro-inflammatory cytokines. Anorexia is a common, contributory, and clinically impactful side effect of CACS. Both cachexia and anorexia can be mechanistically driven by a pro-inflammatory state, which were simultaneously observed in the VM-M3 model. Finally, it was demonstrated that the VM-M3 model had the comprehensive clinical biomarkers observed in cachexia patients, that are often unevaluated in rodent model systems, including anemia, metrics of protein breakdown, hypoalbuminemia, and metabolic derangement. This is salient as many mechanisms and therapeutic strategies proposed for CACS are largely dependent on modeling systems known to not recapitulate or remain unevaluated for the full CACS.

Multiple driving mechanisms of skeletal muscle atrophy have been proposed and explored for cachexia, yet limited patient data leads to many unanswered questions related to the underlying drivers at the skeletal muscle level. However, emerging evidence from rodent models indicates that the ubiquitin proteasome degradation pathway is a prominent contributor to skeletal muscle atrophy. Elevated serum TNF-α and skeletal muscle protein poly-ubiquitination were observed, without alterations in acute or chronic markers suggestive of NF-κB activation which could be explained by an observed elevation in IL-10 serum levels. However, significantly reduced serum IGF-1 and insulin levels along with elevated nuclear FOXO3a levels in skeletal muscle were observed; the latter being an established upstream modulator of the ubiquitin proteasome pathway. Importantly, IGF-1/insulin signaling has an established role in muscle homeostasis and alterations in pathway modulators and/or signaling components have been observed in patients across multiple atrophy environments including cachexia, nutrient deprivation/anorexia, sepsis, diabetes, sarcopenia, amongst others, demonstrating a clinically relevant mechanism in atrophy-based disease.

While the VM-M3 model serves as a robust and comprehensive modeling system for CACS, there is currently no effective treatment for this multifaceted disease. KDE is a non-toxic synthetic exogenous ketone compound composed of a R/S 1,3-butanediol backbone esterified to two acetoacetates. Upon oral administration, KDE increases circulating levels of the ketone bodies β-hydroxybutyrate and acetoacetate, while decreasing blood glucose in a dose-dependent manner without the barriers of whole lifestyle/dietary changes or IV infusion. Elevations in circulating ketone bodies and decreases in blood glucose in a dose-dependent manner were observed when administered chronically via food and acutely via oral gavage in the context of a standard diet. This presents a major step toward the clinical advancement of ketone therapeutics as fasting-induced ketone elevations and glucose reductions in cachexia patients are contraindicated, due to a fear that nutrient deprivation will exacerbate tissue atrophy. While the very-low carbohydrate ketogenic diet has overlapping metabolic effects and circumvents nutrient deprivation, major dietary modifications are difficult for some patients to sustain, and compliance can be further complicated by disease. Moreover, while direct IV infusion of metabolites into circulation allows for dose-dependent elevations in circulating ketone bodies without altering diet, this is limited to the clinical or research environment. Thus, KDE provides an orally consumable and well tolerated method for modulating systemic metabolism without dietary restriction or direct circulatory infusion.

Tumor burden and metastatic spread directly impact cachexia risk and progression. Prior work has demonstrated that a very-low carbohydrate ketogenic diet can attenuate cancer burden across various preclinical cancer models.

Ketone bodies have also been demonstrated to induce direct anti-cancer effects which have been proposed to occur via alterations in energetic metabolism, oxidative stress, inflammation, and/or epigenetic regulation. Here it was demonstrated that chronic KDE administration in the context of a standard diet mitigated indices of tumor burden. Interestingly, while one would expect caloric restriction to induce an anti-tumor response, KDE anti-tumor response was present even though comorbid anorexia (involuntary caloric restriction) was mitigated in the KDE group. Seemingly contrary to the KDE anti-anorexic effects presented here are the ketone-induced reduction in food intake previously reported. This was achieved through the alteration of standard diet palatability and a step-wise integration of KDE to mitigate this confounder in non-diseased animals. Additionally, it was demonstrated that the KDE mitigated anorexia in both the CACS and LPS/septic anorexic environments. Given the established role of inflammation in anorexia and the reported anti-inflammatory effects of KDE, it is possible that ketones may mitigate anorexia via alterations in systemic inflammation in both CACS and LPS/sepsis.

Atrophy/Catabolism is the hallmark characteristic of CACS and ketone bodies have been shown to be associated with or directly reduce metrics of protein breakdown across various populations following nutrient deprivation, acute IV infusion or through in vitro analysis. However, the chronic effects of ketone bodies on the principle outcome, atrophy/catabolism, have not been determined, nor has the efficacy of orally administered exogenous ketone bodies been tested across various multifaceted atrophy environments. Here it was demonstrated that administration of oral exogenous ketone bodies mitigated catabolism in two multifactorial and overlapping inflammatory environments. First, KDE attenuated muscle atrophy in CACS without altered input from upstream anabolic hormones deemed mechanistically involved in tissue wasting. Second, KDE mitigated LPS/sepsis catabolism even when controlling for comorbid food intake/anorexia. Mechanistically, patients exhibited reduced IGF-1/insulin, stably decreased glucose, and increased ketone bodies during prolonged fasting-induced atrophy. These studies also uncovered that as ketone bodies become elevated, metrics of protein breakdown progressively decreased along with a 3-6-fold reduction in amino acid efflux from skeletal muscle, suggesting a direct ketone-induced effect on protein turnover. Additionally, recent work in patients with LPS/sepsis demonstrated that direct IV infusion of ketone bodies induced a potent acute anti-catabolic response in the skeletal muscle, even when controlling for the potential confounding effects of GPR109a (HCAR2) signaling on NF-κB. Importantly, fasting, LPS/sepsis, and CACS have all been shown to reduce IGF-1/insulin signaling. This overlapping atrophy signaling in the present example indicates that ketone bodies attenuate catabolism in all three conditions, even when controlling for confounding GPR109a/NF-κB signaling and circulating IGF-1/insulin levels suggests other possible mechanisms. Ketone-induced histone acetylation via Class I and II Histone Deacetylase (HDAC) inhibition is one possible anti-catabolic mechanism as 1) class I and II HDAC induced atrophy occurs across multiple catabolic states; 2) inhibition of Class I and II HDACs and the subsequent histone acetylation in skeletal muscle is sufficient to inhibit skeletal muscle atrophy via the restriction of FOXO3a nuclear accumulation; 3) genetic deletion of HDAC4 attenuates activations of ubiquitin proteasome degradation in multiple models of atrophy; 4) ketone bodies inhibit class I and II HDACs and promote histone acetylation in many tissues, including skeletal muscle; 5) ketone bodies elicit anti-atrophy effects across multiple catabolic environments. However, there is also evidence that FOXO3a levels increase with diet-induced ketone elevations. Still, neither analysis indicated FOXO3a skeletal muscle nuclear localization. Additionally, FOXO3a has consistently been shown to induce atrophy in skeletal muscle, which contradicts work demonstrating the anti-atrophy effect of ketone bodies in environments where IGF-1/insulin signaling is commonly suppressed. However, ketone bodies have been demonstrated to have other anti-catabolic mechanisms which cannot be ruled out in the present analysis. Thus, KDE-induced inhibition of class I and II HDAC, the subsequent histone acetylation, and efflux of nuclear FOXO3a, along with regulatory capacity across catabolic, synthetic and metabolic pathways, present potential anti-atrophy mechanism(s) which should be examined in future analysis. Additionally, while STAT3—and autophagy-induced atrophy signaling remain unexplored in the current analysis, the observed elevations in serum IL-6 and skeletal muscle FOXO3a nuclear localization indicates that one cannot exclude these potentially contributory pathways.

While this example suggest ketone bodies have a pluripotent therapeutic role in wasting environments, the ability of the KDE to induce these effects without altering circulating anabolic hormones may have important clinical relevance. First, various attempts to inhibit FOXO3a and ubiquitin proteasome degradation in the inflammatory environment via elevations in anabolic hormones have not proven efficacious. This is likely due to skeletal muscle resistance to IGF-1/insulin signaling in these inflammatory environments. While inflammation-induced IGF-1/insulin resistance is not fully understood, multiple reports indicate this may be occurring at the receptor level. Interestingly, this example demonstrated an anti-catabolic effect of ketone bodies across low IGF-1/insulin signaling and pro-inflammatory environments demonstrating that ketones may present a modulatory tool for this catabolic pathway by circumventing previous therapeutic resistance. Secondly, discussion has emerged around the proposed dichotomy of IGF-1 on skeletal muscle mass, cancer growth and metastasis, and longevity. Thus, ketone bodies' ability to promote optimal muscle mass while mitigating perceived risk for adverse health or disease outcomes is a finding worth future clinical exploration. Beyond tissue atrophy/catabolism, ketone bodies have been demonstrated to directly regulate metabolism, reduce oxidative stress, attenuate inflammation, and regulate epigenetics, amongst other effects. Consequently, ketone bodies may help support improved patient outcomes across various multifaceted diseases including cancer, CACS, sepsis, amongst others, where atrophy/catabolism is only one component compromising patient outcomes.

Taken together, this work demonstrates a comprehensive, metastatic, and progressive model of CACS with sex-specific variation, and a non-toxic exogenous ketone therapy with metabolic, anti-catabolic, anti-anorexic, anti-tumor therapeutic effects across various multifaceted atrophy/catabolic environments. Future studies are warranted to further investigate other mechanisms through which the KDE attenuates atrophy and comorbidities, determine optimal KDE administration protocol, evaluate potential synergistic therapeutic strategies to optimize therapeutic effect, and most notably, determine whether KDE can be a supportive nutritional therapeutic in clinical CACS and inflammatory atrophy environments.

TABLE 1

| | | | | | Bioluminescence | | | |
|---|---|---|---|---|---|---|---|---|
| Experiments | Cohorts (n) | Survival | Bodyweight | Food Intake | (Whole Animal & Organs) | Blood Glucose | Blood R βHB | Blooad Lactate |
| 1a | CA-M (n = 12) SH-M (n = 12) CA-F (n = 12) SH-F (n = 12)* | EOL | Daily | Daily | Weekly (Whole Animal) EOL (Whole Animal & Ex w/wo Organs) | Weekly | Weekly | |
| 1b | CA-M (n = 8) SH-M (n = 8) CA-F (n = 8) SH-F (n = 8) | EOL | Weekly | Weekly | Weekly | | | |
| 2 | Week 1 CA-M (n = 4) SH-M (n = 4) CA-F (n = 5) SH-F (n = 5) Week 2 CA-M (n = 4) SH-M (n = 4) CA-F (n = 5) SH-F (n = 5) Week 3 CA-M (n = 5) SH-M (n = 5) CA-F (n = 6) SH-F (n = 6) | | Daily | | Weekly | | | |
| 3 | CA-M (n = 8) SH-M (n = 8) | | | | | | | Weekly |
| 4a | 20% KDE (n = 5) 25% KDE (n = 5) 30% KDE (n = 5) | | Daily | Daily | | Pre/Post | Pre/Post | |
| 4b | 0→30% KDE (n = 4) | | Daily | Daily | | | | |

TABLE 1-continued

| Experimental Design reference table for main experiments. | | | | | | |
|---|---|---|---|---|---|
| 4c | KDE + VM-M3 (n = 12) VM-M3 (n = 12) Sham (n = 12)* | Daily | Daily | Weekly | Weekly | Weekly | Weekly |
| 5a | 2 mL/kg KDE (n = 3) 3 mL/kg KDE (n = 2) 4 mL/kg KDE (n = 3) 5 mL/kg KDE (n = 3) | | | | | Hourly | Hourly |
| 5b | LPS (n = 4) KDE + LPS (n = 5) | Daily | Daily | | | | |
| 5c | LPS (n = 4) KDE + LPS (n = 4) | Daily | Daily | | | | |

| Experiments | Cohorts (n) | Tissue Composition | Cytokines | Clinical Chemistry | Complete Blood Count | Serum Hormones | Tissue Signaling |
|---|---|---|---|---|---|---|---|
| 1a | CA-M (n = 12) SH-M (n = 12) CA-F (n = 12) SH-F (n = 12)* | EOL | Baseline, Week 2 & EOL | EOL | EOL | | EOL |
| 1b | CA-M (n = 8) SH-M (n = 8) CA-F (n = 8) SH-F (n = 8) | EOL | | EOL | EOL | | |
| 2 | Week 1 CA-M (n = 4) SH-M (n = 4) CA-F (n = 5) SH-F (n = 5) Week 2 CA-M (n = 4) SH-M (n = 4) CA-F (n = 5) SH-F (n = 5) Week 3 CA-M (n = 5) SH-M (n = 5) CA-F (n = 6) SH-F (n = 6) | | Week 1, 2 & 3 | | | | |
| 3 | CA-M (n = 8) SH-M (n = 8) | | | | | | |
| 4a | 20% KDE (n = 5) 25% KDE (n = 5) 30% KDE (n = 5) | | | | | | |
| 4b | 0→30% KDE (n = 4) | | | | | | |
| 4c | KDE + VM-M3 (n = 12) VM-M3 (n = 12) Sham (n = 12)* | Week 3 | | | | Week 3 | |
| 5a | 2 mL/kg KDE (n = 3) 3 mL/kg KDE (n = 2) 4 mL/kg KDE (n = 3) 5 mL/kg KDE (n = 3) | | | | | | |
| 5b | LPS (n = 4) KDE + LPS (n = 5) | | | | | | |
| 5c | LPS (n = 4) KDE + LPS (n = 4) | | | | | | |

Abbreviations: R βHB, R β-Hydroxybutyrate; SH-M, Sham Males; CA-M, Cancer Males; SH-F, Sham Females; CA-F, Cancer Females; EOL, End of Life; VM-M3, VM-M3 Mouse Model of Systemic Metastasis; KDE, Ketone Diester; LPS, Lipopolysaccharide/Endotoxin.
*One unexplained animal death immediately postinoculation The advantages set forth above, and those made apparent from the foregoing description, are efficiently attained. Since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention that, as a matter of language, might be said to fall therebetween.

The invention claimed is:

1. A method for reducing, delaying, or reversing effects due to aging in a subject in need thereof, the method comprising:

administering a therapeutically effective amount of a ketogenic supplement to the subject, in an amount of greater than 5% by weight of the subject's diet or greater than 10% of the subject's total daily caloric intake, wherein the ketogenic supplement comprises R,S-1,3-butanediol diacetoacetate wherein the subject is age sixty-five (65) or over, and wherein the subject is fed ad libitum.

2. The method of claim 1, wherein the subject exhibits elevated levels of insulin-like growth factor-1 (IGF-1), insulin, or a combination thereof, compared to an average level of IGF-1 or insulin in a population of subjects under age sixty-five (65); elevated levels of one or more cytokines compared to an average level of cytokine in a population of subjects under age sixty-five (65); elevated levels of poly-ubiquitination or FOXO3a compared to an average level of poly-ubiquitination or FOXO3a in a population of subjects under age sixty-five (65); or any combination thereof.

3. The method of claim 1, wherein the subject has anemia, hypoalbuminemia, hypocholesterolemia, inflammation, malnutrition/anorexia/starvation, splenomegaly, or a combination thereof.

4. The method of claim 1, wherein the ketogenic supplement further comprises a medium chain triglyceride, a beta-hydroxybutyrate, a beta-hydroxybutyrate precursor, an acetoacetate, an acetoacetate precursor, a beta-hydroxybutyrate mineral salt, a beta-hydroxybutyrate amino acid, a beta-hydroxybutyrate fatty acid, acetoacetate mineral salt, acetoacetate amino acid, acetoacetate fatty acid, a or a combination thereof.

5. The method of claim 1, wherein the ketogenic supplement is administered in an amount from 5% to 100% by weight of the subject's diet.

6. The method of claim 1, wherein the ketogenic supplement is administered in an amount up to 100% of total daily caloric intake based on the subject's diet.

7. The method of claim 1, wherein the ketogenic supplement is administered in an amount from 5% to 100% of total daily caloric intake based on the subject's diet.

8. The method of claim 1, wherein the ketogenic supplement is administered at about 0.001 g/kg/day to about 10 g/kg/day.

9. The method of claim 1, wherein the amount of ketogenic supplement is gradually administered to the subject, comprising an incremental dose elevation of at least 5% by weight of the subject's diet per day or at least 10% of total calorie intake per day.

10. The method of claim 1, wherein the ketogenic supplement is administered orally.

11. The method of claim 1, wherein the method further comprises administering a second agent selected from the group consisting of an antioxidant, a different anti-aging agent, an anti-inflammatory, a metabolic regulatory agent, or a combination thereof.

12. A method for treating, or reducing time to recovery from a disease associated with aging in a subject in need thereof, the method comprising:

administering a therapeutically effective amount of a ketogenic supplement to the subject, in an amount of greater than 5% by weight of the subject's diet or greater than 10% of the subject's total daily caloric intake, wherein the ketogenic supplement comprises R,S-1,3-butanediol diacetoacetate, and wherein the subject is fed ad libitum.

13. The method of claim 12, wherein the disease is anemia; hypoalbuminemia; hypocholesterolemia; inflammation; malnutrition/anorexia/starvation; splenomegaly; related to elevated levels of insulin-like growth factor-1 (IGF-1), insulin, or a combination thereof; related to elevated levels of one or more cytokines; related to elevated levels of poly-ubiquitination or FOXO3a; or a combination thereof.

14. The method of claim 12, wherein the ketogenic supplement further comprises a medium chain triglyceride, a beta-hydroxybutyrate, a beta-hydroxybutyrate precursor, an acetoacetate, an acetoacetate precursor, a beta-hydroxybutyrate mineral salt, a beta-hydroxybutyrate amino acid, a beta-hydroxybutyrate fatty acid, acetoacetate mineral salt, acetoacetate amino acid, acetoacetate fatty acid, a or a combination thereof.

15. A method for reducing or delaying effects due to aging in a subject in need thereof, the method comprising:

administering a therapeutically effective amount of a ketogenic supplement to the subject, in an amount of greater than 5% by weight of the subject's diet or greater than 10% of the subject's total daily caloric intake, wherein the ketogenic supplement comprises R,S-1,3-butanediol diacetoacetate, wherein the subject is age thirty-five (35) or over, and wherein the subject is fed ad libitum.

16. The method of claim 15, wherein the subject is healthy.

17. The method of claim 15, wherein the ketogenic supplement further comprises a medium chain triglyceride, a beta-hydroxybutyrate, a beta-hydroxybutyrate precursor, an acetoacetate, an acetoacetate precursor, a beta-hydroxybutyrate mineral salt, a beta-hydroxybutyrate amino acid, a beta-hydroxybutyrate fatty acid, acetoacetate mineral salt, acetoacetate amino acid, acetoacetate fatty acid, or a combination thereof.

* * * * *

SEQUENCE LISTING

```
<160> NUMBER OF SEQ ID NOS: 12

<210> SEQ ID NO 1
<211> LENGTH: 20
<212> TYPE: DNA
<213> ORGANISM: Artificial Sequence
<220> FEATURE:
<223> OTHER INFORMATION: Synthetic construct

<400> SEQUENCE: 1
tcagctctgt gaccgatacg                                                    20

<210> SEQ ID NO 2
<211> LENGTH: 20
<212> TYPE: DNA
<213> ORGANISM: Artificial Sequence
<220> FEATURE:
<223> OTHER INFORMATION: Synthetic construct

<400> SEQUENCE: 2
gccacagacc acatcacaac                                                    20

<210> SEQ ID NO 3
<211> LENGTH: 20
<212> TYPE: DNA
<213> ORGANISM: Artificial Sequence
<220> FEATURE:
<223> OTHER INFORMATION: Synthetic construct

<400> SEQUENCE: 3
cctgccctcc acatcctttt                                                    20

<210> SEQ ID NO 4
<211> LENGTH: 20
<212> TYPE: DNA
<213> ORGANISM: Artificial Sequence
<220> FEATURE:
<223> OTHER INFORMATION: Synthetic construct

<400> SEQUENCE: 4
gaagggggag agtggggtat                                                    20

<210> SEQ ID NO 5
<211> LENGTH: 20
<212> TYPE: DNA
<213> ORGANISM: Artificial Sequence
<220> FEATURE:
<223> OTHER INFORMATION: Synthetic construct

<400> SEQUENCE: 5
ccatcctctt tcttgcccgt                                                    20

<210> SEQ ID NO 6
<211> LENGTH: 20
<212> TYPE: DNA
<213> ORGANISM: Artificial Sequence
<220> FEATURE:
<223> OTHER INFORMATION: Synthetic construct
```

-continued

```
<400> SEQUENCE: 6
atcactgtcc aacctggctg                                                20

<210> SEQ ID NO 7
<211> LENGTH: 20
<212> TYPE: DNA
<213> ORGANISM: Artificial Sequence
<220> FEATURE:
<223> OTHER INFORMATION: Synthetic construct

<400> SEQUENCE: 7
tgggacagat gaggaggagg                                                20

<210> SEQ ID NO 8
<211> LENGTH: 20
<212> TYPE: DNA
<213> ORGANISM: Artificial Sequence
<220> FEATURE:
<223> OTHER INFORMATION: Synthetic construct

<400> SEQUENCE: 8
tttaccctct gtggtcacgc                                                20

<210> SEQ ID NO 9
<211> LENGTH: 20
<212> TYPE: DNA
<213> ORGANISM: Artificial Sequence
<220> FEATURE:
<223> OTHER INFORMATION: Synthetic construct

<400> SEQUENCE: 9
gatgaaaaca tcgccaaggt                                                20

<210> SEQ ID NO 10
<211> LENGTH: 20
<212> TYPE: DNA
<213> ORGANISM: Artificial Sequence
<220> FEATURE:
<223> OTHER INFORMATION: Synthetic construct

<400> SEQUENCE: 10
cctccagtcc cagttatgga                                                20

<210> SEQ ID NO 11
<211> LENGTH: 20
<212> TYPE: DNA
<213> ORGANISM: Artificial Sequence
<220> FEATURE:
<223> OTHER INFORMATION: Synthetic construct

<400> SEQUENCE: 11
accaccctgt gacctcagtc                                                20

<210> SEQ ID NO 12
<211> LENGTH: 20
<212> TYPE: DNA
<213> ORGANISM: Artificial Sequence
<220> FEATURE:
<223> OTHER INFORMATION: Synthetic construct

<400> SEQUENCE: 12
ctcctggaaa cccagaacaa                                                20
```